US012180254B1

(12) United States Patent
Song et al.

(10) Patent No.: US 12,180,254 B1
(45) Date of Patent: Dec. 31, 2024

(54) FACTOR H VARIANTS FOR TREATMENT OF DISEASE

(71) Applicant: The Trustees of the University of Pennsylvania, Philadelphia, PA (US)

(72) Inventors: Wenchao Song, Bryn Mawr, PA (US); Damodar Gullipalli, Philadelphia, PA (US); Takashi Miwa, Bala Cynwyd, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 18/494,883

(22) Filed: Oct. 26, 2023

Related U.S. Application Data

(63) Continuation of application No. 17/156,023, filed on Jan. 22, 2021, now abandoned, which is a continuation of application No. 15/762,721, filed as application No. PCT/US2016/053347 on Sep. 23, 2016, now Pat. No. 10,988,519.

(60) Provisional application No. 62/232,008, filed on Sep. 24, 2015.

(51) Int. Cl.
*C12N 15/85* (2006.01)
*A61P 13/12* (2006.01)
*C07K 14/47* (2006.01)
*C12N 15/86* (2006.01)

(52) U.S. Cl.
CPC .......... *C07K 14/4702* (2013.01); *A61P 13/12* (2018.01); *C12N 15/86* (2013.01); *C12N 2750/14143* (2013.01); *C12N 2750/14145* (2013.01)

(58) Field of Classification Search
CPC ..... C07K 14/4702; A61P 13/12; C12N 15/86; C12N 2750/14143; C12N 2750/14145
See application file for complete search history.

(56) References Cited

U.S. PATENT DOCUMENTS

| | | | | |
|---|---|---|---|---|
| 5,139,941 | A | 8/1992 | Muzyczka et al. | |
| 5,478,745 | A | 12/1995 | Samulski et al. | |
| 5,741,683 | A | 4/1998 | Zhou et al. | |
| 6,057,152 | A | 5/2000 | Samulski et al. | |
| 6,204,059 | B1 | 3/2001 | Samulski et al. | |
| 6,268,213 | B1 | 7/2001 | Samulski et al. | |
| 6,491,907 | B1 | 12/2002 | Rabinowitz et al. | |
| 6,596,535 | B1 | 7/2003 | Carter | |
| 6,660,514 | B1 | 12/2003 | Zolotukhin et al. | |
| 6,951,753 | B2 | 10/2005 | Shenk et al. | |
| 7,094,604 | B2 | 8/2006 | Snyder et al. | |
| 7,125,717 | B2 | 10/2006 | Carter | |
| 7,172,893 | B2 | 2/2007 | Rabinowitz et al. | |
| 7,201,898 | B2 | 4/2007 | Monahan et al. | |
| 7,229,823 | B2 | 6/2007 | Samulski et al. | |
| 7,282,199 | B2 | 10/2007 | Gao et al. | |
| 7,439,065 | B2 | 10/2008 | Ferrari et al. | |
| 7,456,683 | B2 | 11/2008 | Takano et al. | |
| 7,588,772 | B2 | 9/2009 | Kay et al. | |
| 7,790,449 | B2 | 9/2010 | Gao et al. | |
| 7,906,111 | B2 | 3/2011 | Wilson et al. | |
| 8,319,480 | B2 | 11/2012 | Ko et al. | |
| 8,962,330 | B2 | 2/2015 | Gao et al. | |
| 8,962,332 | B2 | 2/2015 | Gao et al. | |
| 2007/0036760 | A1 | 2/2007 | Wilson et al. | |
| 2008/0221011 | A1 | 9/2008 | Gilkeson et al. | |
| 2009/0197338 | A1 | 8/2009 | Vandenberghe et al. | |
| 2010/0009393 | A1* | 1/2010 | Morgan | C07K 16/18 530/389.3 |
| 2013/0045186 | A1 | 2/2013 | Gao et al. | |
| 2013/0296255 | A1 | 11/2013 | Hageman | |
| 2015/0110766 | A1 | 4/2015 | Lambris et al. | |
| 2015/0139975 | A1 | 5/2015 | Schmidt et al. | |
| 2016/0304902 | A1* | 10/2016 | Kim | C12P 21/00 |
| 2017/0190753 | A1* | 7/2017 | Abache | A01K 67/0275 |
| 2018/0230488 | A1 | 8/2018 | Hinderer et al. | |

FOREIGN PATENT DOCUMENTS

| | | | | |
|---|---|---|---|---|
| EP | 1310571 | | 2/2006 | |
| RU | 2417099 | C2 | 4/2011 | |
| WO | WO 1995/008570 | A1 | 3/1995 | |
| WO | WO 2003/042397 | | 5/2003 | |
| WO | WO 2005/033321 | | 4/2005 | |
| WO | WO 2006/088950 | | 8/2006 | |
| WO | WO 2006/110689 | | 10/2006 | |
| WO | WO 2007056227 | A2 | 5/2007 | |
| WO | WO 2011/077102 | A1 | 6/2011 | |
| WO | WO 2011/107591 | | 9/2011 | |
| WO | WO 2011/126808 | | 10/2011 | |
| WO | WO 2011/163412 | | 12/2011 | |
| WO | WO-2011163412 | A1 * | 12/2011 | A61K 39/395 |
| WO | WO 2013/049493 | | 4/2013 | |

(Continued)

OTHER PUBLICATIONS

Kumar-Singh et al entitled "Rescue of Complement Mediated Pathology in a Murine Model of Macular Degeneration by Adenovirus-Mediated Delivery of the Alternative Pathway Regulator, Factor H". (Invest Ophthalmol Vis Sci.; Apr. 2014, vol. 55, p. 1319). (Year: 2014).*

Horl et al "Complement factor H-derived short consensus repeat 18-20 enhanced complement-dependent cytotoxicity of ofatumumab on chronic lymphocytic leukemia cells" (haematologica 2013; vol. 98, No. 12, pp. 1939-1947). (Year: 2013).*

Duthy et al entitled "The Human Complement Regulator Factor H Binds Pneumococcal Surface Protein PspC via Short Consensus Repeats 13 to 15", Infect Immun, Oct. 2002, vol. 70, No. 10, pp. 5604-5611; IDS reference). (Year: 2002).*

Kuhn et al (The Journal of Immunology 1995 vol. 155, No. 12, pp. 5663-5670 (Year: 1995).*

Barata et al., Deletion of Crry and DAF on murine platelets stimulates thrombopoiesis and increases fH-dependent resistance of peripheral platelets to complement attack, J. Immunol, vol. 190(6):2886-95, Feb. 2013.

(Continued)

*Primary Examiner* — Catherine S Hibbert
(74) *Attorney, Agent, or Firm* — Howson & Howson LLC

(57) ABSTRACT

Disclosed herein are factor H variants, vectors comprising said factor H variants, and pharmaceutical compositions comprising the same for treatment of disorders.

24 Claims, 38 Drawing Sheets

Specification includes a Sequence Listing.

(56) References Cited

FOREIGN PATENT DOCUMENTS

| | | | |
|---|---|---|---|
| WO | WO 2013/142362 | 9/2013 | |
| WO | WO-2013142362 A1 * | 9/2013 | ............ A61K 38/51 |
| WO | WO 2014/124282 | 8/2014 | |
| WO | WO-2014188042 A1 * | 11/2014 | ............ C12N 15/86 |
| WO | WO 2015/012924 | 1/2015 | |
| WO | WO 2015/092335 | 6/2015 | |
| WO | WO 2017/072515 | 5/2017 | |
| WO | WO 2020/210480 | 10/2020 | |

OTHER PUBLICATIONS

Beltran et al., rAAV2/5 gene-targeting to rods:dose-dependent efficiency and complications associated with different promoters, Gene Therapy, vol. 17(9):1162-74, Apr. 2010.

Buning et al., Recent developments in adeno-associated virus vector technology, J. Gene Med., vol. 10(7):717-733, Jul. 2008.

Cai et al., A 350 bp region of the proximal promoter of Rds drives cell-type specific gene expression, Exp Eye Res., vol. 91(2):186-94, Aug. 2010.

Estaller et al,, Human complement factor H: Two factor H proteins are derived from alternatively spliced transcripts, Eur J Immunol., vol. 21(3):799-802, Mar. 1991.

Duthy et al., The human complement regulator factor H binds pneumococcal surface protein PspC via short consensus repeats 13 to 15, Infect Immun. Oct. 2002;70(10):5604-11.

Dunkelberger, et al., C5aR Expression in a Novel GFP Reporter Gene Knockin Mouse: Implications for the Mechanism of Action of C5aR Signaling in T Cell Immunity, J Immunol., vol. 188(8):4032-4042, Apr. 2012.

Fakhouri et al., Treatment with human complement factor H rapidly reverses renal complement deposition in factor H-deficient mice, Kidney International, vol. 78(3):279-286, May 2010.

Fee et al., PEG-proteins: Reaction engineering and separation issues, Chemical Engineering Science, vol. 61(3):924-939, Feb. 2006.

Fridkis-Hareli et al., Design and development of TT30, a novel C3d-targeted C3/C5 convertase inhibitor for treatment of human complement alternative pathway-mediated diseases, vol. 118(17):4705-13, Aug. 2011.

Gao et al., Adeno-associated viruses undergo substantial evolution in primates during natural infections, Proc. Natl. Acad. Sci. U.S.A., vol. 100(10):6081-6086, May 2003.

GenBank Accession No. AY327580, *Homo sapiens* rhodopsin kinase gene, promoter region, exon 1 and partial cds, Jul. 2016.

GenBank Accession No. YP_077180, capsid protein [Adeno-associated virus—8], Aug. 2018.

Gullipalli et al., Therapeutic efficacy of AAV-mediated factor H gene transfer in a murine model of lethal C3 glomerulopathy, Molecular Immunology, 102, Oct. 2018, p. 157.

Hebecker et al., An engineered construct combining complement regulatory and surface-recognition domains represents a minimal-size functional factor H. J Immunol. Jul. 15, 2013;191(2):912-21. doi: 10.4049/jimmunol.1300269. Published online Jul. 3, 2013.

Mowat et al., Tyrosine capsid-mutant AAV vectors for gene delivery to the canine retina from a subretinal or intravitreal approach, Gene Therapy, vol. 21:96-105, Jan. 2014.

Grieger & Samulski, Adeno-associated virus as a gene therapy vector: Vector development, production and clinical applications, Adv. Biochem. Engin/Biotechnol., vol. 99:119-145, Oct. 2005.

Fisher et al., J. Virol., Transduction with recombinant adeno-associated virus for gene therapy is limited by leading-strand synthesis, vol. 70:520-532, Jan. 1996.

Kachi et al., Equine Infectious Anemia Viral Vector-Mediated Codelivery of Endostatin and Angiostatin Driven by Retinal Pigmented Epithelium-Specific VMD2 Promoter Inhibits Choroidal Neovascularization, Human Gene Therapy, vol. 20(1):31-9, Jan. 2009.

Kay et al., Targeting Photoreceptors via Intravitreal Delivery Using Novel, Capsid-Mutated AAV Vectors, PLoS One., vol. 8(4): e62097, Apr. 2013.

Kimura et al., Genetic and therapeutic targeting of properdin in mice prevents complement-mediated tissue injury, J Clin Invest., vol. 120(10):3545-54, Oct. 2010.

Kimura et al., Activator-specific requirement of properdin in the initiation and amplification of the alternative pathway complement, Blood, vol. 111(2):732-40, Jan. 2008 (Epub Oct. 2007).

Kumar-Singh et al., Rescue of Complement Mediated Pathology in a Murine Model of Macular Degeneration by Adenovirus Mediated Delivery of the Alternative Pathway regulator, Factor H, Invest Ophthalmol Vis. Sci., vol. 55:1319, Apr. 2014.

Lambard et al., Expression of Rod-Derived Cone Viability Factor: Dual Role of CRX in Regulating Promoter Activity and Cell-Type Specificity, PLoS One, vol. 5(10):e13025, Oct. 2010.

Lesher et al., Combination of factor H mutation and properdin deficiency causes severe C3 glomerulonephritis, J Am Soc Nephrol., vol. 24(1):53-65, Jan. 2013 (Epub Nov. 2012).

Liu et al, Enhancing the secretion of recombinant proteins by engineering N-glycosylation sites, Biotech Prog, vol. 25(5): 1468-1475, Sep.-Oct. 2009.

McCarty et al., Self-complementary recombinant adeno-associated virus (scAAV) vectors promote efficient transduction independently of DNA synthesis, Gene Therapy, vol. 8(16):1248-1254, Aug. 2001.

Miyatake et al., Transcriptional targeting of herpes simplex virus for cell-specific replication, J. Virol., vol. 71:5124-32, Jul. 1997.

Morrissey et al., PRE-1, a cis element sufficient to enhance cone- and rod- specific expression in differentiating zebrafish photoreceptors, BMC Dev. Biol, vol. 11:3, Jan. 2011.

Mussolino et al., AAV-mediated photoreceptor transduction of the pig cone-enriched retina, Gene Ther, vol. 18(7):637-45, Mar. 2011.

Nichols et al., An extended mini-complement factor H molecule ameliorates experimental C3 glomerulopathy, Kidney Int., vol. 88(6):1314-1322, Dec. 2015 (ePub Jul. 2015).

Nicoud et al., Development of photoreceptor-specific promoters and their utility to investigate EIAV lentiviral vector mediated gene transfer to photoreceptors, J. Gene Med, vol. 9(12):1015-23, Dec. 2007.

Rodríguez et al., High-efficiency deleter mice show that FLPe is an alternative to Cre-loxP, Nat Genet., vol. 25(2):139-40, Jun. 2000.

Sola et al., Glycoslylation of therapeutic proteins: an effective strategy to optimize efficacy, BioDrugs, vol. 24(1):9-21, Feb. 2010.

Sandig et al., HBV-derived promoters direct liver-specific expression of an adenovirally transduced LDL receptor gene, Gene Ther., vol. 3(11):1002-9, Nov. 1996.

Shu et al., Functional Characterization of the Human RPGR Proximal Promoter, IOVS, vol. 53:3951-3958, Jun. 2012.

Miwa et al., Complement-dependent T-cell lymphopenia caused by thymocyte deletion of the membrane complement regulator Crry, Blood, vol. 113(12):2684-2694, Mar. 2009.

Thomson et al., A comprehensive comparison of multiple sequence alignments, Nucl. Acids. Res., vol. 27(13):2682-2690, Jul. 1999.

Zhang et al., Adenovirus adeno-associated virus hybrid for large-scale recombinant adeno-associated virus production, Human Gene Therapy, vol. 20(9):922-929, Sep. 2009.

Kaspar et al., Myocardial gene transfer and long-term expression following intracoronary delivery of adeno-associated virus, J Gene Med. Mar. 2005;7(3):316- 24.

Keiya et al., Gene therapy using AAV vectors, Drug Delivery System. Jan. 2007;22(6):643-50. [Abstract Only].

Rivera et al., Long-term pharmacologically regulated expression of erythropoietin in primates following AAV-mediated gene transfer, Blood. Feb. 15, 2005;105(4):1424-30.

International Search Report issued on International Patent Application No. PCT/US2016/053347, dated Mar. 23, 2017.

Written Opinion issued on International Patent Application No. PCT/US2016/053347, dated Mar. 23, 2017.

Supplementary European search report issued in the corresponding European counterpart Application No. 16849709.7, dated Feb. 27, 2019.

(56) References Cited

OTHER PUBLICATIONS

Supplementary European Search Report and Search Opinion issued in European Patent Application No. 16849709.7, dated Jul. 17, 2019.
Search Report and Office Action issued Feb. 25, 2020 in Russian Patent Application No. 2018114907.
Response to Communication in European Patent Application No. 16849709.7, filed Feb. 11, 2020.
Examination Report issued Jun. 26, 2020 in European Patent Application No. 16849709.7.
Office Action issued Jul. 22, 2020 in Japanese Patent Application No. 2018-515539e.
Applicant's Reply to Communication pursuant to Article 94(3) EPC in European Patent Application 16 849 709.7, filed Oct. 28, 2020.
Restriction Requirement in U.S. Appl. No. 15/762,721, dated Jul. 28, 2020.
Applicant's Response to Restriction Requirement in U.S. Appl. No. 15/762,721, filed Sep. 28, 2020.
Non-Final Office Action in U.S. Appl. No. 15/762,721, dated Jan. 7, 2021.
Applicant's Response and Amendment in U.S. Appl. No. 15/762,721, filed Jan. 28, 2021.
Notice of Allowance in U.S. Appl. No. 15/762,721, dated Feb. 11, 2021.
Office Action issued in corresponding Israeli Patent Application No. 258024, dated Jun. 3, 2021, with translation.
Final Office Action issued in corresponding Japanese Patent Application No. 2018-515539, dated Apr. 7, 2021, with translation provided by local agent.
Office Action issued in corresponding Chinese Patent Application No. 2016800642195, dated Mar. 30, 2021, with translation provided by local agent.
Communication pursuant to Article 94(3) EPC issued in European Patent Application No. 16849709.7, dated Feb. 1, 2022.
Office Action issued in corresponding Canadian Patent Application No. 2,999,299, dated Dec. 7, 2023.
Communication pursuant to Article 94(3) EPC issued in European Patent Application No. 16849709.7, dated Dec. 20, 2023.
Restriction Requirement in U.S. Appl. No. 17/156,023, dated Apr. 14, 2023.
Applicant's Response to Restriction Requirement in U.S. Appl. No. 17/156,023, filed Jun. 8, 2020.
Non-Final Office Action in U.S. Appl. No. 17/156,023, dated Sep. 29, 2023.
Office Action dated Mar. 23, 2021 issued in Brazilian Patent Application No. BR112018005684-7.
Office Action dated Oct. 17, 2022 issued in Canadian Patent Application No. 2,999,299, and Applicant's Response and Amendment filed Feb. 17, 2023.
Office Action dated Dec. 7, 2023 issued in Canadian Patent Application No. 2,999,299.
Office Action dated Jan. 18, 2022 issued in Chinese Patent Application No. 201680064219.5.
Office Action dated Jun. 3, 2021 issued in Israeli Patent Application No. 258024.
Office Action dated Jan. 8, 2024 issued in Israeli Patent Application No. 296929.
Office Action dated Sep. 14, 2022 issued in Japanese Patent Application No. 2018-515539.
Office Action dated Aug. 3, 2022 issued in Japanese Patent Application No. 2021-128847.
Office Action dated Jan. 25, 2023 issued in Japanese Patent Application No. 2021-128847.
Calton, M., Preclinical Characterization of 4D-175, a Novel AAV-based Investigational Intravitreal Gene Therapy for Geographic Atrophy. ARVO Annual Meeting, Seattle, WA. May 5-9, 2024. Oral Presentation. 15 pages.
Calton, M., Targeting the Complement Pathway with AAV-Based Gene Therapy for Geographic Atrophy. $4^{th}$ Annual Gene Therapy for Ophthalmic Disorders Summit, Boston, MA Oct. 3-5, 2023. Oral Presentation. 25 pages.
4D Molecular Therapeutics, Harnessing the Power of Directed Evolution for Targeted, Next-Generation Genetic Medicines. Oral Presentation. Jul. 2024. 72 pages.
4D Molecular Therapeutics, 4DMT Announces FDA Clearance of IND Application for 4D-175 Genetic Medicine for the Treatment of Geographic Atrophy. Press Release. Jun. 24, 2024. 2 pages.
Calton, M., Preclinical Characterization of 4D-175, a Novel AAV-based Investigational Intravitreal Gene Therapy for Geographic Atrophy. ARVO Annual Meeting, Seattle, WA. May 5-9, 2024. Abstract. 5 pages.
4D Molecular Therapeutics, Form 10-K—Annual Report, United States Securities and Exchange Commission, filed Mar. 25, 2021, pp. 1-211 [online], [PDF], [retrieved on Jul. 10, 2024]. Retrieved from the Internet <https://ir.4dmoleculartherapeutics.com/static-files/5f413acb-8ef2-4c36-adb8-d7390904d7b5>.
4D Molecular Therapeutics, Form 10-Q—Quarterly Report, United States Securities and Exchange Commission, filed May 13, 2021, pp. 1-105 [online], [PDF], [retrieved on Jul. 10, 2024]. Retrieved from the Internet <https://ir.4dmoleculartherapeutics.com/static-files/3ceccf8b-2d50-4306-8389-87429238e767>.
4D Molecular Therapeutics, Form 10-Q—Quarterly Report, United States Securities and Exchange Commission, filed Aug. 12, 2021, pp. 1-106 [online], [PDF], [retrieved on Jul. 10, 2024]. Retrieved from the Internet <https://ir.4dmoleculartherapeutics.com/static-files/07d08224-2a9e-4483-8bea-c1f22433392c>.
4D Molecular Therapeutics, Form 10-Q—Quarterly Report, United States Securities and Exchange Commission, filed Nov. 10, 2021, pp. 1-120 [online], [PDF], [retrieved on Jul. 10, 2024]. Retrieved from the Internet <https://ir.4dmoleculartherapeutics.com/static-files/b94c1f44-afd3-415f-a50f-fe714ab3e4a5>.
4D Molecular Therapeutics, Form 10-K—Annual Report, United States Securities and Exchange Commission, filed Mar. 28, 2022, pp. 1-192 [online], [PDF], [retrieved on Jul. 10, 2024]. Retrieved from the Internet <https://ir.4dmoleculartherapeutics.com/static-files/5eb5823c-fcc9-4c38-b2ee-2efafc6246d3>.
4D Molecular Therapeutics, Form 10-Q—Quarterly Report, United States Securities and Exchange Commission, filed May 12, 2022, pp. 1-113[online], [PDF], [retrieved on Jul. 10, 2024]. Retrieved from the Internet <https://ir.4dmoleculartherapeutics.com/static-files/3e263d69-71db-4be7-8a89-7a5292dc96ff>.
4D Molecular Therapeutics, Form 10-Q—Quarterly Report, United States Securities and Exchange Commission, filed Aug. 11, 2022, pp. 1-110 [online], [PDF], [retrieved on Jul. 10, 2024]. Retrieved from the Internet <https://ir.4dmoleculartherapeutics.com/static-files/62b4af73-26ce-4226-8c1c-6318786d3763>.
4D Molecular Therapeutics, Form 10-Q—Quarterly Report, United States Securities and Exchange Commission, filed Nov. 8, 2022, pp. 1-113 [online], [PDF], [retrieved on Jul. 10, 2024]. Retrieved from the Internet <https://ir.4dmoleculartherapeutics.com/static-files/f7dce850-a277-4f6f-a9f6-cfb5a07d1542>.
4D Molecular Therapeutics, Form 10-K—Annual Report, United States Securities and Exchange Commission, filed Mar. 15, 2023, pp. 1-177 [online], [PDF], [retrieved on Jul. 10, 2024]. Retrieved from the Internet <https://ir.4dmoleculartherapeutics.com/static-files/d340f7e9-d59e-4a57-861a-dc11cfle30a3>.
4D Molecular Therapeutics, Form 10-Q—Quarterly Report, United States Securities and Exchange Commission, filed May 10, 2023, pp. 1-111 [online], [PDF], [retrieved on Jul. 10, 2024]. Retrieved from the Internet <https://ir.4dmoleculartherapeutics.com/static-files/381d8260-1cd0-4833-b94c-ecd1c0f00d84>.
4D Molecular Therapeutics, Form 10-Q—Quarterly Report, United States Securities and Exchange Commission, filed Aug. 9, 2023, pp. 1-111 [online], [PDF], [retrieved on Jul. 10, 2024]. Retrieved from the Internet <https://ir.4dmoleculartherapeutics.com/static-files/b807bc69-3485-4941-80ab-6d940ff28293>.
4D Molecular Therapeutics, Form 10-Q—Quarterly Report, United States Securities and Exchange Commission, filed Nov. 9, 2023, pp. 1-172 [online], [PDF], [retrieved on Jul. 10, 2024]. Retrieved from

(56) References Cited

OTHER PUBLICATIONS the Internet <https://ir.4dmoleculartherapeutics.com/static-files/db121365-ccba-47f4-96d5-546d9769b933>.
4D Molecular Therapeutics, Form 10-K—Annual Report, United States Securities and Exchange Commission, filed Feb. 29, 2024, pp. 1-216 [online], [PDF], [retrieved on Jul. 10, 2024]. Retrieved from the Internet <https://ir.4dmoleculartherapeutics.com/static-files/b6f2901d-c37f-4020-bc23-400dd06bd492>.
4D Molecular Therapeutics, Form 10K (ARS)—Annual Report, United States Securities and Exchange Commission, filed Apr. 10, 2024, pp. 1-164 [online], [PDF], [retrieved on Jul. 10, 2024]. Retrieved from the Internet <https://ir.4dmoleculartherapeutics.com/static-files/030bd0c6-64d7-4ce5-8229-4b5dbd907408>.
4D Molecular Therapeutics, Form 10-Q—Quarterly Report, United States Securities and Exchange Commission, filed May 9, 2024, pp. 1-111 [online], [PDF], [retrieved on Jul. 10, 2024]. Retrieved from the Internet <https://ir.4dmoleculartherapeutics.com/static-files/b80820a3-690c-42b6-bba4-369069ba2964>.

* cited by examiner

FIG 1A

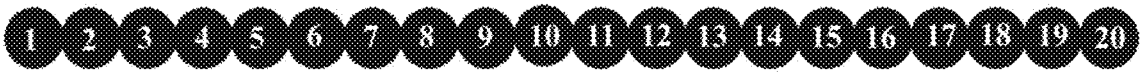

FIG 1B

```
Atgagacttctagcaaagattatttgccttatgttatgggctatttgtgtagcagaagat signal
 M  R  L  L  A  K  I  I  C  L  M  L  W  A  I  C  V  A  E  D  peptide
tgcaatgaacttcctccaagaagaaatacagaaattctgacaggttcctggtctgaccaa
 C  N  E  L  P  P  R  K  N  T  E  I  L  T  G  S  W  S  D  Q
Acatatccagaaggcacccaggctatctataaatgccgccctggatatagatctcttgga   SCR1
 T  Y  P  E  G  T  Q  A  I  Y  K  C  R  P  G  Y  R  S  L  G
aatataataatggtatgcaggaagggagaatgggttgctcttaatccattaaggaaatgt
 N  I  I  M  V  C  R  K  G  E  W  V  A  L  N  P  L  R  K  C
cagaaaaggccctgtggacatcctggagatactccttttggtacttttacccttacagga
 Q  K  R  P  C  G  H  P  G  D  T  P  F  G  T  F  T  L  T  G
Ggaaatgtgtttgaatatggtgtaaaagctgtgtatacatgtaatgaggggtatcaattg   SCR2
 G  N  V  F  E  Y  G  V  K  A  V  Y  T  C  N  E  G  Y  Q  L
ctaggtgagattaattaccgtgaatgtgacacagatggatggaccaatgatattcctata
 L  G  E  I  N  Y  R  E  C  D  T  D  G  W  T  N  D  I  P  I
tgtgaagttgtgaagtgtttaccagtgacagcaccagagaatggaaaaattgtcagtagt
 C  E  V  V  K  C  L  P  V  T  A  P  E  N  G  K  I  V  S  S
Gcaatggaaccagatcgggaataccattttggacaagcagtacggtttgtatgtaactca   SCR3
 A  M  E  P  D  R  E  Y  H  F  G  Q  A  V  R  F  V  C  N  S
ggctacaagattgaaggagatgaagaaatgcattgttcagacgatggtttttggagtaaa
 G  Y  K  I  E  G  D  E  E  M  H  C  S  D  D  G  F  W  S  K
gagaaaccaaagtgtgtggaaatttcatgcaaatccccagatgttataaatggatctcct
 E  K  P  K  C  V  E  I  S  C  K  S  P  D  V  I  N  G  S  P
Atatctcagaagattatttataaggagaatgaacgatttcaatataaatgtaacatgggt   SCR4
 I  S  Q  K  I  I  Y  K  E  N  E  R  F  Q  Y  K  C  N  M  G
tatgaatacagtgaaagaggagatgctgtatgcactgaatctggatggcgtccgttgcct
 Y  E  Y  S  E  R  G  D  A  V  C  T  E  S  G  W  R  P  L  P
tcatgtgaagaaaaatcatgtgataatccttatattccaaatggtgactactcaccttta
 S  C  E  E  K  S  C  D  N  P  Y  I  P  N  G  D  Y  S  P  L
Aggattaaacacagaactggagatgaaatcacgtaccagtgtagaaatggtttttatcct
 R  I  K  H  R  T  G  D  E  I  T  Y  Q  C  R  N  G  F  Y  P   SCR5
gcaacccggggaaatacagccaaatgcacaagtactggctggatacctgctccgagatgt
 A  T  R  G  N  T  A  K  C  T  S  T  G  W  I  P  A  P  R  C
accttgaaaccttgtgattatccagacattaaacatggaggtctatatcatgagaatatg
 T  L  K  P  C  D  Y  P  D  I  K  H  G  G  L  Y  H  E  N  M
Cgtagaccatactttccagtagctgtaggaaaatattactcctattactgtgatgaacat
 R  R  P  Y  F  P  V  A  V  G  K  Y  Y  S  Y  Y  C  D  E  H   SCR6
```

FIG 1C tttgagactccgtcaggaagttactgggatcacattcattgcacacaagatggatggtcg
F E T P S G S Y W D H I H C T Q D G W S
ccagcagtaccatgcctcagaaaatgttattttccttatttggaaaatggatataatcaa
P A V P C L R K C Y F P Y L E N G Y N Q
Aattatggaagaaagtttgtacagggtaaatctatagacgttgcctgccatcctggctac
N Y G R K F V Q G K S I D V A C H P G Y SCR7
gctcttccaaaagcgcagaccacagttacatgtatggagaatggctggtctcctactccc
A L P K A Q T T V T C M E N G W S P T P
agatgcatccgtgtcaaaacatgttccaaatcaagtatagatattgagaatgggtttatt
R C I R V K T C S K S S I D I E N G F I
Tctgaatctcagtatacatatgccttaaaagaaaaagcaaaatatcaatgcaaactagga
S E S Q Y T Y A L K E K A K Y Q C K L G SCR8
tatgtaacagcagatggtgaaacatcaggatcaattacatgtgggaaagatggatggtca
Y V T A D G E T S G S I T C G K D G W S
gctcaacccacgtgcattaaatcttgtgatatcccagtatttatgaatgccagaactaaa
A Q P T C I K S C D I P V F M N A R T K
Aatgacttcacatggtttaagctgaatgacacattggactatgaatgccatgatggttat
N D F T W F K L N D T L D Y E C H D G Y SCR9
gaaagcaatactggaagcaccactggttccatagtgtgtggttacaatggttggtctgat
E S N T G S T T G S I V C G Y N G W S D
ttacccatatgttatgaaagagaatgcgaacttcctaaaatagatgtacacttagttcct
L P I C Y E R E C E L P K I D V H L V P
gatcgcaagaaagaccagtataaagttggagaggtgttgaaattctcctgcaaaccagga
D R K K D Q Y K V G E V L K F S C K P G SCR10
tttacaatagttggacctaattccgttcagtgctaccactttggattgtctcctgacctc
F T I V G P N S V Q C Y H F G L S P D L
ccaatatgtaaagagcaagtacaatcatgtggtccacctcctgaactcctcaatggaaat
P I C K E Q V Q S C G P P P E L L N G N
Gttaaggaaaaaacgaaagaagaatatggacacagtgaagtggtggaatattattgcaat
V K E K T K E E Y G H S E V V E Y Y C N SCR11
cctagatttctaatgaagggacctaataaaattcaatgtgttgatggagagtggacaact
P R F L M K G P N K I Q C V D G E W T T
ttaccagtgtgtattgtggaggagagtacctgtggagatatacctgaacttgaacatggc
L P V C I V E E S T C G D I P E L E H G
Tgggcccagctttcttcccctccttattactatggagattcagtggaattcaattgctca
W A Q L S S P P Y Y Y G D S V E F N C S SCR12
gaatcatttacaatgattggacacagatcaattacgtgtattcatggagtatggacccaa
E S F T M I G H R S I T C I H G V W T Q

FIG 1D cttccccagtgtgtggcaatagataaacttaagaagtgcaaatcatcaaatttaattata
L P Q C V A I D K L K K C K S S N L I T Cttgaggaacatttaaaaaacaagaaggaattcgatcataattctaacataaggtacaga
L E E H L K N K K E F D H N S N I R Y R SCR13 tgtagaggaaaagaaggatggatacacacagtctgcataaatggaagatgggatccagaa
C R G K E G W I H T V C I N G R W D P E gtgaactgctcaatggcacaaatacaattatgcccacctccacctcagattcccaattct
V N C S M A Q I Q L C P P P P Q I P N S Cacaatatgacaaccacactgaattatcgggatggagaaaaagtatctgttctttgccaa
H N M T T T L N Y R D G E K V S V L C Q SCR14 gaaaattatctaattcaggaaggagaagaaattacatgcaaagatggaagatggcagtca
E N Y L I Q E G E E I T C K D G R W Q S ataccactctgtgttgaaaaaattccatgttcacaaccacctcagatagaacacggaacc
I P L C V E K I P C S Q P P Q I E H G T Attaattcatccaggtcttcacaagaaagttatgcacatgggactaaattgagttatact
I N S S R S S Q E S Y A H G T K L S Y T SCR15 tgtgagggtggtttcaggatatctgaagaaaatgaaacaacatgctacatgggaaaatgg
C E G G F R I S E E N E T T C Y M G K W agttctccacctcagtgtgaaggccttccttgtaaatctccacctgagatttctcatggt
S S P P Q C E G L P C K S P P E I S H G Gttgtagctcacatgtcagacagttatcagtatggagaagaagttacgtacaaatgtttt
V V A H M S D S Y Q Y G E E V T Y K C F SCR16 gaaggtttggaattgatgggcctgcaattgcaaaatgcttaggagaaaaatggtctcac
E G F G I D G P A I A K C L G E K W S H cctccatcatgcataaaaacagattgtctcagtttacctagctttgaaaatgccataccc
P P S C I K T D C L S L P S F E N A I P Atgggagagaagaaggatgtgtataaggcgggtgagcaagtgacttacacttgtgcaaca
M G E K K D V Y K A G E Q V T Y T C A T SCR17 tattacaaaatggatggagccagtaatgtaacatgcattaatagcagatggacaggaagg
Y Y K M D G A S N V T C I N S R W T G R ccaacatgcagagacacctcctgtgtgaatccgcccacagtacaaaatgcttatatagtg
P T C R D T S C V N P P T V Q N A Y I V Tcgagacagatgagtaaatatccatctggtgagagagtacgttatcaatgtaggagccct
S R Q M S K Y P S G E R V R Y Q C R S P SCR18

FIG 1E

Acttcattcccgttgtcagtatatgctccagcttcatcagttgagtaccaatgccagaac
T S F P L S V Y A P A S S V E Y Q C Q N SCR19
ttgtatcaacttgagggtaacaagcgaataacatgtagaaatggacaatggtcagaacca
L Y Q L E G N K R I T C R N G Q W S E P
ccaaaatgcttacatccgtgtgtaatatcccgagaaattatggaaaattataacatagca
P K C L H P C V I S R E I M E N Y N I A
Ttaaggtggacagccaaacagaagctttattcgagaacaggtgaatcagttgaatttgtg
L R W T A K Q K L Y S R T G E S V E F V SCR20
tgtaaacggggatatcgtctttcatcacgttctcacacattgcgaacaacatgttgggat
C K R G Y R L S S R S H T L R T T C W D
gggaaactggagtatccaacttgtgcaaaaagatag
G K L E Y P T C A K R ~

FIG 2A

FIG 2B

Atgagacttctagcaaagattatttgccttatgttatgggctatttgtgtagcagaagat SignalPeptide
M R L L A K I I C L M L W A I C V A E D tgcaatgaacttcctccaagaagaaatacagaaattctgacaggttcctggtctgaccaa
C N E L P P R R N T E I L T G S W S D Q Acatatccagaaggcacccaggctatctataaatgccgccctggatatagatctcttgga SCR1
T Y P E G T Q A I Y K C R P G Y R S L G aatataataatggtatgcaggaagggagaatgggttgctcttaatccattaaggaaatgt
N I I M V C R K G E W V A L N P L R K C cagaaaaggccctgtggacatcctggagatactcctttggtactttaccctttacagga
Q K R P C G H P G D T P F G T F T L T G Ggaaatgtgtttgaatatggtgtaaaagctgtgtatacatgtaatgaggggtatcaattg
G N V F E Y G V K A V Y T C N E G Y Q L SCR2 ctaggtgagattaattaccgtgaatgtgacacagatggatggaccaatgatattcctata
L G E I N Y R E C D T D G W T N D I P I tgtgaagttgtgaagtgtttaccagtgacagcaccagagaatggaaaaattgtcagtagt
C E V V K C L P V T A P E N G K I V S S Gcaatggaaccagatcgggaataccattttggacaagcagtacggtttgtatgtaactca
A M E P D R E Y H F G Q A V R F V C N S SCR3 ggctacaagattgaaggagatgaagaaatgcattgttcagacgatggtttttggagtaaa
G Y K I E G D E E M H C S D D G F W S K gagaaaccaaagtgtgtggaaatttcatgcaaatccccagatgttataaatggatctcct
E K P K C V E I S C K S P D V I N G S P Atatctcagaagattatttataaggagaatgaacgatttcaatataaatgtaacatgggt
I S Q K I I Y K E N E R F Q Y K C N M G SCR4 tatgaatacagtgaaagaggagatgctgtatgcactgaatctggatggcgtccgttgcct
Y E Y S E R G D A V C T E S G W R P L P Tcatgtgaagaaaaatca
S C E E K S accttgaaaccttgtgattatccagacattaaacatggaggtctatatcatgagaatatg
T L K P C D Y P D I K H G G L Y H E N M cgtagaccatactttccagtagctgtaggaaaatattactcctattactgtgatgaacat
R R P Y F P V A V G K Y Y S Y Y C D E H SCR6 tttgagactccgtcaggaagttactgggatcacattcattgcacacaagatggatggtcg
F E T P S G S Y W D H I H C T Q D G W S

FIG 2C ccagcagtaccatgcctcagaaaatgttattttccttatttggaaaatggatataatcaa

P A V P C L R K C Y F P Y L E N G Y N Q

Aattatggaagaaagtttgtacagggtaaatctatagacgttgcctgccatcctggctac

N Y G R K F V Q G K S I D V A C H P G Y SCR7 gctcttccaaaagcgcagaccacagttacatgtatggagaatggctggtctcctactccc

A L P K A Q T T V T C M E N G W S P T P agatgcatccgtgtcaaaacatgttccaaatcaagtatagatattgagaatgggtttatt

R C I R V K T C S K S S I D I E N G F I

Tctgaatctcagtatacatatgccttaaaagaaaaagcaaaatatcaatgcaaactagga

S E S Q Y T Y A L K E K A K Y Q C K L G SCR8 tatgtaacagcagatggtgaaacatcaggatcaattacatgtgggaaagatggatggtca

Y V T A D G E T S G S I T C G K D G W S gctcaacccacgtgcattaaatctaaagattctacaggaaaatgtgggcccccctccacct

A Q P T C I K S K D S T G K C G P P P P attgacaatggggacattActtcattcccgttgtcagtatatgctccagcttcatcagtt

I D N G D I T S F P L S V Y A P A S S V gagtaccaatgccagaacttgtatcaacttgagggtaacaagcgaataacatgtagaaat

E Y Q C Q N L Y Q L E G N K R I T C R N SCR19 ttgtatcaacttgagggtaacaagcgaataacatgtagaaatggacaatggtcagaacca

L Y Q L E G N K R I T C R N G Q W S E P ccaaaatgcttacatccgtgtgtaatatcccgagaaattatggaaaattataacatagca

P K C L H P C V I S R E I M E N Y N I A

Ttaaggtggacagccaaacagaagctttattcgagaacaggtgaatcagttgaatttgtg

L R W T A K Q K L Y S R T G E S V E F V SCR20 tgtaaacggggatatcgtctttcatcacgttctcacacattgcgaacaacatgttgggat

C K R G Y R L S S R S H T L R T T C W D gggaaactggagtatccaacttgtgcaaaaagatag

```
1 GGACGTTGTGAACAGAGTTAGCTGGTAAATGTCCTCTTAAAAGATCCAAAAA   52
atgagactTctagcaaagattatttgccttatgttatgggctatttgtgtagcagaagattgcaatgaac   122
ttcctccaagaagaaatacagaaattctgacaggttcctggtctgaccaaacatatccagaaggcaccca   192
Ggctatctataaatgccgccctggatatagatctcttggaaatataataatggtatgcaggaagggagaa   262
Tgggttgctcttaatccattaaggaaatgtcagaaaaggccctgtggacatcctggagatactccttttg   332
gtacttttacccttacaggaggaaatgtGtttgaatatggtgtaaaagctgtgtatacatgtaatgaggg   402
gtatcaattgctaggtgaGattaattaccgtgaatgtgacacagatggatggaccaatgatattcctata   472
tgtgaagttgtgaagtgtttaccagtgacagcaccagagaatggaaaaattgtcagtagtgcaatggaac   542
cagatcgggaataccattttggacaagcagtacggtttgtatgtaactcaggctacaagattgaaggaga   612
tgaagaaatgcattgttcagacgatggtttttggagtaaagagaaaccaaagtgtgtggaaatttcatgc   682
aaatccccagatgttataaatggatctcctatatctcagaagattatttataaggagaatgaacgatttc   752
aatataaatgtaacatgggttatgaatacagtgaaagaggagatgctgtatgcactgaatctggatggcg   822
tccgttgccttcatgtgaagaaaaatcaaccttgaaaccttgtgattatccagacattaaacatggaggt   892
ctatatcatgagaatatgcgtagaccatactttccagtagctgtaggaaaatattactcctattactgtg   962
atgaacattttgagactccgtcaggaagttactgggatcacattcattgcacacaagatggatggtcgcc 1032
agcagtaccatgcctcagaaaatgttattttccttatttggaaaatggatataatcaaaattatggaaga 1102
aagtttgtacagggtaaatctatagacgttgcctgccatcctggctacgctcttccaaaagcgcagacca 1172
cagttacatgtatggagaatggctggtcTcctactcccagatgcatccgtgtcaaaacatgttccaaatc 1242
```

FIG 3B

```
Aagtatagatattgagaatgggtttatttctgaatctcagtatacatatgccttaaaagaaaaagcgaaa  1312
Tatcaatgcaaactaggatatgtaacagcagatggtgaaacatcaggatcaattagatgtgggaaagatg  1382
Gatggtcagctcaacccacgtgcattaaatctaaagattctacaggaaaatgtgggccccctccacctat  1452
Tgacaatggggacattacttcattcccgttgtcagtatatgctccagcttcatcagttgagtaccaatgc  1522
Cagaacttgtatcaacttgagggtaacaagcgaataacatgtagaaatggacaatggtcagaaccaccaa  1592
Aatgcttacatccgtgtgtaatatcccgagaaattatggaaaattataacatagcattaaggtggacagc  1662
Caaacagaagctttattcgagaacaggtgaatcagttgaatttgtgtgtaaacggggatatcgtctttca  1732
Tcacgttctcacacattgcgaacaacatgttgggatgggaaactggagtatccaacttgtgcaaaaagat  1802
agAATCAATCATAAAGTGCACACCTTTATTCAGAACTTTAGTATTAAATCAGTTCTCAATTTCATTTTTT  1872
ATGTATTGTTTTACTCCTTTTTATTCATACGTAAAATTTTGGATTAATTTGTGAAAATGTAATTATAAGC  1942
TGAGACCGGTGGCTCTCTTCTTAAAAGCACCATATTAAATCCTGGAAAACTAAAAAAAAAAAAAAAAAAA  2012
AAAAAAAAAAAAAAAAAAAAAAAAAAAAAAAAAAAAAAAAAAAAAAAAAAAAAAAA 2068
```

FIG 4 hfH1-4.678.19-20 protein amino acid sequence:

<u>MRLLAKIICLMLWAICVA</u>EDCNELPPRRNTEILTGSWSDQTYPEGTQAIYKCRPGYRSLG
NIIMVCRKGEWVALNPLRKCQKRPCGHPGDTPFGTFTLTGGNVFEYGVKAVYTCNEGY
QLLGEINYRECDTDGWTNDIPICEVVKCLPVTAPENGKIVSSAMEPDREYHFGQAVRFVC
NSGYKIEGDEEMHCSDDGFWSKEKPKCVEISCKSPDVINGSPISQKIIYKENERFQYKCN
MGYEYSERGDAVCTESGWRPLPSCEEKSTLKPCDYPDIKHGGLYHENMRRPYFPVAVG
KYYSYYCDEHFETPSGSYWDHIHCTQDGWSPAVPCLRKCYFPYLENGYNQNHGRKFVQ
GKSIDVACHPGYALPKAQTTVTCMENGWSPTPRCIRVKTCSKSSIDIENGFISESQYTYAL
KEKAKYQCKLGYVTADGETSGSIRCGKDGWSAQPTCIKSKDSTGKCGPPPPIDNGDITSF
PLSVYAPASSVEYQCQNLYQLEGNKRITCRNGQWSEPPKCLHPCVISREIMENYNIALRW
TAKQKLYSRTGESVEFVCKRGYRLSSRSHTLRTTCWDGKLEYPTCAKR

FIG 5A

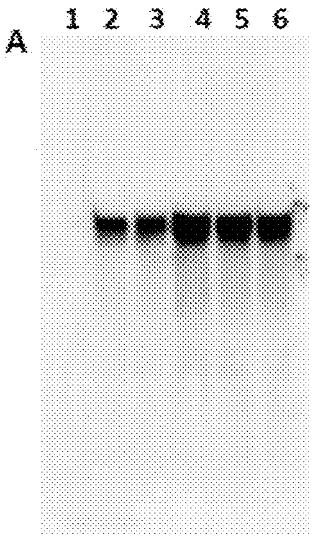

1:Con
2:pCMV Sport6- 1
3:pCMV Sport6-2
4:pCBARBG-1
5:pCBARBG-2
6:pCBARBG-3

FIG 5B

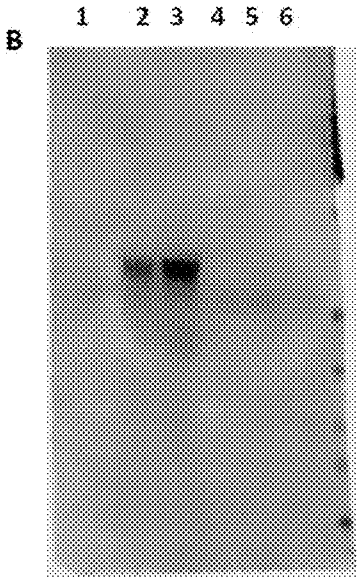

1:Con
2:pCBARBG-1
3:pAAV Cl1
4:pAAV Cl2
5:pAAV Cl3
6:pAAV Cl4

1: hfH 0.5ug
2: hfH 1-4.678.19-20 0.5ug(prep1)
3: hfH 1-4.678.19-20 0.5ug(prep2)
4: hfH 0.25ug
5: hfH 1-4.678.19-20 0.25ug(prep1)
6. hfH 1-4.678.19-20 0.25ug(prep2)
7: hC3b +fI Control

FIG 12B

Atgagacttctagcaaagattatttgccttatgttatgggctatttgtgtagcagaagat SignalPeptide
M R L L A K I I C L M L W A I C V A E D (shaded)
tgcaatgaacttcctccaagaagaaatacagaaattctgacaggttcctggtctgaccaa
C N E L P P R R N T E I L T G S W S D Q
acatatccagaaggcacccaggctatctataaatgccgccctggatatagatctcttgga SCR1
T Y P E G T Q A I Y K C R P G Y R S L G
aatataataatggtatgcaggaagggagaatgggttgctcttaatccattaaggaaatgt
N I I M V C R K G E W V A L N P L R K C
cagaaaaggccctgtggacatcctggagatactcctttttggtacttttacccttacagga
Q K R P C G H P G D T P F G T F T L T G
ggaaatgtgtttgaatatggtgtaaaagctgtgtatacatgtaatgaggggtatcaattg
G N V F E Y G V K A V Y T C N E G Y Q L SCR2
ctaggtgagattaattaccgtgaatgtgacacagatggatggaccaatgatattcctata
L G E I N Y R E C D T D G W T N D I P I
tgtgaagttgtgaagtgtttaccagtgacagcaccagagaatggaaaaattgtcagtagt
C E V V K C L P V T A P E N G K I V S S
gcaatggaaccagatcgggaataccattttggacaagcagtacggtttgtatgtaactca
A M E P D R E Y H F G Q A V R F V C N S SCR3
ggctacaagattgaaggagatgaagaaatgcattgttcagacgatggtttttggagtaaa
G Y K I E G D E E M H C S D D G F W S K
gagaaaccaaagtgtgtggaaatttcatgcaaatccccagatgttataaatggatctcct
E K P K C V E I S C K S P D V I N G S P
atatctcagaagattatttataaggagaatgaacgatttcaatataaatgtaacatgggt
I S Q K I I Y K E N E R F Q Y K C N M G SCR4
tatgaatacagtgaaagaggagatgctgtatgcactgaatctggatggcgtccgttgcct
Y E Y S E R G D A V C T E S G W R P L P
tcatgtgaagaaaaatcaaccttgaaaccttgtgattatccagacattaaacatggaggt
S C E E K S T L K P C D Y P D I K H G G
ctatatcatgagaatatgcgtagaccatactttccagtagctgtaggaaaatattactcc
L Y H E N M R R P Y F P V A V G K Y Y S SCR6
tattactgtgatgaacattttgagactccgtcaggaagttactgggatcacattcattgc
Y Y C D E H F E T P S G S Y W D H I H C
acacaagatggatggtcgccagcagtaccatgcctcagaaaatgttattttccttatttg
T Q D G W S P A V P C L R K C Y F P Y L
gaaaatggatataatcaaaattatggaagaaagtttgtacagggtaaatctatagacgtt
E N G Y N Q N Y G R K F V Q G K S I D V SCR7
gcctgccatcctggctacgctcttccaaaagcgcagaccacagttacatgtatggagaat
A C H P G Y A L P K A Q T T V T C M E N
ggctggtctcctactcccagatgcatccgtgtcaaaacatgttccaaatcaagtatagat
G W S P T P R C I R V K T C S K S S I D
attgagaatgggtttatttctgaatctcagtatacatatgccttaaaagaaaaagcaaaa
I E N G F I S E S Q Y T Y A L K E K A K SCR8
tatcaatgcaaactaggatatgtaacagcagatggtgaaacatcaggatcaattacatgt
Y Q C K L G Y V T A D G E T S G S I T C
gggaaagatggatggtcagctcaacccacgtgcattaaatctataaaaacagattgtctc
G K D G W S A Q P T C I K S I K T D C L

FIG 12C agtttacctagctttgaaaatgccatacccatgggagagaagaaggatgtgtataaggcg
S L P S F E N A I P M G E K K D V Y K A
ggtgagcaagtgacttacacttgtgcaacatattacaaaatggatggagccagtaatgta SCR17
G E Q V T Y T C A T Y Y K M D G A S N V
acatgcattaatagcagatggacaggaaggccaacatgcagagacacctcctgtgtgaat
T C I N S R W T G R P T C R D T S C V N
ccgcccacagtacaaaatgcttatatagtgtcgagacagatgagtaaatatccatctggt
P P T V Q N A Y I V S R Q M S K Y P S G
gagagagtacgttatcaatgtaggagcccttatgaaatgtttggggatgaagaagtgatg SCR18
E R V R Y Q C R S P Y E M F G D E E V M
tgtttaaatggaaactggacggaaccacctcaatgcaaagattctacaggaaaatgtggg
C L N G N W T E P P Q C K D S T G K C G
ccccctccacctattgacaatggggacattacttcattcccgttgtcagtatatgctcca
P P P P I D N G D I T S F P L S V Y A P SCR19
gcttcatcagttgagtaccaatgccagaacttgtatcaacttgagggtaacaagcgaata
A S S V E Y Q C Q N L Y Q L E G N K R I
acatgtagaaatggacaatggtcagaaccaccaaaatgcttacatccgtgtgtaatatcc
T C R N G Q W S E P P K C L H P C V I S
cgagaaattatggaaaattataacatagcattaaggtggacagccaaacagaagctttat
R E I M E N Y N I A L R W T A K Q K L Y
tcgagaacaggtgaatcagttgaatttgtgtgtaaacggggatatcgtctttcatcacgt SCR20
S R T G E S V E F V C K R G Y R L S S R
tctcacacattgcgaacaacatgttgggatgggaaactggagtatccaacttgtgcaaaa
S H T L R T T C W D G K L E Y P T C A K
agatag
R -

FIG 13

GGACGTTGTGAACAGAGTTAGCTGGTAAATGTCCTCTTAAAAGATCCAAAAAatgagacttctagcaaagat
tatttgccttatgttatgggctatttgtgtagcagaagattgcaatgaacttcctccaagaagaatacaga
aattctgacaggttcctggtctgaccaaacatatccagaaggcacccaggctatctataaatgccgccctgg
atatagatctcttggaaatataataatggtatgcaggaagggagaatgggttgctcttaatccattaaggaa
atgtcagaaaaggccctgtggacatcctggagatactccttttggtacttttacccttacaggaggaaatgt
gtttgaatatggtgtaaaagctgtgtatacatgtaatgaggggtatcaattgctaggtgagattaattaccg
tgaatgtgacacagatggatggaccaatgatattcctatatgtgaagttgtgaagtgtttaccagtgacagc
accagagaatggaaaaattgtcagtagtgcaatggaaccagatcgggaataccattttggacaagcagtacg
gtttgtatgtaactcaggctacaagattgaaggagatgaagaaatgcattgttcagacgatggtttttggag
taaagagaaaccaaagtgtgtggaaatttcatgcaaatccccagatgttataaatggatctcctatatctca
gaagattatttataaggagaatgaacgatttcaatataaatgtaacatgggttatgaatacagtgaaagagg
agatgctgtatgcactgaatctggatggcgtccgttgccttcatgtgaagaaaaatcaaccttgaaacctg
tgattatccagacattaaacatggaggtctatatcatgagaatatgcgtagaccatactttccagtagctgt
aggaaaatattactcctattactgtgatgaacattttgagactccgtcaggaagttactgggatcacattca
ttgcacacaagatggatggtcgccagcagtaccatgcctcagaaaatgttattttccttatttggaaaatgg
atataatcaaaattatggaagaaagtttgtacagggtaaatctatagacgttgcctgccatcctggctacgc
tcttccaaaagcgcagaccacagttacatgtatggagaatggctggtctcctactcccagatgcatccgtgt
caaaacatgttccaaatcaagtatagatattgagaatgggtttatttctgaatctcagtatacatatgcctt
aaaagaaaaagcaaaatatcaatgcaaactaggatatgtaacagcagatggtgaaacatcaggatcaattac
atgtgggaaagatggatggtcagctcaacccacgtgcattaaatctataaaaacagattgtctcagtttacc
tagctttgaaaatgccatacccatgggagagaagaaggatgtgtataaggcgggtgagcaagtgacttacac
ttgtgcaacatattacaaaatggatggagccagtaatgtaacatgcattaatagcagatggacaggaaggcc
aacatgcagagacacctcctgtgtgaatccgcccacagtacaaaatgcttatatagtgtcgagacagatgag
taaatatccatctggtgagagagtacgttatcaatgtaggagcccttatgaaatgtttggggatgaagaagt
gatgtgtttaaatggaaactggacggaaccacctcaatgcaaagattctacaggaaaatgtgggccccctcc
acctattgacaatggggacattacttcattcccgttgtcagtatatgctccagcttcatcagttgagtacca
atgccagaacttgtatcaacttgagggtaacaagcgaataacatgtagaaatggacaatggtcagaaccacc
aaaatgcttacatccgtgtgtaatatcccgagaaattatggaaaattataacatagcattaaggtggacagc
caaacagaagctttattcgagaacaggtgaatcagttgaatttgtgtgtaaacggggatatcgtctttcatc
acgttctcacacattgcgaacaacatgttgggatgggaaactggagtatccaacttgtgcaaaaagatag

FIG 14

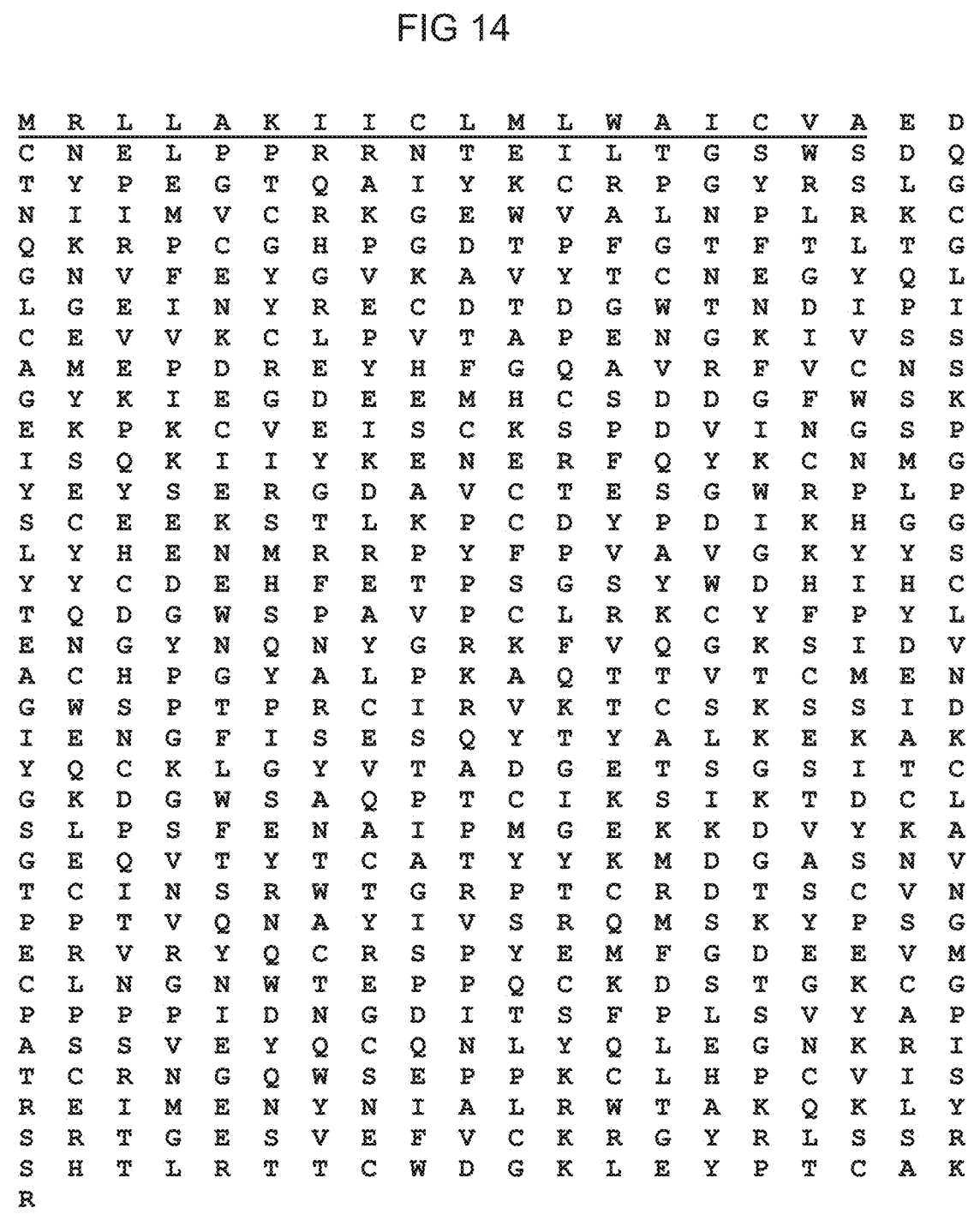

| | | | | | | | | | | | | | | | | | | | |
|---|---|---|---|---|---|---|---|---|---|---|---|---|---|---|---|---|---|---|---|
| M | R | L | L | A | K | I | I | C | L | M | L | W | A | I | C | V | A | E | D |
| C | N | E | L | P | P | R | R | N | T | E | I | L | T | G | S | W | S | D | Q |
| T | Y | P | E | G | T | Q | A | I | Y | K | C | R | P | G | Y | R | S | L | G |
| N | I | I | M | V | C | R | K | G | E | W | V | A | L | N | P | L | R | K | C |
| Q | K | R | P | C | G | H | P | G | D | T | P | F | G | T | F | T | L | T | G |
| G | N | V | F | E | Y | G | V | K | A | V | Y | T | C | N | E | G | Y | Q | L |
| L | G | E | I | N | Y | R | E | C | D | T | D | G | W | T | N | D | I | P | I |
| C | E | V | V | K | C | L | P | V | T | A | P | E | N | G | K | I | V | S | S |
| A | M | E | P | D | R | E | Y | H | F | G | Q | A | V | R | F | V | C | N | S |
| G | Y | K | I | E | G | D | E | E | M | H | C | S | D | D | G | F | W | S | K |
| E | K | P | K | C | V | E | I | S | C | K | S | P | D | V | I | N | G | S | P |
| I | S | Q | K | I | I | Y | K | E | N | E | R | F | Q | Y | K | C | N | M | G |
| Y | E | Y | S | E | R | G | D | A | V | C | T | E | S | G | W | R | P | L | P |
| S | C | E | E | K | S | T | L | K | P | C | D | Y | P | D | I | K | H | G | G |
| L | Y | H | E | N | M | R | R | P | Y | F | P | V | A | V | G | K | Y | Y | S |
| Y | Y | C | D | E | H | F | E | T | P | S | G | S | Y | W | D | H | I | H | C |
| T | Q | D | G | W | S | P | A | V | P | C | L | R | K | C | Y | F | P | Y | L |
| E | N | G | Y | N | Q | N | Y | G | R | K | F | V | Q | G | K | S | I | D | V |
| A | C | H | P | G | Y | A | L | P | K | A | Q | T | T | V | T | C | M | E | N |
| G | W | S | P | T | P | R | C | I | R | V | K | T | C | S | K | S | S | I | D |
| I | E | N | G | F | I | S | E | S | Q | Y | T | Y | A | L | K | E | K | A | K |
| Y | Q | C | K | L | G | Y | V | T | A | D | G | E | T | S | G | S | I | T | C |
| G | K | D | G | W | S | A | Q | P | T | C | I | K | S | I | K | T | D | C | L |
| S | L | P | S | F | E | N | A | I | P | M | G | E | K | K | D | V | Y | K | A |
| G | E | Q | V | T | Y | T | C | A | T | Y | Y | K | M | D | G | A | S | N | V |
| T | C | I | N | S | R | W | T | G | R | P | T | C | R | D | T | S | C | V | N |
| P | P | T | V | Q | N | A | Y | I | V | S | R | Q | M | S | K | Y | P | S | G |
| E | R | V | R | Y | Q | C | R | S | P | Y | E | M | F | G | D | E | E | V | M |
| C | L | N | G | N | W | T | E | P | P | Q | C | K | D | S | T | G | K | C | G |
| P | P | P | P | I | D | N | G | D | I | T | S | F | P | L | S | V | Y | A | P |
| A | S | S | V | E | Y | Q | C | Q | N | L | Y | Q | L | E | G | N | K | R | I |
| T | C | R | N | G | Q | W | S | E | P | P | K | C | L | H | P | C | V | I | S |
| R | E | I | M | E | N | Y | N | I | A | L | R | W | T | A | K | Q | K | L | Y |
| S | R | T | G | E | S | V | E | F | V | C | K | R | G | Y | R | L | S | S | R |
| S | H | T | L | R | T | T | C | W | D | G | K | L | E | Y | P | T | C | A | K |
| R | | | | | | | | | | | | | | | | | | | |

FIG 17A

Atggtacagcacagatttctcttggagtcagttggtcccagaaagatccaaattatgaga SignalPeptide

M V Q H R F L L E S V G P R K I Q I M R (Shaded)

Ctgtcagcaagaattatttggcttatattatggactgtttgtgcagcagaagattgtaaa

L S A R I I W L I L W T V C A A E D C K ggtcctcctccaagagaaaattcagaaattctctcaggctcgtggtcagaacaactatat

G P P P R E N S E I L S G S W S E Q L Y SCR1 ccagaaggcacccaggctacctacaaatgccgccctggataccgaacacttggcactatt

P E G T Q A T Y K C R P G Y R T L G T I gtaaaagtatgcaagaatggaaaatgggtggcgtctaacccatccaggatatgtcggaaa

V K V C K N G K W V A S N P S R I C R K

Aagccttgtgggcatcccggagacacaccctttgggtcctttaggctggcagttggatct

K P C G H P G D T P F G S F R L A V G S caatttgagtttggtgcaaaggttgtttatacctgtgatgatgggtatcaactattaggt

Q F E F G A K V V Y T C D D G Y Q L L G SCR2 gaaattgattaccgtgaatgtggtgcagatgggtggatcaatgatattccactatgtgaa

E I D Y R E C G A D G W I N D I P L C E

Gttgtgaagtgtctacctgtgacagaactcgagaatggaagaattgtgagtggtgcagca

V V K C L P V T E L E N G R I V S G A A gaaacagaccaggaatactattttggacaggtggtgcggtttgaatgcaattcaggcttc

E T D Q E Y Y F G Q V V R F E C N S G F SCR3 aagattgaaggacataaggaaattcattgctcagaaaatggcctttggagcaatgaaaag

K I E G H K E I H C S E N G L W S N E K

Ccacgatgtgtggaaattctctgcacaccaccgcgagtggaaaatggagatggtataaat

P R C V E I L C T P P R V E N G D G I N gtgaaaccagtttacaaggagaatgaaagataccactataagtgtaagcatggttatgtg

V K P V Y K E N E R Y H Y K C K H G Y V SCR4 cccaaagaaagaggggatgccgtctgcacaggctctggatggagttctcagcctttctgt

P K E R G D A V C T G S G W S S Q P F C

Gaagaaaagagatgctcacctccttatattctaaatggtatctacacacctcacaggatt

E E K R C S P P Y I L N G I Y T P H R I atacacagaagtgatgatgaaatcagatatgaatgtaattatggcttctatcctgtaact

I H R S D D E I R Y E C N Y G F Y P V T SCR5 ggatcaactgtttcaaagtgtacacccactggctggatccctgttccaagatgtaccttg

G S T V S K C T P T G W I P V P R C T L

Aaaccatgtgaatttccacaattcaaatatggacgtctgtattatgaagagagcctgaga

K P C E F P Q F K Y G R L Y Y E E S L R cccaacttcccagtatctataggaaataagtacagctataagtgtgacaacgggttttca

P N F P V S I G N K Y S Y K C D N G F S SCR6 ccaccttctgggtattcctgggactaccttcgttgcacagcacaagggtgggagcctgaa

P P S G Y S W D Y L R C T A Q G W E P E

Gtcccatgcgtcaggaaatgtgttttccattatgtggagaatggagactctgcatactgg

V P C V R K C V F H Y V E N G D S A Y W

FIG 17B gaaaaagtatatgtgcagggtcagtctttaaaagtccagtgttacaatggctatagtctt
E K V Y V Q G Q S L K V Q C Y N G Y S L SCR7
caaaatggtcaagacacaatgacatgtacagagaatggctggtcccctcctcccaaatgc
Q N G Q D T M T C T E N G W S P P P K C
Atccgtatcaagacatgttcagcatcagatatacacattgacaatggatttctttctgaa
I R I K T C S A S D I H I D N G F L S E
tcttcttctatatatgctctaaatagagaaacatcctatagatgtaagcagggatatgtg
S S S I Y A L N R E T S Y R C K Q G Y V SCR8
acaaatactggagaaatatcaggatcaataacttgccttcaaaatggatggtcacctcaa
T N T G E I S G S I T C L Q N G W S P Q
Ccctcatgcattaagtcttgtgatatgcctgtatttgagaattctataactaagaatact
P S C I K S C D M P V F E N S I T K N T
aggacatggtttaagctcaatgacaaattagactatgaatgtctcgttggatttgaaaat
R T W F K L N D K L D Y E C L V G F E N SCR9
gaatataaacataccaaaggctctataacatgtacttattatggatggtctgatacaccc
E Y K H T K G S I T C T Y Y G W S D T P
Tcatgttatgaaagagaatgcagtgttcccactctagaccgaaaactagtcgtttccccc
S C Y E R E C S V P T L D R K L V V S P
agaaaagaaaaatacagagttggagatttgttggaattctcctgccattcaggacacaga
R K E K Y R V G D L L E F S C H S G H R SCR10
gttgggccagattcagtgcaatgctaccactttggatggtctcctggtttccctacatgt
V G P D S V Q C Y H F G W S P G F P T C
Aaaggtcaagtagcatcatgtgcaccacctcttgaaattcttaatggggaaattaatgga
K G Q V A S C A P P L E I L N G E I N G
gcaaaaaaagttgaatacagccatggtgaagtggtgaaatatgattgcaaacctagattc
A K K V E Y S H G E V V K Y D C K P R F SCR11
ctactgaagggacccaataaaatccagtgtgttgatgggaattggacaaccttgcctgta
L L K G P N K I Q C V D G N W T T L P V
tgtattgaggaggagagaacatgtggagacattcctgaacttgaacatggctctgccaag
C I E E E R T C G D I P E L E H G S A K
tgttctgttcctccctaccaccatggagattcagtggagttcatttgtgaagaaaacttc
C S V P P Y H H G D S V E F I C E E N F SCR12
acaatgattggacatgggtcagtttcttgcattagtggaaaatggacccagcttcctaaa
T M I G H G S V S C I S G K W T Q L P K
Tgtgttgcaacagaccaactggagaagtgtagagtgctgaagtcaactggcatagaagca
C V A T D Q L E K C R V L K S T G I E A
ataaaaccaaaattgactgaatttacgcataactccaccatggattacaaatgtagagac
I K P K L T E F T H N S T M D Y K C R D SCR13
aagcaggagtacgaacgctcaatctgtatcaatggaaaatgggatcctgaaccaaactgt
K Q E Y E R S I C I N G K W D P E P N C

FIG 17C

Acaagcaaaacatcctgccctcctccaccgcagattccaaatacccaagtgattgaaacc
T S K T S C P P P P Q I P N T Q V I E T
accgtgaaatacttggatggagaaaaattatctgttctttgccaagacaattacctaact
T V K Y L D G E K L S V L C Q D N Y L T SCR14
caggactcagaagaaatggtgtgcaaagatggaaggtggcagtcattacctcgctgcatt
Q D S E E M V C K D G R W Q S L P R C I
Gaaaaaattccatgttcccagccccctacaatagaacatggatctattaatttacccaga
E K I P C S Q P P T I E H G S I N L P R
tcttcagaagaaaggagagattccattgagtccagcagtcatgaacatggaactacattc
S S E E R R D S I E S S S H E H G T T F SCR15
agctatgtctgtgatgatggtttcaggatacctgaagaaaataggataacctgctacatg
S Y V C D D G F R I P E E N R I T C Y M
Ggaaaatggagcactccacctcgctgtgttggacttccttgtggacctccaccttcaatt
G K W S T P P R C V G L P C G P P P S I
cctcttggtactgtttctcttgagctagagagttaccaacatggggaagaggttacatac
P L G T V S L E L E S Y Q H G E E V T Y SCR16
cattgttctacaggctttggaattgatggaccagcatttattatatgcgaaggaggaaag
H C S T G F G I D G P A F I I C E G G K
Tggtctgacccaccaaaatgcataaaaacggattgtgacgttttacccacagttaaaaat
W S D P P K C I K T D C D V L P T V K N
gccataataagaggaaagagcaaaaaatcatataggacaggagaacaagtgacattcaga
A I I R G K S K K S Y R T G E Q V T F R SCR17
tgtcaatctccttatcaaatgaatggctcagacactgtgacatgtgttaatagtcggtgg
C Q S P Y Q M N G S D T V T C V N S R W
Attggacagccagtatgcaaagataattcctgtgtggatccaccacatgtgccaaatgct
I G Q P V C K D N S C V D P P H V P N A
actatagtaacaaggaccaagaataaatatctacatggtgacagagtacgttatgaatgt
T I V T R T K N K Y L H G D R V R Y E C SCR18
aataaacctttggaactatttgggcaagtggaagtgatgtgtgaaaatgggatatggaca
N K P L E L F G Q V E V M C E N G I W T
Gaaaaaccaaagtgccgagactcaacagggaaatgtgggcctcctccacctattgacaat
E K P K C R D S T G K C G P P P P I D N
ggagacatcacctccttgtcattaccagtatatgaaccattatcatcagttgaatatcaa
G D I T S L S L P V Y E P L S S V E Y Q SCR19
tgccagaagtattatctccttaagggaaagaagacaataacatgtagaaatggaaagtgg
C Q K Y Y L L K G K K T I T C R N G K W
Tctgagccaccaacatgcttacatgcatgtgtaatacccagaaaacattatggaatcacac
S E P P T C L H A C V I P E N I M E S H
aatataattctcaaatggagacacactgaaaagatttattcccattcaggggaggatatt
N I I L K W R H T E K I Y S H S G E D I SCR20
gaatttggatgtaaatatggatattataaagcaagagattcaccgccatttcgtacaaag
E F G C K Y G Y Y K A R D S P P F R T K
tgcattaatggcaccatcaattatcccacttgtgtataa
C I N G T I N Y P T C V -

FIG 18A

Atggtacagcacagatttctcttggagtcagttggtcccagaaagatccaaattatgaga Signal Peptide
M V Q H R F L L E S V G P R K I Q I M R
Ctgtcagcaagaattatttggcttatattatggactgtttgtgcagcagaagattgtaaa
L S A R I I W L I L W T V C A A E D C K
ggtcctcctccaagagaaaattcagaaattctctcaggctcgtggtcagaacaactatat
G P P P R E N S E I L S G S W S E Q L Y SCR1
ccagaaggcacccaggctacctacaaatgccgccctggataccgaacacttggcactatt
P E G T Q A T Y K C R P G Y R T L G T I
gtaaaagtatgcaagaatggaaaatgggtggcgtctaacccatccaggatatgtcggaaa
V K V C K N G K W V A S N P S R I C R K
Aagccttgtgggcatcccggagacacaccctttgggtcctttaggctggcagttggatct
K P C G H P G D T P F G S F R L A V G S
caatttgagtttggtgcaaaggttgtttatacctgtgatgatgggtatcaactattaggt
Q F E F G A K V V Y T C D D G Y Q L L G SCR2
gaaattgattaccgtgaatgtggtgcagatgggtggatcaatgatattccactatgtgaa
E I D Y R E C G A D G W I N D I P L C E
Gttgtgaagtgtctacctgtgacagaactcgagaatggaagaattgtgagtggtgcagca
V V K C L P V T E L E N G R I V S G A A
gaaacagaccaggaatactattttggacaggtggtgcggtttgaatgcaattcaggcttc
E T D Q E Y Y F G Q V V R F E C N S G F SCR3
aagattgaaggacataaggaaattcattgctcagaaaatggcctttggagcaatgaaaag
K I E G H K E I H C S E N G L W S N E K
Ccacgatgtgtggaaattctctgcacaccaccgcgagtggaaaatggagatggtataaat
P R C V E I L C T P P R V E N G D G I N
gtgaaaccagtttacaaggagaatgaaagataccactataagtgtaagcatggttatgtg
V K P V Y K E N E R Y H Y K C K H G Y V SCR4
cccaaagaaagaggggatgccgtctgcacaggctctggatggagttctcagcctttctgt
P K E R G D A V C T G S G W S S Q P F C
gaagaaaagagaaccttg
E E K R T L
aaaccatgtgaatttccacaattcaaatatggacgtctgtattatgaagagagcctgaga
K P C E F P Q F K Y G R L Y Y E E S L R
cccaacttcccagtatctataggaaataagtacagctataagtgtgacaacggttttca
P N F P V S I G N K Y S Y K C D N G F S SCR6

FIG 18B ccaccttctgggtattcctgggactaccttcgttgcacagcacaagggtgggagcctgaa
P P S G Y S W D Y L R C T A Q G W E P E
Gtcccatgcgtcaggaaatgtgttttccattatgtggagaatggagactctgcatactgg
V P C V R K C V F H Y V E N G D S A Y W
gaaaaagtatatgtgcagggtcagtctttaaaagtccagtgttacaatggctatagtctt
E K V Y V Q G Q S L K V Q C Y N G Y S L SCR7
caaaatggtcaagacacaatgacatgtacagagaatggctggtcccctcctcccaaatgc
Q N G Q D T M T C T E N G W S P P P K C
Atccgtatcaagacatgttcagcatcagatatacacattgacaatggatttctttctgaa
I R I K T C S A S D I H I D N G F L S E
tcttcttctatatatgctctaaatagagaaacatcctatagatgtaagcagggatatgtg
S S S I Y A L N R E T S Y R C K Q G Y V SCR8
acaaatactggagaaatatcaggatcaataacttgccttcaaaatggatggtcacctcaa
T N T G E I S G S I T C L Q N G W S P Q
Ccctcatgcattaagtctcgagactcaacagggaaatgtgggcctcctccacctattgac
P S C I K S R D S T G K C G P P P P I D
aatggagacatcacctccttgtcattaccagtatatgaaccattatcatcagttgaatat
N G D I T S L S L P V Y E P L S S V E Y
caatgccagaagtattatctccttaagggaaagaagacaataacatgtagaaatggaaag
Q C Q K Y Y L L K G K K T I T C R N G K SCR19
tggtctgagccaccaacatgcttacatgcatgtgtaataccagaaaacattatggaatca
W S E P P T C L H A C V I P E N I M E S
cacaatataattctcaaatggagacacactgaaaagatttattcccattcaggggaggat
H N I I L K W R H T E K I Y S H S G E D SCR20
attgaatttggatgtaaatatggatattataaagcaagagattcaccgccatttcgtaca
I E F G C K Y G Y Y K A R D S P P F R T
aagtgcattaatggcaccatcaattatcccacttgtgtataa
K C I N G T I N Y P T C V -

FIG 19

GGTCTACTATTTTAGTTTACTTTGCAGAAGTTGCTCATGGGCGGAGCAATCCTGATTTC
CTAAACTGACTTTCAACTTCCCTTTGAAGCAAGTCTTTCCCTGCTGTGACCACAGTTCA
TAGCAGAGAGGAACTGGatggtacagcacagatttctcttggagtcagttggtcccagaa
Agatccaaattatgagactgtcagcaagaattatttggcttatattatggactgtttgtg
Cagcagaagattgtaaaggtcctcctccaagagaaaattcagaaattctctcaggctcgt
Ggtcagaacaactatatccagaaggcacccaggctacctacaaatgccgccctggatacc
Gaacacttggcactattgtaaaagtatgcaagaatggaaaatgggtggcgtctaacccat
ccaggatatgtcggaaaAagccttgtgggcatcccggagacacacccctttgggtccttta
ggctggcagttggatctcaatttgagtttggtgcaaaggttgtttatacctgtgatgatg
ggtatcaactattaggtgaaattgattaccgtgaatgtggtgcagatgggtggatcaatg
atattccactatgtgaaGttgtgaagtgtctacctgtgacagaactcgagaatggaagaa
ttgtgagtggtgcagcagaaacagaccaggaatactattttggacaggtggtgcggtttg
aatgcaattcaggcttcaagattgaaggacataaggaaattcattgctcagaaaatggcc
tttggagcaatgaaaagCcacgatgtgtggaaattctctgcacaccaccgcgagtggaaa
atggagatggtataaatgtgaaaccagtttacaaggagaatgaaagataccactataagt
gtaagcatggttatgtgcccaaagaaagaggggatgccgtctgcacaggctctggatgga
gttctcagcctttctgtgaagaaaagagaaccttgaaaccatgtgaatttccacaattca
aatatggacgtctgtattatgaagagagcctgagacccaacttcccagtatctataggaa
ataagtacagctataagtgtgacaacgggttttcaccaccttctgggtattcctgggact
accttcgttgcacagcacaagggtgggagcctgaaGtcccatgcgtcaggaaatgtgttt
tccattatgtggagaatggagactctgcatactgggaaaaagtatatgtgcagggtcagt
ctttaaaagtccagtgttacaatggctatagtcttcaaaatggtcaagacacaatgacat
gtacagagaatggctggtcccctcctcccaaatgcAtccgtatcaagacatgttcagcat
cagatatacacattgacaatggatttctttctgaatcttcttctatatatgctctaaata
gagaaacatcctatagatgtaagcagggatatgtgacaaatactggagaaatatcaggat
caataacttgccttcaaaatggatggtcacctcaaCcctcatgcattaagtctcgagact
caacagggaaatgtgggcctcctccacctattgacaatggagacatcacctccttgtcat
taccagtatatgaaccattatcatcagttgaatatcaatgccagaagtattatctcctta
agggaaagaagacaataacatgtagaaatggaaagtggtctgagccaccaacatgcttac
atgcatgtgtaataccagaaaacattatggaatcacacaatataattctcaaatggagac
acactgaaaagatttattcccattcaggggaggatattgaatttggatgtaaatatggat
attataaagcaagagattcaccgccatttcgtacaaagtgcattaatggcaccatcaatt
atcccacttgtgtataaAATCATAATACATTTATTAGTTGATTTTATTGTTTAGAAAGGC
ACATGCATGTGACTAATATACTTTCAATTTGCATTGAAGTATTGTTTAACTCATGTCTTC
TCATAAATATAAACATTTTTGTTATATGGTGATTAATTTGTAACTTTAAAAACTATTGCC
AAAATGCAAAAGCAGTAATTCAAAACTCCTAATCTAAAATATGATATGTCCAAGGACAAA
CTATTTCAATCAAGAAAGTAGATGTAAGTTCTTCAACATCTGTTTCTATTCAGAACTTTC
TCAGATTTTCCTTGATACCTTTTGATGTAAGGTCCTGATTTACAGTGGATAAAGGATATA
TTGACTGATTCTTCAAATTAATATGATTTCCCAAAGCATGTAACAACCAAACTATCATAT
ATTATATGACTAATGCATACAATTAATTACTATATAATACTTTCAAATAAAAGAATCTAA
GAAACTTC

FIG 20

MVQHRFLLESVGPRKIQIMRLSARIIWLILWTVCAAEDCKGPPPRENSEILSGSWSEQLY
PEGTQATYKCRPGYRTLGTIVKVCKNGKWVASNPSRICRKKPCGHPGDTPFGSFRLAVGS
QFEFGAKVVYTCDDGYQLLGEIDYRECGADGWINDIPLCEVVKCLPVTELENGRIVSGAA
ETDQEYYFGQVVRFECNSGFKIEGHKEIHCSENGLWSNEKPRCVEILCTPPRVENGDGIN
VKPVYKENERYHYKCKHGYVPKERGDAVCTGSGWSSQPFCEEKRTLKPCEFPQFKYGRLY
YEESLRPNFPVSIGNKYSYKCDNGFSPPSGYSWDYLRCTAQGWEPEVPCVRKCVFHYVEN
GDSAYWEKVYVQGQSLKVQCYNGYSLQNGQDTMTCTENGWSPPPKCIRIKTCSASDIHID
NGFLSESSSIYALNRETSYRCKQGYVTNTGEISGSITCLQNGWSPQPSCIKSRDSTGKCG
PPPPIDNGDITSLSLPVYEPLSSVEYQCQKYYLLKGKKTITCRNGKWSEPPTCLHACVIP
ENIMESHNIILKWRHTEKIYSHSGEDIEFGCKYGYYKARDSPPFRTKCINGTINYPTCV

FIG 21
Expression of mouse fH variants in Hepa1C1C1 cells
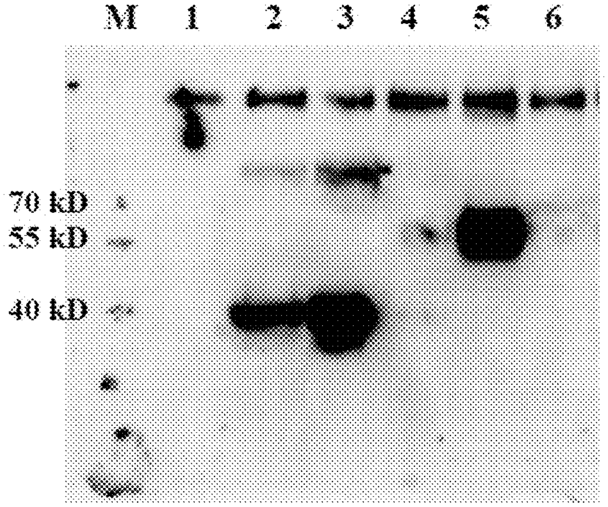
M: MW marker
1: Control
2: mfH1-4.19-20 cl3
3: mfH1-4.19-20 cl4
5: mfH1-4.678.19-20 cl1
6: mfH1-4.678.19-20 cl2
(AS)
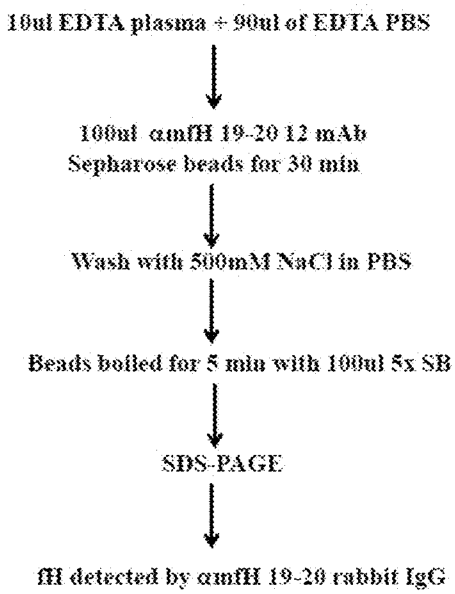
FIG 22A
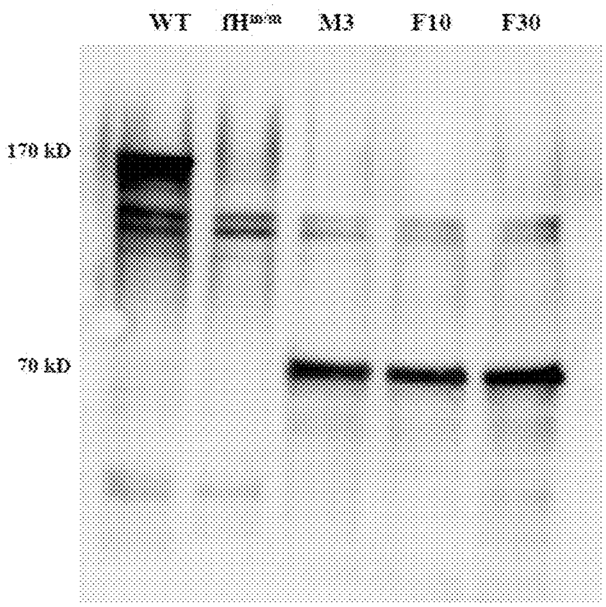
FIG 22B Intact C3 and fB levels in fH$^{m/m}$ mice 1: WT        2: M3 pre
3: M3 1W     4: M3 1M
5: F10 pre   6: F10 1W
7: F10 1M    8: F30 pre
9: F30 1W    10: F30 1M 1: WT
2: M1 pre
3: M1 1W
4: M2 pre
5: M2 1W
6: M3 pre
7: M3 1W
8: M10 pre
9: M10 1W WT: Wt mice plasma
1: M2 Pre
2: M2 1W post AAV
3: M3 Pre
4: M3 1W post AAV WT: Wt mice plasma
1: M #1 Pre
2: M #1 1W post AAV (1x $10^{12}$/gene copies)
3: M #1 1M post AAV (1x $10^{12}$/gene copies)
4: M #3 pre
5: M #3 1W post AAV (3x $10^{11}$/gene copies)
6: M #3 1M post AAV (3x $10^{11}$/gene copies)
7: M #5 Pre
8: M #5 1W post AAV (1x $10^{11}$/gene copies)
9: M #5 1M post AAV (1x $10^{11}$/gene copies)

FIG 30

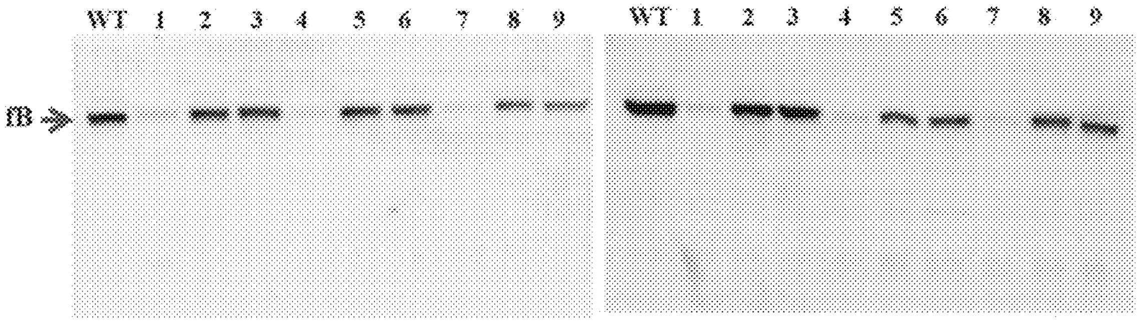

WT: Wt mice plasma
1: M #1 Pre
2: M #1 1W post AAV (1x $10^{12}$/gene copies)
3: M #1 1M post AAV (1x $10^{12}$/gene copies)
4: M #3 pre
5: M #3 1W post AAV (3x $10^{11}$/gene copies)
6: M #3 1M post AAV (3x $10^{11}$/gene copies)
7: M #5 Pre
8: M #5 1W post AAV (1x $10^{11}$/gene copies)
9: M #5 1M post AAV (1x $10^{11}$/gene copies)

WT: Wt mice plasma
1: M #2 Pre
2: M #2 1W post AAV (1x $10^{12}$/gene copies)
3: M #2 1M post AAV (1x $10^{12}$/gene copies)
4: M #4 pre
5: M #4 1W post AAV (1x $10^{11}$/gene copies)
6: M #4 1M post AAV (1x $10^{11}$/gene copies)
7: M #6 Pre
8: M #6 1W post AAV (3x $10^{11}$/gene copies)
9: M #6 1M post AAV (3x $10^{11}$/gene copies)

FIG 34B
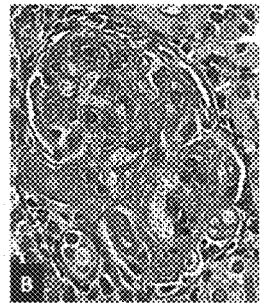
FIG 34A
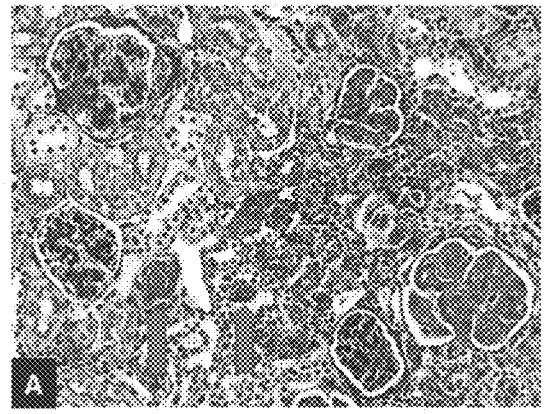
FIG 34C
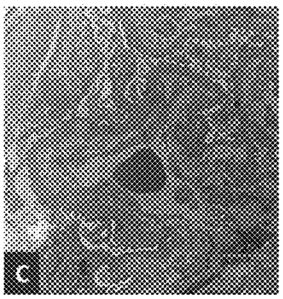
FIG 35A
WT
FIG 35B
mutant
Retinal photography
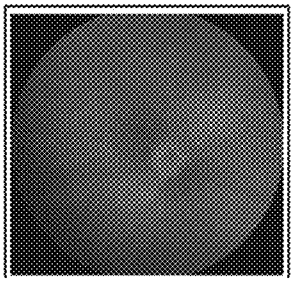
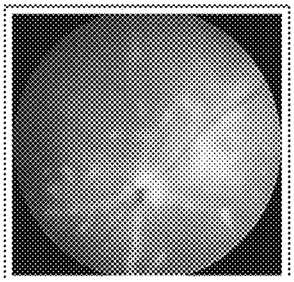
FIG 35C
FIG 35D
Fluorescein angiography
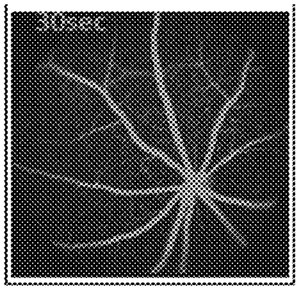
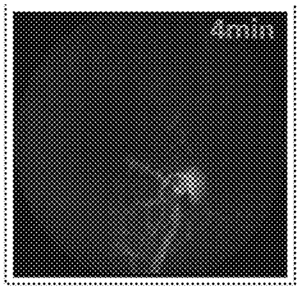

FACTOR H VARIANTS FOR TREATMENT OF DISEASE

STATEMENT REGARDING FEDERALLY SPONSORED RESEARCH OR DEVELOPMENT

This invention was made with government support under AI085596 awarded by the National Institutes of Health. The government has certain rights in the invention.

INCORPORATION-BY-REFERENCE OF MATERIAL SUBMITTED IN ELECTRONIC FORM

The sequence listing labeled "16-7640.US.A.xml" created Oct. 24, 2023, and which is 135,931 bytes in size, is incorporated herein by reference.

BACKGROUND OF THE INVENTION

The complement system is a part of innate immunity that plays a key role in host defense. Complement can be activated by three different pathways, the classical, alternative and lectin pathways. Among them, the alternative pathway is unique in that it not only represents an independent pathway by which complement is activated by the "tick-over" mechanism, but also it amplifies complement activation initiated by the other two pathways. The alternative pathway requires the participation of C3, factor B (fB), factor D (fD) and properdin (fP). All pathways converge at the C3 activation step from where the alternative pathway amplification loop comes into play. Regardless of which pathway complement activation occurs, activated complement produces three types of effector functions: opsonization of targets with C3b/iC3b/C3d to facilitate phagocytosis and clearance, production of pro-inflammatory mediators C3a and C5a, and direct cellular attack by the terminal complement activation effector C5b-9, also known as membrane attack complex (MAC). Through activation of complement receptors (CRs) such as CR2 on B cells and follicular dendritic cells, and anaphylatoxin receptors C3a receptor (C3aR) and C5a receptor (C5aR) on leuckocytes such as macrophages and monocytes, complement also interacts with and cross-regulates the adaptive immune systems and thus plays a modulatory role in B and T cell immunology.

A number of human diseases are caused by complement dysregulation, resulting in complement-mediated autologous tissue injury. The complement dysregulation may arise from mutations, either somatic or germline, in complement regulator or regulator-related genes such that these regulators no longer function normally. Examples of this category include mutations in hematopoietic stem cells of the PIG-A gene that encodes for a key enzyme in the GPI anchor biosynthesis and such mutations result in the lack of expression of DAF and CD59 on blood cells of paroysmal nocturnal hemoglobinuria (PNH) patients. As a result, PNH patient's red blood cells and platelets are not protected from complement attack and they develop intravascular hemolysis and platelet activation, leading to anemia and thrombotic attacks. A second example is mutation in the membrane regulator MCP or fluid phase regulators fH or fI which render over-activation of the alternative pathway of complement in the kidney, leading to the pathogenesis of C3 glomerulopathy or atypical hemolytic uremic syndrome (aHUS). In addition to such rare and high penetrant mutations leading to absence of expression or dysfunction of DAF, CD59, fH, fI and MCP, there are single nucleotide polymorphisms (SNP) in fH that are more prevalent and less penetrant but nevertheless have been identified to contribute to disease pathogenesis via a complement-mediated mechanism. A very well characterized example is the strong association of Y420H polymorphism in fH with age-related macular degeneration (AMD). Thus, complement regulator dysfunction or sequence variation may lead to common as well as rare human diseases.

Complement dysregulation may arise not only from regulatory mutation/polymorphism but also from mutations in genes that encode the critical components of the alternative pathway, namely C3 and fB, as well as by the presence of autoantibodies against regulators or complement proteins such as fH, C3 or fB. It is now understood that certain mutations in C3 or fB will result in proteins which, when activated, form an unusually stable alternative pathway C3 convertase C3bBb that is resistant to regulation by the regulatory proteins, which in turn can lead to complement dysregulation and over-activation. In the case of autoantibodies against complement regulators, they often mimic mutations in genes encoding such proteins with the result being reduced functional potency of such proteins in the fluid phase or on the cell surface. Separately, autoantibodies against C3b called C3 nephritic factors (C3nef) are capable of binding and stabilizing the alternative pathway C3 convertase C3bBb, thus achieving the same effect of prolonging the half-life and activity of the convertase as that produced by C3 or fB gene mutations. Overall, there are common and rare human diseases that are caused by excessive complement activation resulting from dysregulation of the complement activation cascade. The underlying mechanism of complement dysregulation are variable, some are due to gene mutations and others to autoantibodies, and the mutated genes or targets of autoantibodies could be regulatory proteins or components of the alternative pathway.

Current therapeutic approaches are focused on the development of reagents such as mAbs, peptides or other small molecules that bind and block specific alternative pathway or terminal pathway complement components. A clinically validated example is Eculizumab, a humanized mAb against complement C5 which has been approved for the treatment of PNH and aHUS. Other approaches that have been described include mAbs against fB, fD, or fP, and a cyclic peptide that binds and inhibits C3. The limitation of these approaches is that they require repeated and inconvenient IV dosing of patients. Further, since they block the alternative pathway or terminal pathway, they run the risk of compromising host defense. Indeed, patients on Eculizumab therapy have to be vaccinated against bacteria strains that cause lethal meningitis and these patients are also put on prophylactic antibiotic therapy before being treated with the approved mAb drug.

In other approaches, recombinant regulatory proteins such as soluble DAF, CR1, CRIg and proteins comprising minimal domains of fH (N-terminal short consensus repeat [SCR] 1-5 and C-terminal SCR 19-20) or fusion proteins between fH and CR2 (TT30) have been tested. See, e.g., US Patent Publication No. US2013/0296255; US Patent Publication No. 2008/0221011. However, large scale heterologous expression of such proteins as therapeutic drugs requires significant effort, and animal studies have shown their in vivo clearance rate after administration to be fast (Nichols E M, Barbour T D, Pappworth I Y, Wong E K, Palmer J M, Sheerin N S, Pickering M C, Marchbank K J. Kidney Int. 2015 Jul. 29. doi: 10.1038/ki.2015.233.; Fridkis-Hareli M, Storek M, Mazsaroff I, Risitano A M, Lundberg A S, Horvath C J, Holers V M, Blood. 2011 Oct. 27; 118(17): 4705-13. doi: 10.1182/blood-2011-06-359646. Epub 2011 Aug. 22.), making such therapeutic strategies cumbersome and less practical as multiple and frequent administrations of such protein drugs would be required.

A need remains in the art for compositions useful for treating complement-mediated diseases with greater and longer-lasting efficacy.

SUMMARY OF THE INVENTION

In one aspect, the invention provides a recombinant vector having packaged therein an expression cassette comprising an engineered human complement regulator factor H (fH) gene operably linked to expression control sequences which direct expression thereof, wherein said hfH gene encodes a soluble hfH protein variant that retains complement regulatory function, wherein said fH variant comprises short consensus repeat (SCR) 1, 2, 3, 4, 19 and 20 and at least one of SCR7, SCR17 and/SCR18, wherein following administration of the vector to a subject and expression, detectable plasma levels of the hfH variant are present in the subject for at least a week.

In another aspect, the invention provides a recombinant AAV vector having packaged therein an expression cassette comprising an engineered human complement regulator factor H (fH) gene operably linked to expression control sequences which direct expression thereof, wherein said hfH gene encodes a soluble hfH protein variant that retains complement regulatory function, wherein said fH variant comprises short consensus repeat (SCR) 1, 2, 3, 4, 19 and 20, wherein following administration of the vector to a subject and expression, detectable therapeutically useful plasma levels of the hfH variant are present in the subject for at least about a month.

In a further aspect, a pharmaceutical composition is provided which comprises a carrier and/or excipient and a recombinant vector as described herein which expresses an fH variant.

In yet another aspect, a method is provided for treating a complement related disorder by delivering to the subject a vector as described herein. The complement related disorder may be, among others, membranoproliferative glomerulonephritis, atypical hemolytic uremic syndrome (aHUS), age related macular degeneration (AMD), microangiopathic haemolytic anemia, thrombocytopenia, acute renal failure, paroxysmal nocturnal hemoglobinuria (PNH), schizophrenia, ischemic stroke, and/or bacterial infections caused by recruitment of bacterial pathogens.

In a further aspect, use of a recombinant vector for treating AMD is provided. In another aspect, use of a rAAV vector for treating PNH, aHUS, or another complement associated disorder is described.

In another aspect, an engineered hfH variant is provided which comprises a leader sequence and human complement receptor SCRs consisting of: (a) SCR1-4, 7, and 19-20; (b) SCR1-4, 6, 7, and 19-20; (c) SCR1-4, 7, 8, and 19-20; (d) SCR1-4, 6, 7, 8, and 19-20; (e) SCR1-4, 17, and 19-20; (f) SCR1-4, and 18-20; (g) SCR1-4, and 17-20. Other embodiments include, e.g., SCR1-4, 7, and 18-20; SCR1-4, 6, 7, and 18-20; SCR1-4, 7, 8, and 18-20; or SCR1-4, 6, 7, 8, and 18-20, SCR1-4, 7, and 17-20; SCR1-4, 6, 7, and 17-20; SCR1-4, 7, 8, and 17-20; or SCR1-4, 6, 7, 8, and 17-20. Optionally, at least one glycosylation site is engineered into at least one of the SCRs. In another aspect, one of the engineered hfH variants is pegylated.

In still another aspect, a pharmaceutical composition comprising at least one type of the engineered hfH variant, a carrier and/or an excipient is provided. Such a composition may be used on its own, or in combination with another therapy, particularly, e.g., the vector therapy described herein.

Other aspects and advantages of the invention will be readily apparent from the following detailed description of the invention.

BRIEF DESCRIPTION OF THE DRAWINGS

FIG. 1A provides a schematic of the domain structure of mature human factor H protein.

FIG. 1B-FIG. 1E provide the nucleic acid and amino acid sequences of the leader peptide and identifies the locations of the 20 Short Consensus Repeat (SCR) domains used in generating the fH variants illustrated in the examples below. SEQ ID NO:1 provides the nucleic acid sequences; SEQ ID NO: 2 provides the amino acid sequence of the signal peptide. The amino acid sequences of the SCR1-20 are provided in SEQ ID NO: 3 (SCR1), 5 (SCR2), 7 (SCR3), 9 (SCR4), 11 (SCR5), 13 (SCR6), 14 (SCR7), 16 (SCR8), 17 (SCR9), 19 (SCR10), 21 (SCR11), 23 (SCR12), 25 (SCR13), 27 (SCR14), 29 (SCR15), 31 (SCR16), 33 (SCR17), 35 (SCR18), 37 (SCR19), and 38 (SCR20) respectively. The locations of these domains in the fH isoform 1 are based on the convention described in C. Estaller et al, Eur J Immunol. 1991 March; 21(3):799-802. The amino acids sequences between the defined SCRs are linker sequences that afford fH flexibility [SEQ ID NO: 4, 6, 8, 10, 12, 15, 18, 20, 22, 24, 26, 28, 30, 32, 34, and 36], respectively]. The linker between SCR19 and SCR20 is only three amino acids (Leu-His-Pro), and thus not generated by the features in the Sequence Listing.

FIG. 2A provides a schematic domain structure of human factor H variant containing SCR1-4, 6-8, and 19-20.

FIG. 2B-FIG. 2C provide the nucleic acid [nt 53-1804 of SEQ ID NO: 41] and amino acid sequences [SEQ ID NO: 42] of the leader peptide and 9 short consensus repeat (SCR) domains of the fH variant SCR1-4, 6-8 and 19-20.

FIG. 3A-FIG. 3B are the complete cDNA [nt 53-1804 of SEQ ID NO: 41] and 5'-[nt 1-52 of SEQ ID NO:41] and 3'-UTR [nt 1805-2068 of SEQ ID NO: 41] sequences of the human factor H truncation construct containing the leader peptide and SCR1-4, 6-8, and 19-20 (hfH1-4.678.19-20).

FIG. 4 is the amino acid sequence of the factor H truncation construct containing the leader peptide (underlined) and SCR1-4, 6-8, 19-20 (hfH1-4.678.19-20) [SEQ ID NO: 42].

FIG. 5A and FIG. 5B are gels which provide confirmation of protein expression and stability of hfH1-4.678.19-20. The cDNA sequence shown in FIG. 2B and FIG. 2C of human fH truncation variant containing SCR1-4, 6-8, and 19-20 [SEQ ID NO: 41] was cloned into eukaryotic expression vectors which were then used to transfect HEK cells. Cell culture supernatant was used for western blot analysis to detect truncated fH protein expression. (FIG. 5A) Lane 1, untransfected HEK cells; Lane 2 and 3, HEK cells transfected with a pCMV Sport6 vector containing the fH truncation variant cDNA; Lane 4-6, HEK cells transfected with a pCBARBG vector containing the fH variant cDNA. The pCBARBG vector contains the same 5' and 3' regulatory elements as the pAAV vector construct shown in FIG. 4. (FIG. 5B) Lane 1, untransfected HEK cells; Lane 2, HEK cells transfected with a pCBARG vector containing the truncated fH variant cDNA as a control; Lane 3, HEK cells transfected with the AAV8 plasmid containing the truncated fH variant cDNA.

FIG. 12B and FIG. 12C provide the nucleic acid and amino acid sequences of the leader peptide and 11 short consensus repeat (SCR) domains of the fH variant SCR1-4, 6-8 and 17-20 [SEQ ID NO: 45 and 46, respectively].

FIG. 13 is the complete cDNA and 5'UTR sequences of the human factor H variant containing the leader peptide and SCR1-4, 6-8 and 17-20 (hfH1-4.678.17-20) (5'UTR is in capital letters) [SEQ ID NO: 47].

FIG. 14 is the amino acid sequence of the factor H truncation construct containing the leader peptide (underlined) and SCR1-4, 6-8, and 17-20 (hfH1-4.678.17-20) [SEQ ID NO 48].

FIG. 17A-FIG. 17C show the nucleic acid and amino acid sequences of the leader peptide and the 20 Short Consensus Repeat (SCR) domains in mice [SEQ ID NO: 79 and 80, respectively]. Amino acid sequences between the defined SCRs are linker sequences that afford fH flexibility.

FIG. 18A and FIG. 18B provide the nucleic acid and amino acid sequences of the leader peptide and 9 Short Consensus Repeat (SCR) domains of the mouse fH variant [SEQ ID NO: 81 and 82, respectively]. Amino acid sequences between the defined SCRs are linker sequences that afford fH protein flexibility. This variant of mouse fH is used as a surrogate for testing the in vivo function of hfH1-4.678.19-20 in subsequent studies.

FIG. 19 provides the coding and 5' and 3'-UTR sequences of the mouse factor H truncation construct containing the leader peptide (underlined) and SCR1-4, 6-8, 19-20 (mfH1-4.678.19-20) [SEQ ID NO: 43].

FIG. 20 provides the amino acid sequence of the mouse factor H truncation construct containing the leader peptide (underlined) and SCR1-4, 6-8, and 19-20 (mfH1-4.678.19-20) [SEQ ID NO:44].

FIG. 21 is a gel showing confirmation of protein expression and stability of mfH1-4.19-20 and mfH1-4.678.19-20. The cDNA sequence of mouse fH truncation variant containing SCR1-4, 678, and 19-20 or that of another fH truncation variant containing SCR1-4, and 19-20 was cloned into a eukaryotic expression vector pCBARBG which was then used to transfect a mouse liver cell line, Hepa1C1C7 cells. Cell culture supernatant was used for western blot analysis to detect truncated mouse fH protein expression. M: molecular weight markers; Lane 1, untransfected Hepa1C1C7 cells (Control); Lane 2 and 3, Hepa1C1C7 cells transfected with pCBARBG-mfH1-4.19-20 clone 3 or clone 4; Lanes 5 and 6, Hepa1C1C7 cells transfected with pCBARBG-mfH1-4.678.19-20 clone 1 (sense) or clone 2 (antisense).

FIG. 22A is a flow chart showing how blood samples were collected and processed for fH protein detection. The $fH^{m/m}$ mouse is a strain of fH mutant mice that carry premature stop codons at the beginning of SCR19. These mice produce trace amount of truncated fH (lacking SCR19-20) and has uncontrolled fluid phase alternative pathway complement activation and consumption (secondary C3 and fB deficiency). Mice were infected by retro-orbital I.V. with an AAV8 virus containing mfH1-4.678.19-20 ($3\times10^{12}$ gene copies/mouse) and after one week, blood samples were collected, processed and analyzed as shown in the flow chart.

FIG. 22B is a western blot detection of mfH1-4.678.19-20 in the blood of a fH mutant mouse ($fH^{m/m}$) one week after AAV8-mediated fH gene therapy. As shown in the figure, there was no mfH1-4.678.19-20 (approximately 70 kd) in WT and non-treated $fH^{m/m}$ mice. In three virus-infected $fH^{m/m}$ mice, M3, F10, F30 (M indicates male and F indicates female), mfH1-4.678.19-20 was clearly detected.

FIG. 30 provides a dosage comparison of AAV8-mfH1-4.678.19-20 gene therapy using fB recovery as a readout. The Western analysis was performed essentially as described in FIG. 29 where C3 was used as a readout. As shown, all doses tested were able to increase plasma fB levels when examined at 1 W and 1 M time points.

FIG. 34A-FIG. 34C show kidney sections of W1206R mutant mice showed pathologies characteristic of aHUS. The pathological features included mesangial expansion and narrowing of capillary lumens (FIG. 34A), thrombi in small vessels as indicated by arrows in FIG. 34B and FIG. 34C. Electron microscopy showed that the glomerular capillary wall exhibited sub-endothelial expansion with fluffy granular electron-lucent material, and formation of double contours and new glomerular basement membrane.

FIG. 35A-FIG. 35D show that mice carrying W1206R mutation in fH also developed retinal injury and blood clotting in the eye. Compared with normal looking retinas of wild-type mice (FIG. 35A), there were many white patches, retinal edema and dilated vessels in the retina of the fH W1206R mutant mouse (FIG. 35B). In addition, fluorescein angiography showed the mutant mouse retina was not well perfused as the dye reached all blood vessels in the wild-type mouse eye within 30 seconds (FIG. 35C) but it did not reach out to much of the area in the mutant mouse retina even at 4 min (FIG. 35D).

DETAILED DESCRIPTION OF THE INVENTION

Novel engineered factor H (fH) genes and protein variants are described herein. These variants are characterized by increased half-life and increased efficacy in treating conditions associated with factor H and other complement disorders.

Delivery of these variants to subjects in need thereof via a number of routes, and particularly by expression in vivo mediated by a recombinant vector such as a rAAV vector, are described. Also provided are methods of using these variants in regimens for treating factor H associated disorders. Advantageously, compositions provided herein are useful for simultaneously targeting multiple pathways and/or treating or modulating uncontrolled alternative pathway complement regulation caused by a variety of factors.

As used herein, the term "treating complement factor H disorders" may encompass alleviating, reducing, and/or ameliorating symptoms, and/or preventing the development of additional symptoms associated with complement factor H disorder, which can manifest as several different phenotypes, including asymptomatic, recurrent bacterial infections, and renal failure. This is typically characterized by decreased serum levels of factor H, complement component C3, and a decrease in other terminal complement components, indicating activation of the alternative complement pathway. This disorder is associated with a number of renal diseases with variable clinical presentation and progression, including C3 glomerulopathy and atypical hemolytic uremic syndrome. Also provided herein are compositions and methods for treating one or more of age related macular degeneration (AMD), atypical hemolytic uremic (including, e.g., syndrome microangiopathic haemolytic anemia, thrombocytopenia, acute renal failure), paroxysmal nocturnal hemoglobinuria (PNH), schizophrenia, ischemic stroke, and/or preventing or treating bacterial infections caused by recruitment of bacterial pathogens (e.g., *Aspergillus* spp.; *Borrelia*

*burgdorferi; B. duttonii; B. recurrentis; Candida albicans; Francisella tularensis; Haemophilus influenzae; Neisseria meningitidis; Streptococcus pyogenes*, or one of the five factor H binding proteins of *B. burgdorferi* (CRASP-1, CRASP-2, CRASP-3, CRASP-4, or CRASP-5), among others.

Figure 23:
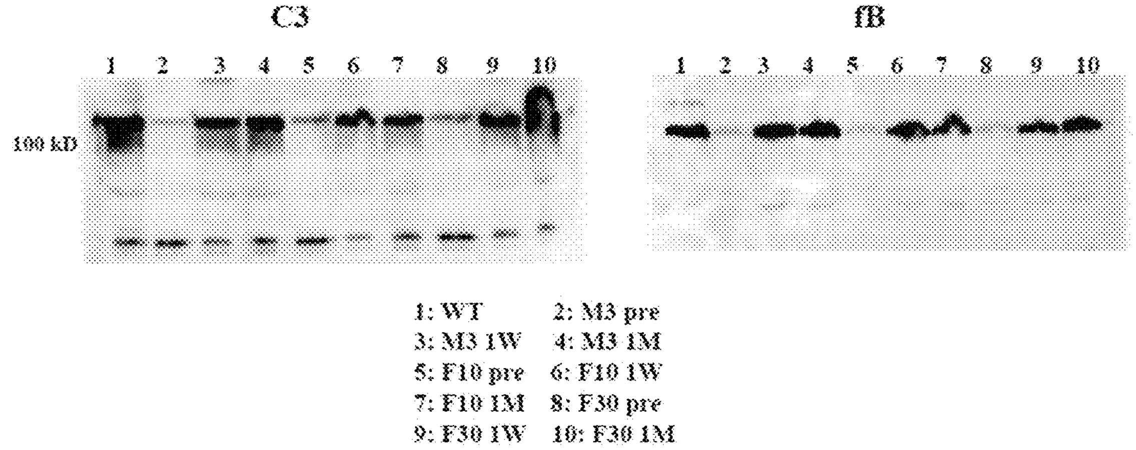
FIG. 23 is a western blot analysis demonstrating that AAV8-mediated fH gene therapy in $fH^{m/m}$ mice prevents uncontrolled alternative pathway complement activation. Due to the lack of sufficient endogenous fH expression, untreated $fH^{m/m}$ mice have uncontrolled fluid phase alternative pathway complement activation, and as a result they consume plasma C3 and fB (compare Lane 1 of WT with Lanes 2, 5, 8 of $fH^{m/m}$ mice before gene therapy). After $fH^{m/m}$ mice were treated with AAV8-mfH1-4.678.19-20, at one week (1 W, Lanes 3, 6, 9) and one month (1 M, Lanes 4, 7, 10), plasma C3 and fB levels were recovered to WT levels, suggesting that AAV8-mediated fH gene therapy prevented uncontrolled alternative pathway complement activation and C3 and fB consumption, and that the therapeutic effect was evident as early as one week and last at least one month.
Figure 24:
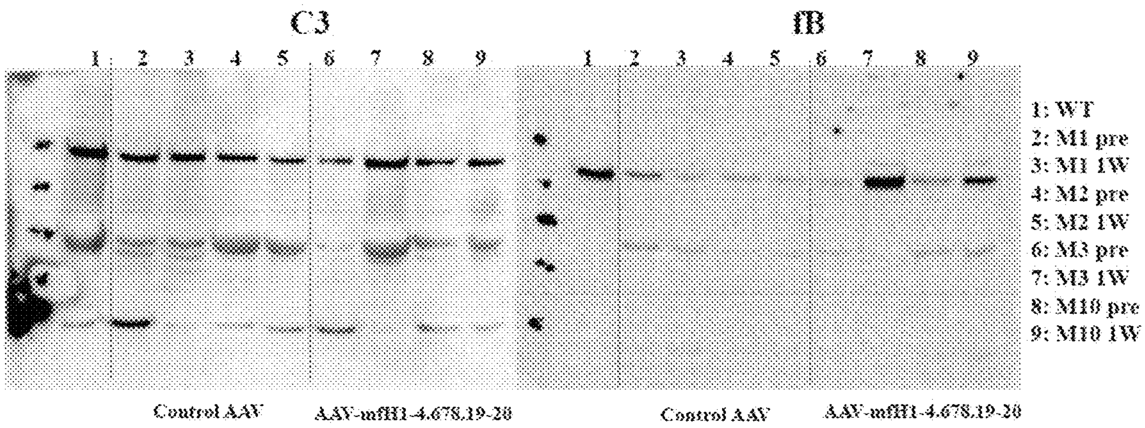
FIG. 24 is a western blot analysis demonstrating that AAV8-mediated fH gene therapy prevents uncontrolled alternative pathway complement activation in a mouse model of lethal C3 glomerulopathy. In $fH^{m/m}$ mice that are also deficient in properdin ($fH^{m/m}P^{-/-}$), a similar uncontrolled alternative pathway complement activation with C3 and fB consumption occurs. Compared with $fH^{m/m}$ mice, fHm/mP−/− mice develop a lethal form of C3G and they die by the age of 10-12 weeks old. In this experiment, two $fH^{m/m}P^{-/-}$ mice aged around 7-weeks old each were treated with AAV8-mfH1-4.678.19-20 or empty AAV8 vector (pAAV.TBG.rBG) as a control group (Control AAV). One week after AAV8 gene therapy, blood samples were collected and analyzed by western blot for C3 and fB levels. As shown in the panels, compared with blood samples before AAV8 treatment (pre), there was no difference in intact C3 or fB levels one week (1 W) after control AAV8 treatment (Lanes 2-5). However, plasma C3 and fB levels in mice one week after treatment with AAV8-mfH1-4.678.19-20 were significantly increased (Lanes 6-9), suggesting uncontrolled alternative pathway complement activation was inhibited by gene therapy. Mice were treated with AAV8 ($3\times10^{12}$ gene copies/mouse) via retro-orbital I.V. injection.
Figure 25:
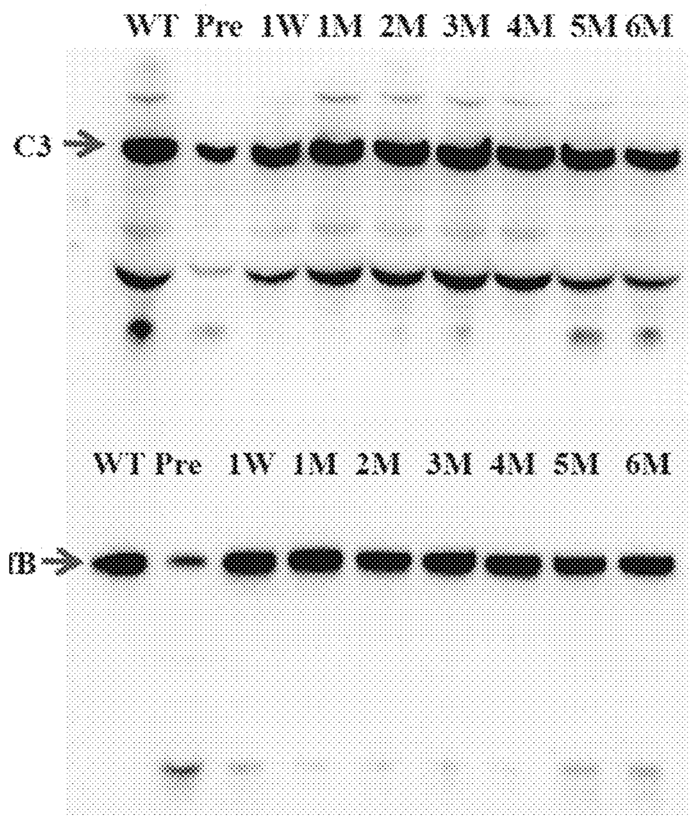
FIG. 25 shows long term follow-up of an $fH^{m/m}P^{-/-}$ (M3 from FIG. 24)-treated with AAV8-mfH1-4.678.19-20 gene therapy. Western blot analysis of plasma C3 and fB levels before gene therapy (Pre) and at 1 week (1 W), 1, 2, 3, 4, 5 and 6 months (1 M, 2M, 3M, 4M, 5M, 6M) after treating with AAV8-mfH1-4.678.19-20 showing C3 and fB were persistently elevated to wild-type mouse levels after gene therapy, suggesting that the therapeutic effect was long-lasting.
Figure 26:
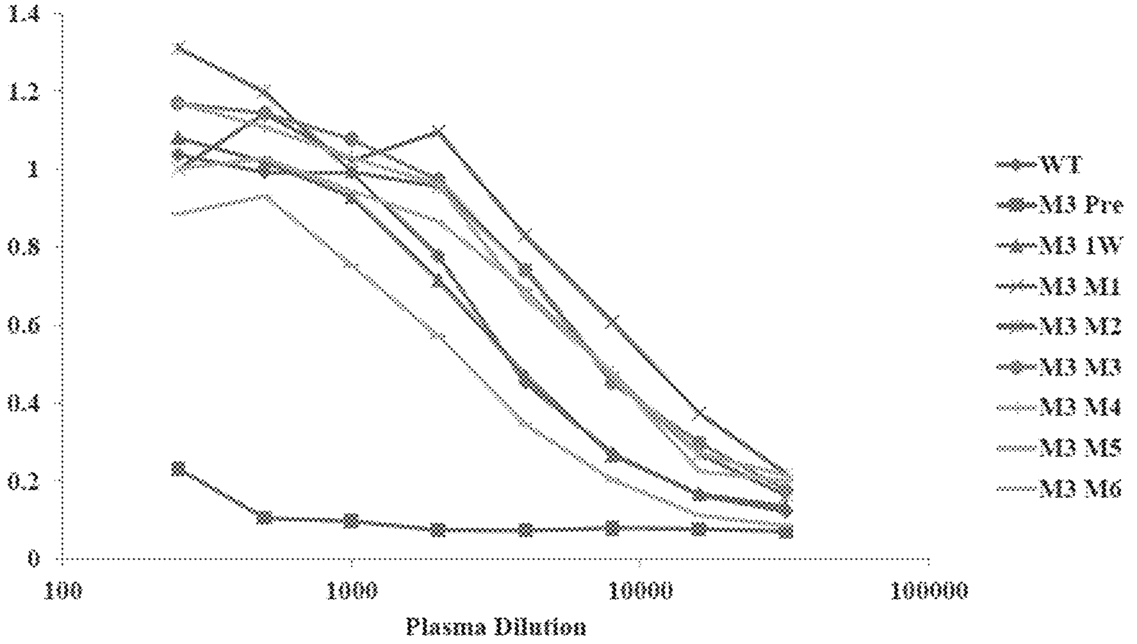
FIG. 26 shows long term follow-up of an $fH^{m/m}P^{-/-}$ (M3 from FIG. 24) treated with AAV8-mfH1-4.678.19-20 gene therapy. ELISA analysis of plasma levels of mfH1-4.678.19-20 protein before (Pre) and 1 week, 1, 2, 3, 4, 5 and 6 months (M) after treating with AAV8-mfH1-4.678.19-20 showing that mfH1-4.678.19-20 as a therapeutic protein drug was persistently expressed.
Figure 27:
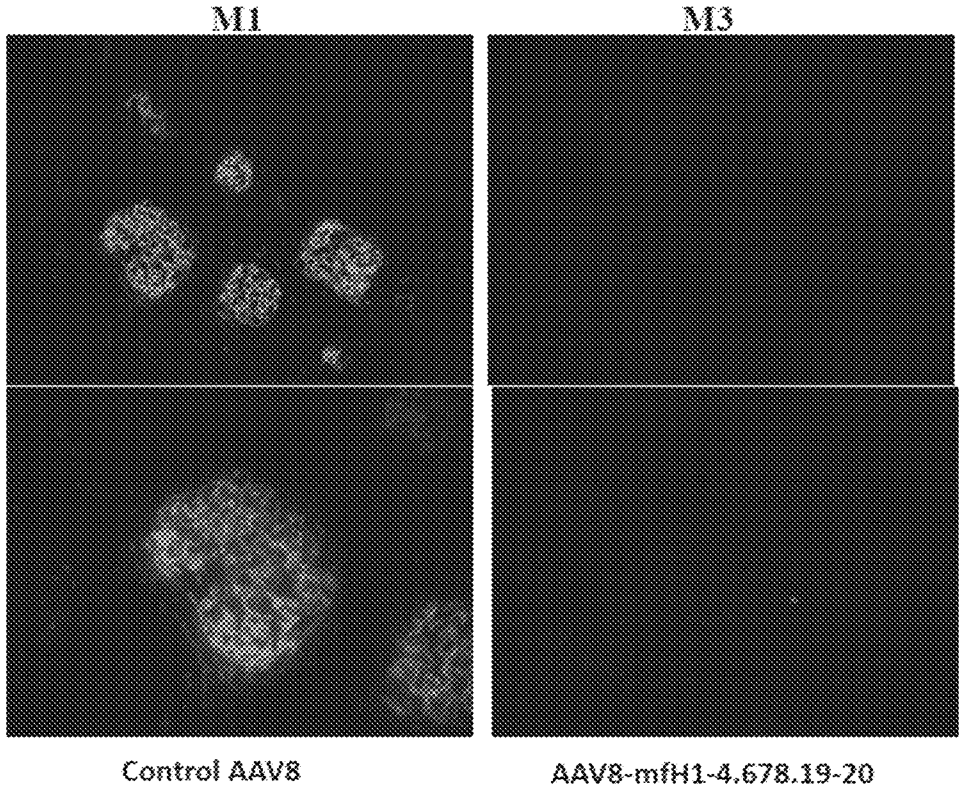
FIG. 27 shows the efficacy of AAV8-mfH1-4.678.19-20 gene therapy in preventing renal pathology in C3 glomerulopathy. An $fH^{m/m}P^{-/-}$ mouse treated with control AAV8 vector (mouse M1 from FIG. 24) was moribund within 2 weeks of treatment and immunostaining of its kidney showed strong glomerular C3 deposition as previously described for untreated $fH^{m/m}P^{-/-}$ mice (left panels). In contrast, a $fH^{m/m}P^{-/-}$ mouse treated with the AAV8-mfH1-4.678.19-20 vector (M3 from FIG. 23) survived and was still healthy at 6 month after treatment, at which time it was sacrificed and analyzed for kidney histology. No glomerular C3 deposition was detected in this mouse (right panels), suggesting C3 glomerulopathy was prevented by AAV8-mfH1-4.678.19-20 gene therapy.
Figure 28A:
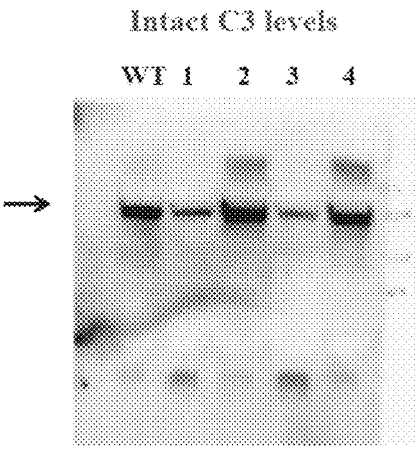
FIG. 28A and FIG. 28B demonstrate that AAV8-mfH1-4.678.19-20 gene therapy prevents alternative pathway complement activation caused by membrane regulator dysfunction. In this experiment, mice deficient in two membrane regulators, DAF and Crry, were treated with AAV8-mfH1-4.678.19-20 (retro-orbital route, I.V., $3\times10^{12}$ gene copies/mouse). Plasma samples were collected before and 1 week (1 W) after gene therapy to analyze plasma C3 (FIG. 28A) and fB (FIG. 28B) levels by western blot. As shown by the data, the DAF/Crry double mutant mice had excessive alternative pathway complement activation with low C3 and fB levels (Pre). After AAV8-mfH1-4.678.19-20 treatment, both C3 and fB were restored to wild-type mouse levels, suggesting that AAV8-mfH1-4.678.19-20 treatment can correct pathologies caused by membrane complement regulators. This data suggested that AAV8-mfH1-4.678.19-20 treatment was broadly effective for complement-mediated diseases caused by uncontrolled alternative pathway complement regulation, irrespective of the underlying regulatory mechanism defect. DAF/Crry double mutant mice used in this study is a crossbreed species between DAF knockout mice and a $Crry^{flox/flox}$-Tie-2$Cre^{+}$ mice. Because Tie-2-Cre is expressed in germ cells, it led to germline deletion of Crry gene in some progenies, leading to global Crry deletion.
Figure 28B:
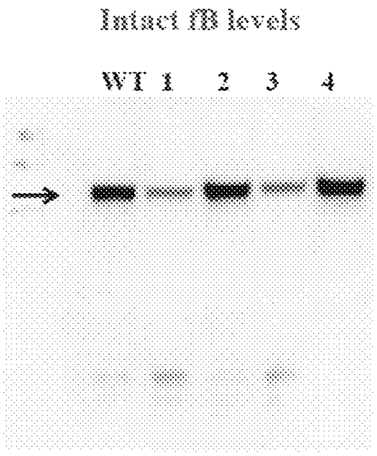
Figure 29:
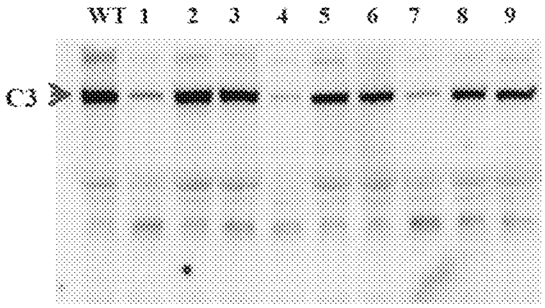
FIG. 29 provides a dosage comparison of AAV8-mfH1-4.678.19-20 gene therapy using C3 recovery as a readout. In this experiment, different doses of AAV8-mfH1-4.678.19-20 were administered to $fH^{m/m}$ mice (retro-orbital route, IV.). Two mice each was given the following dosages: $1\times10^{12}$ gene copies/mouse (M #1, M #2), $3\times10^{11}$ gene copies/mouse (M #3, M #6) and $1\times10^{11}$ gene copies/mouse (M #4, M #5). Western blot was performed to analyze plasma C3 levels before (Pre) and one week (1 W) or 1 month (1 M) after gene therapy. As shown, all doses tested were able to increase plasma C3 levels when examined at 1 W and 1 M time points.
Figure 31:
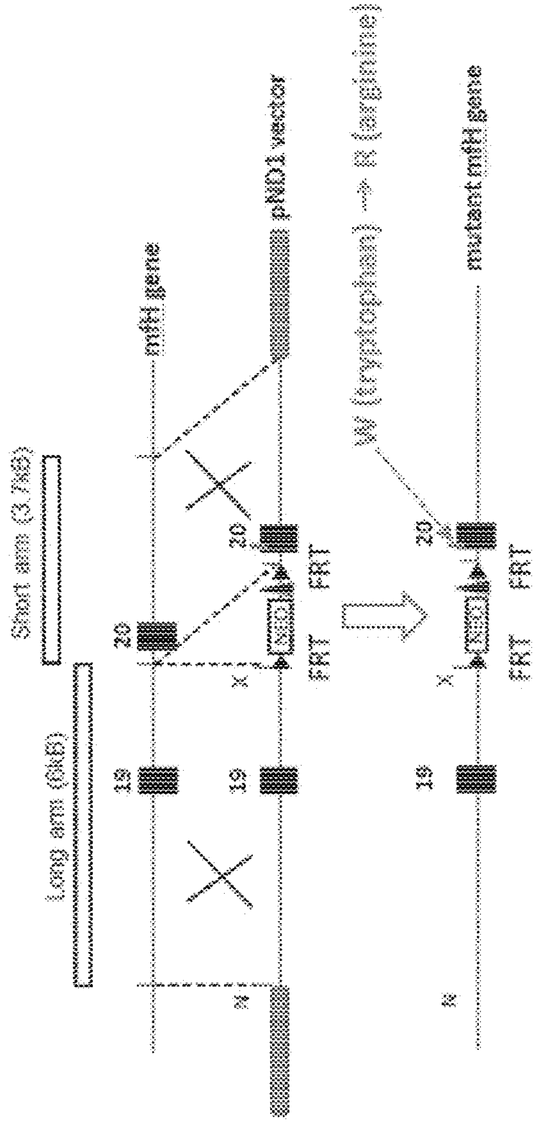
FIG. 31 is a schematic diagram showing the gene targeting strategy used to introduce a W to R mutation in SCR20 of mouse fH (position 1206, corresponding to position 1183 in human fH).
Figure 32:
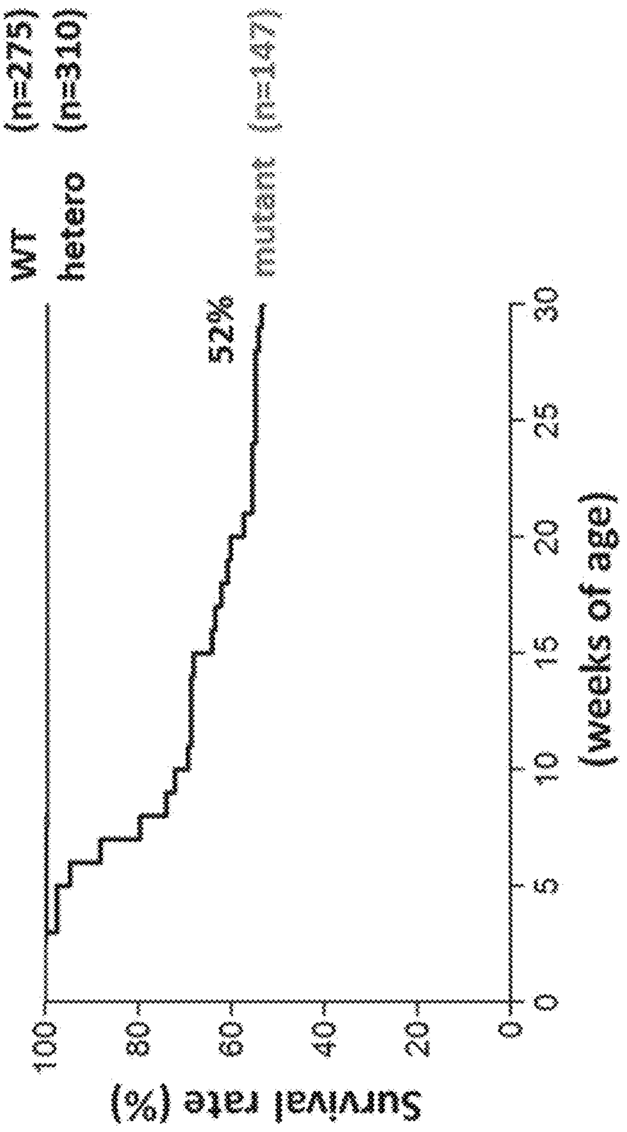
FIG. 32 shows the survival curves of wild-type littermate mice and mutant mice carrying W1206R mutation in fH. The fH mutant mice developed characteristic pathologies of aHUS and close to half of them died by 30 weeks of age.
Figure 33A:
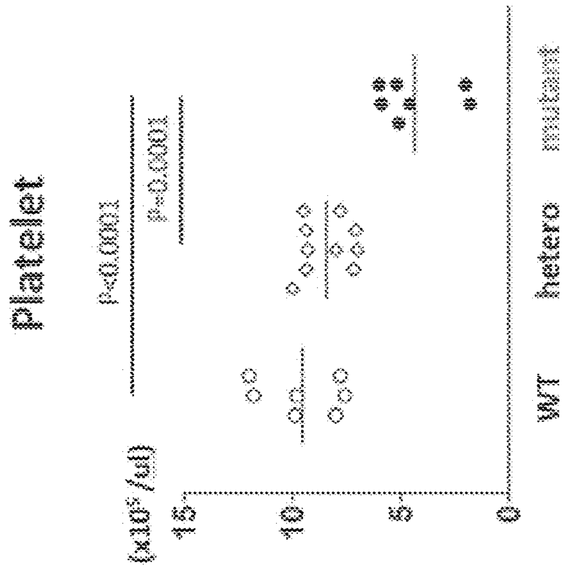
FIG. 33A shows a comparison of platelet counts in wild-type, heterozygous, and homozygous mutant mice. The homozygous mutant mice showed low platelet counts, suggesting that they were suffering from chronic thrombocytopenia.
Figure 33B:
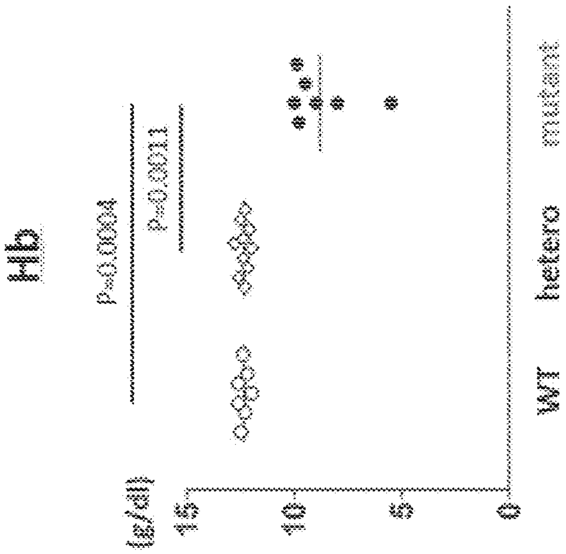
FIG. 33B shows a comparison of hemoglobin levels in wild-type, heterozygous, and homozygous mutant mice. The homozygous mutant mice show low hemoglobin levels, suggesting that they are suffering from chronic hemolytic anemia.
Figure 36:
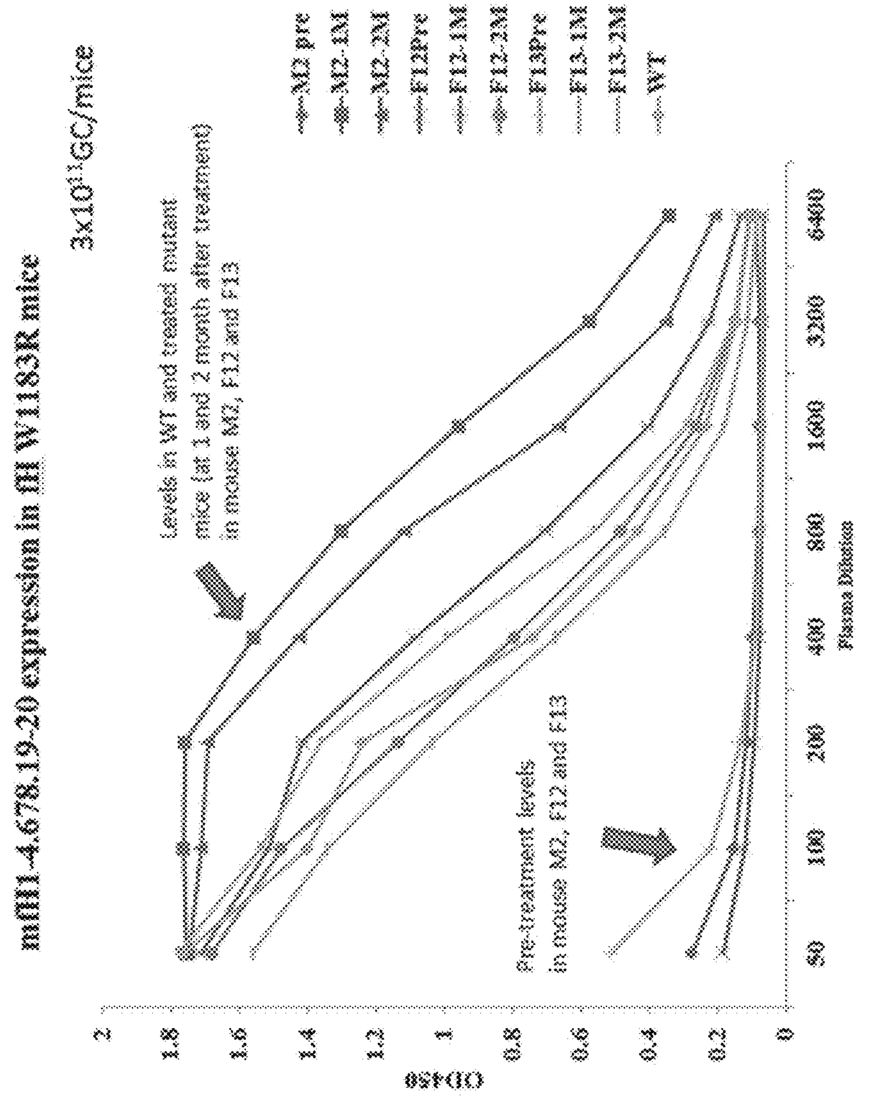
FIG. 36 shows that mfH1-4.678.19-20 protein was detected by ELISA in the blood of $fH^{W1206R/W1206R}$ mice at 1 month and 2 months after treatment with AAV8-mfH1-4.678.19-20 vector at $3\times10^{11}$ GC/mouse but not in the blood of these mice before AAV gene therapy.
Figures 37A, 37B:
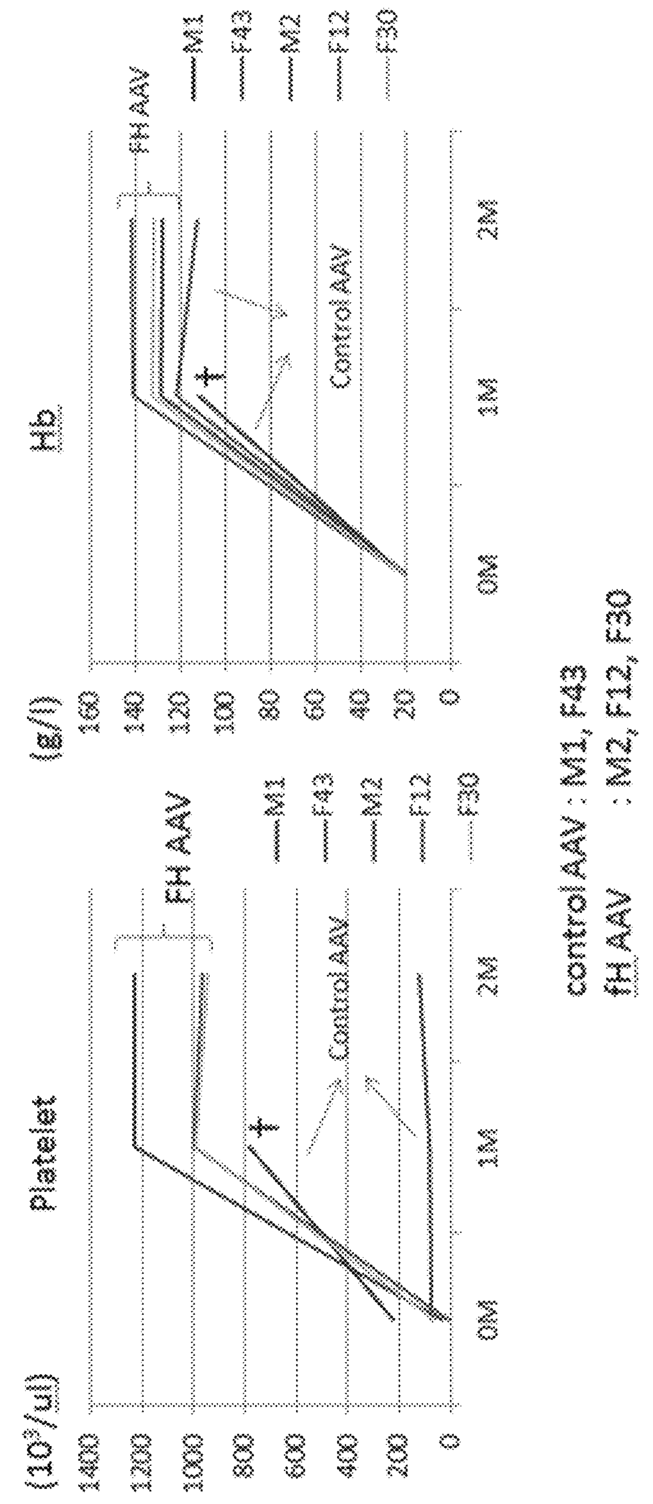
FIG. 37A and FIG. 37B are line graphs showing the treatment of $fH^{W1206R/W1206R}$ mice with AAV8-mfH1-4.678.19-20 vector at $3\times10^{11}$ GC/mouse normalized their platelet counts. All 3 $fH^{W1206R/W1206R}$ mice treated with AAV8-mfH1-4.678.19-20 were alive and healthy. Their platelet counts (FIG. 37A) and hemoglobin levels (Hb, FIG. 37B) increased and were maintained at normal range. In contrast, 1 of 2 $fH^{W1206R/W1206R}$ mice treated with control AAV vector died (at 4 weeks after treatment) and the remaining mouse had consistent low platelet counts and fluctuating hemoglobin level that was below that of mice treated with AAV8-mfH1-4.678.19-20.

As used herein, the term "treating complement associated disorders" includes alleviating, reducing, and/or ameliorating symptoms, both of the complement factor H disorders identified above, but also other disorders associated with uncontrolled alternative pathway complement regulation. More particularly, the data provided herein suggests that at least one AAV-mediated fH variant is broadly effective for complement-mediated diseases caused by uncontrolled alternative pathway complement regulation, irrespective of the underlying regulatory mechanism defect. See, e.g, FIG. 23.

"Complement-mediated disorders" may encompass symptoms associated with complement dysregulation which can manifest as several different phenotypes, including asymptomatic, recurrent bacterial infections, and various tissue injuries including but not limited to renal diseases. Unless otherwise specified, both homozygous subjects and heterozygous subjects are encompassed within this definition. Complement dysregulation is typically caused by loss of function mutations in, or autoantibodies against, complement regulatory proteins including but not limited to fH, factor I (fI) and membrane cofactor protein (MCP) or by gain of function mutations in other complement proteins including but not limited to C3 and factor B (fB). Complement dysregulation is typically, though not always, characterized by decreased serum levels of factor H, complement component C3, fB and a decrease in other terminal complement components, indicating activation of the alternative and/or the terminal complement pathway. Complement-mediated pathologies that can be treated by the present invention of composition and method include but are not limited to the following diseases with variable clinical presentation and progression: C3 glomerulopathy (formally called membranoproliferative glomerulonephritis type II or MPGNII), of which there are two known forms—dense deposit disease (DDD) and C3 glomerulonephritis (C3GN); thrombotic microangiopathy (TMA) including but not limited to atypical hemolytic uremic syndrome (aHUS), Shiga-like toxin-producing *E. coli* HUS (STEC-HUS) and thrombotic thrombocytopenia purpura (TTP); retinal degenerative eye disease including age related macular degeneration (AMD), RPE degeneration, chorioretinal degeneration, photoreceptor degeneration, paroxysmal nocturnal hemoglobinuria (PNH), ischemia reperfusion injury of all organs and settings, rheumatoid arthritis, hemodialysis, diabetic nephropathy, diabetic vasculopathy, asthma, systemic lupus erythematosus (SLE), ischemic stroke, abdominal aortic aneurysm (AAA), anti-neutrophil cytoplasmic antibody (ANCA) mediated vasculitis (ANCA vasculitis), ANCA-mediated hemorrhagic lung injury and disease, ANCA glomerulonephritis, graft versus host disease (GvHD), acute or delay graft rejection in organ transplantation, Crohn's disease, psoriasis, multiple sclerosis, anti-phospholipid syndrome, preeclampsia, atherosclerosis, neuromyelitis optica (NMO), autoimmune skin-blistering disease, Bullous pemphigoid (BP), Alzheimer's disease (AD), as well as bacterial infections caused by recruitment of bacterial pathogens (e.g., *Aspergillus* spp.; *Borrelia burgdorferi; B. duttonii; B. recurrentis; Candida albicans; Francisella tularensis; Haemophilus influenzae; Neisseria meningitidis; Streptococcus pyogenes*. Other examples of such disorders are discussed in more details below.

The amino acid sequence of the mature "wild-type" human complement factor H (isoform 1) is provided herein and serves as a reference for the amino acid numbering of the hfH isoform 1 [reproduced in SEQ ID NO: 39]. The leader sequence is located at amino acids 1 to 18 of factor H, with reference to SEQ ID NO: 39. The amino acid sequence of the leader is provided in SEQ ID NO: 2. The mature (secreted) hfH protein is located at amino acids 19 to 1231, with reference to SEQ ID NO: 39. There are alternative methods of determining the location of the 20 short complement repeats (SCRs). The location of the domains used in the experiments provided below is annotated in FIG. 1 and is based on the numbering used in C. Estaller et al, Eur J Immunol. 1991 March; 21(3):799-802.

The amino acid sequence of the wild-type human complement factor H, isoform 1, is reproduced in SEQ ID NO: 39. The features section of SEQ ID NO: 1 also illustrates an alternative system for identifying the start/stop of each of the 20 Short Consensus Repeat (SCR) domains. In this system, linker sequences are not present between each of the SCRs.

Optionally, an engineered hfH variant provided herein may have a heterologous leader sequence substituted for the native hfH leader sequence. In the following descriptions, substitutions may be written as (first amino acid identified by single letter code)—residue position #—(second amino acid identified by single letter code) whereby the first amino acid is the substituted amino acid and the second amino acid is the substituting amino acid at the specified position with reference to isoform 1; however, by conventional alignment steps, the corresponding amino acid residues identified herein with respect to the numbering of isoform 1 can be located in isoform 2 and non-disease causing natural variants of the SCRs of isoform 1 or 2 of fH.

As used herein, when reference is made to SCR #-##, the domains are inclusive of the endpoints and is the same as "SCR #, . . . SCR ##". In certain embodiments, periods are used between the domains. For example, SCR1-4, refers to "SCR1, SCR2, SCR3, and SCR4" and is the same as "SCR1,2,3,4" or "SCR1.2.3.4.". SCR19-20, refers to SCR19 and SCR20 and is the same as "SCR19,20". For example, "SCR6-8", "SCR6.7.8" and "SCR6,7,8" refer to the same domains.

Figure 6:
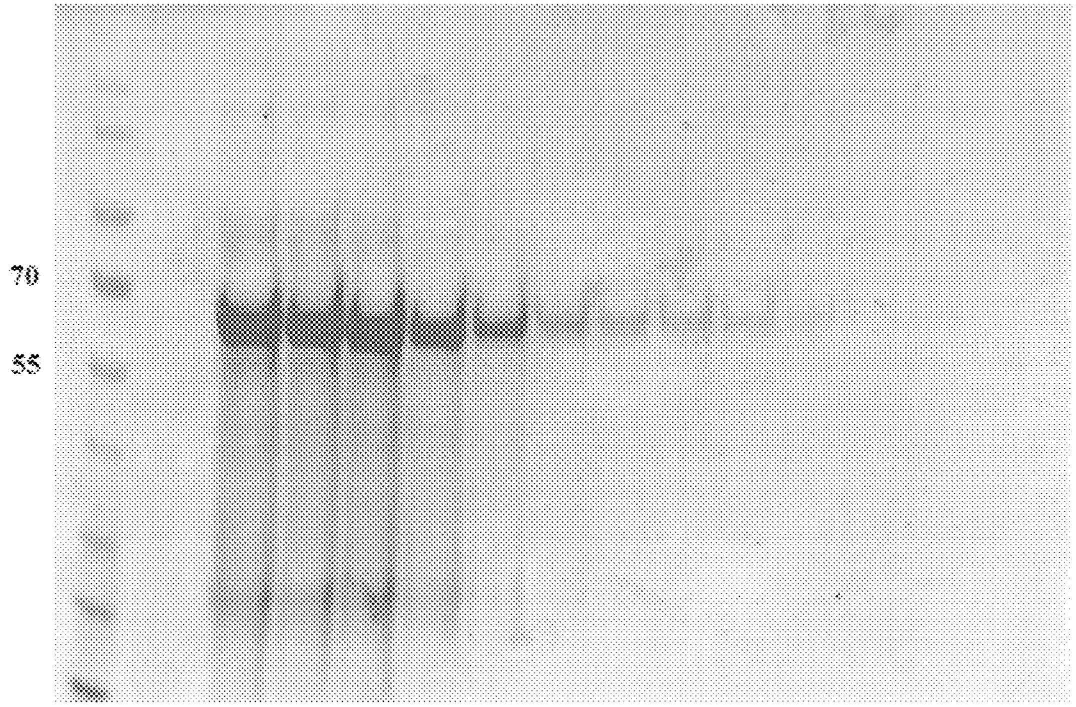
FIG. 6 is an SDS-gel which shows purification of recombinant hfH1-4.678.19-20. SDS-gel analysis was performed via Coomasie blue staining of human fH truncation variant containing SCR1-4, 6-8, and 19-20 that was expressed by transfecting HEK cells using the pCBARBG vector. The recombinant fH truncation protein was purified from the supernatant by passing through an affinity column that was prepared using a mAb against human factor H (clone OX-23) that recognizes an epitope in SCR2-3. Size and location of protein molecular weight markers are shown on the left side.
Figure 7:
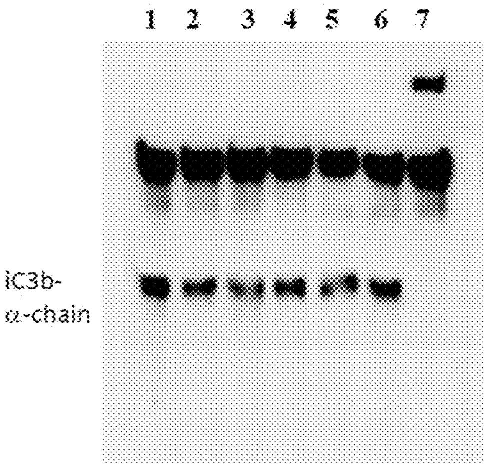
FIG. 7 is a gel showing recombinant hfH1-4.678.19-20 retains complement regulating activity (cofactor activity). The human fH truncation variant containing SCR1-4, 6-8, and 19-20 was tested for cofactor activity for factor I-mediated C3b cleavage. For this assay, human C3b was mixed with factor I in the presence (Lane 1-6) or absence (Lane 7) of full-length fH (hfH) or the truncated fH variant (hfH1-4.678.19-20). The reaction mixture was incubated and then analyzed by SDS-PAGE and western blot analysis. Cofactor activity is indicated by the appearance of the iC3b $\alpha$-chain fragment.
Figure 8:
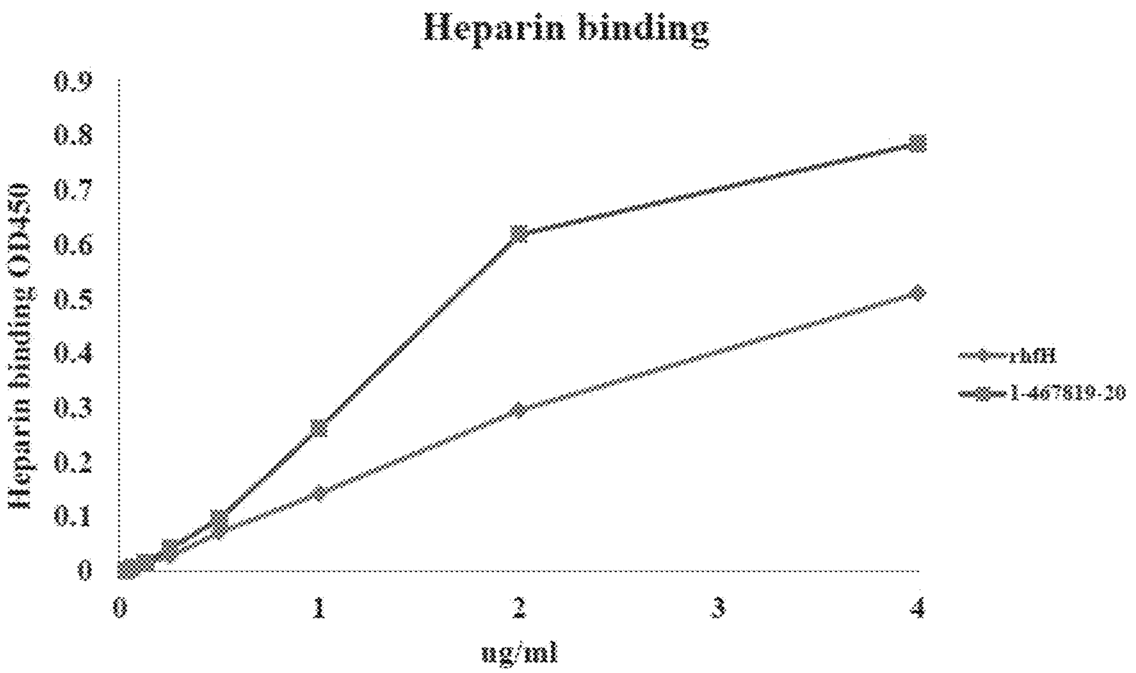
FIG. 8 is a line graph showing that recombinant hfH1-4.678.19-20 (square, top line) has strong heparin-binding activity. The human fH truncation variant containing SCR1-4, 6-8, and 19-20 retains heparin-binding activity. Its heparin-binding activity is dose-dependent, and when compared with full-length human fH (diamond, lower line) on a μg/ml basis, it showed higher activity. Heparin-binding activity was assessed by ELISA using plate-coated heparin, overlay of a full-length or truncated fH protein solution and, after washing, detection of bound fH or truncated fH by the mAb OX-23 (against an epitope in SCR2-3).
Figure 9:
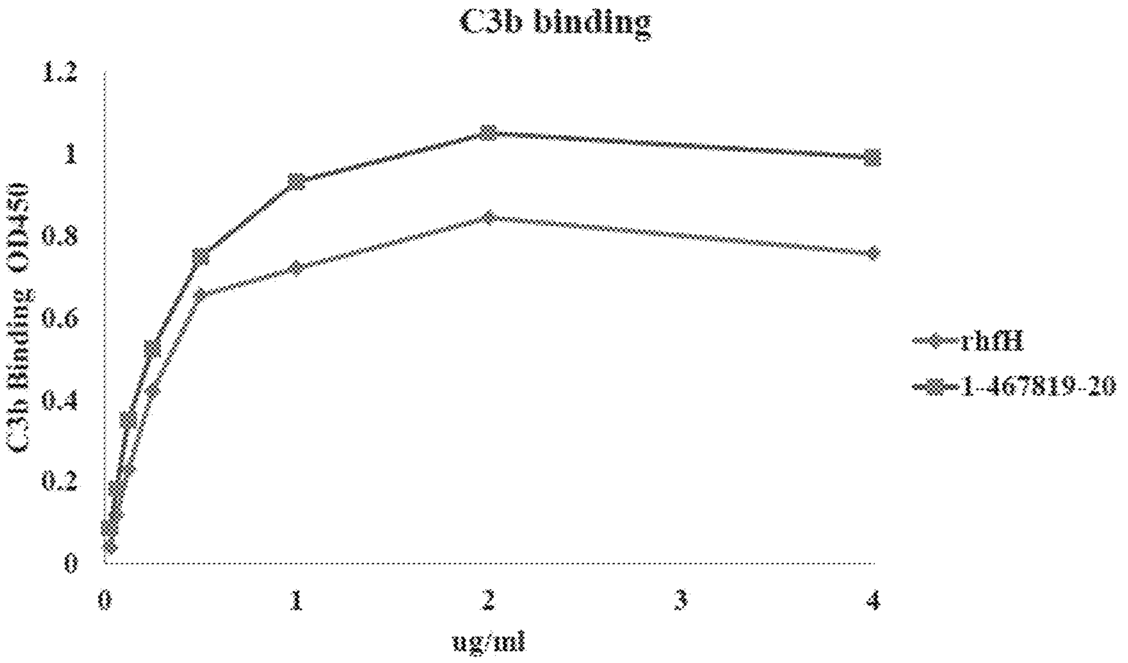
FIG. 9 is a line graph showing recombinant hfH1-4.678.19-20 (square, top line) has strong C3b-binding activity. The human fH truncation variant containing SCR1-4, 6-8, and 19-20 retains C3b-binding activity. Its C3b-binding activity is dose-dependent, and when compared with full-length human fH (diamond, bottom line) on a μg/mL basis, it showed higher activity. C3b-binding activity was assessed by ELISA using plate-coated C3b, overlay of a full-length or truncated fH protein solution and, after washing, detection of bound fH or truncated fH by the mAb OX-23 (against an epitope in SCR2-3).
Figure 10:
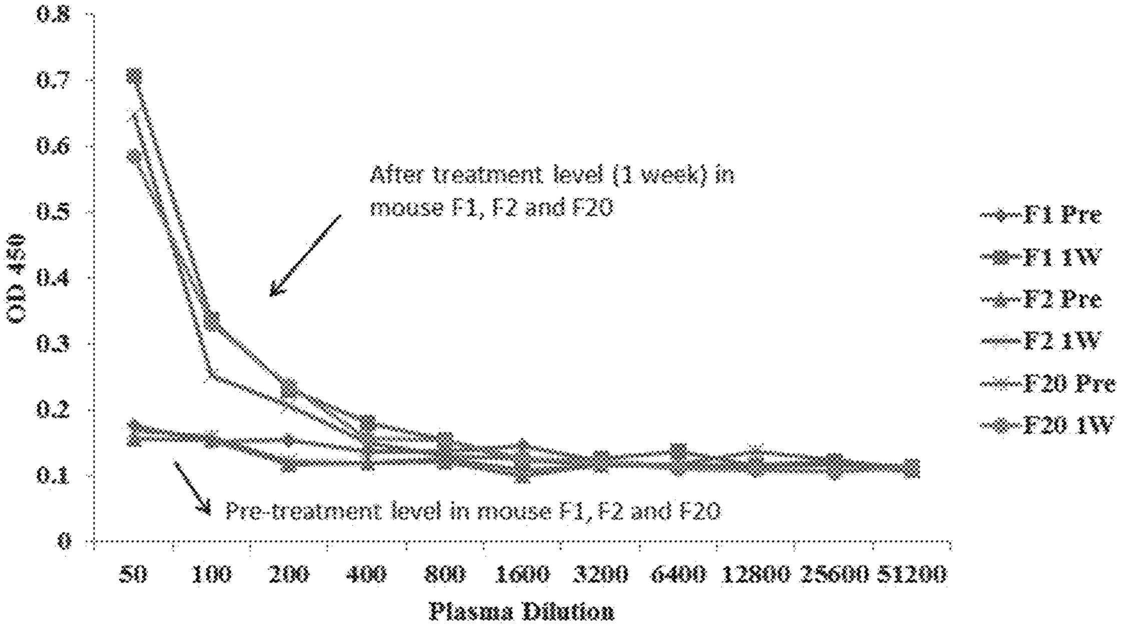
FIG. 10 is a line graph showing ELISA detection of hfH1-4.678.19-20 in the blood of 3 different fH mutant mice ($fH^{m/m}$; F1, F2, F20) one week after AAV8-mediated fH gene therapy. The $fH^{m/m}$ mouse is a strain of fH mutant mice that carry premature stop codons at the beginning of SCR19. These mice produce trace amount of truncated fH (lacking SCR19-20) and has uncontrolled fluid phase alternative pathway complement activation and consumption (secondary C3 and fB deficiency). Mice were infected by retro-orbital I.V. with an AAV8 virus containing hfH1-4.678.19-20 ($3\times10^{11}$ gene copies/mouse) and after one week, blood samples were collected and processed for human fH protein detection. For ELISA assay, the mAb OX-23 was used as a capture antibody (recognizing an epitope in human fH SCR2-3) and biotinylated mAb L20/3 was used as a detection antibody (recognizing human fH SCR19). As shown in the figure, there is no hfH1-4.678.19-20 in the blood of 3 $fH^{m/m}$ mice (F1, F2, F20) before AAV-hfH1-4.678.19-20 treatment (Pre), but hfH1-4.678.19-20 was detected one week (1 W) after treatment.
Figure 11:
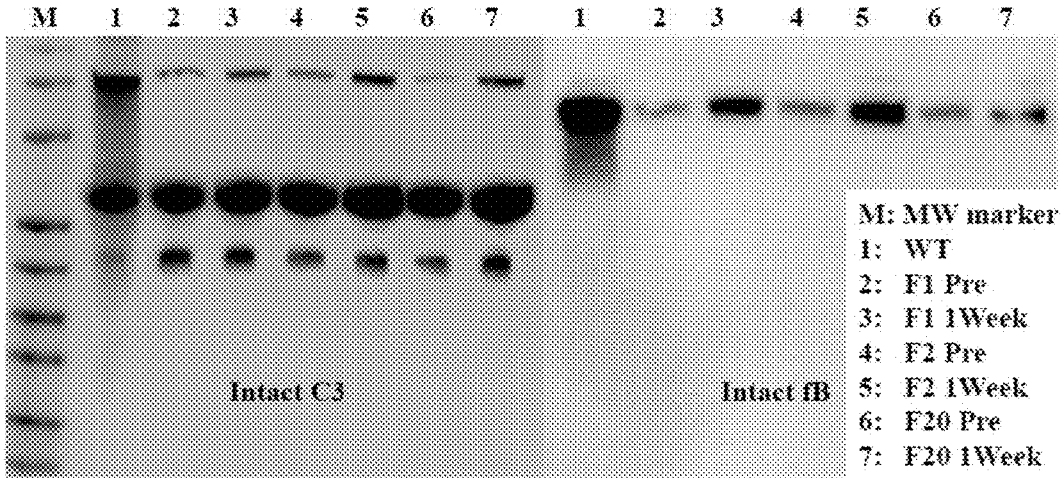
FIG. 11 is western blot analysis demonstrating that AAV8-mediated human fH gene therapy in $fH^{m/m}$ mice inhibits alternative pathway complement activation due to the lack of sufficient endogenous mouse fH expression, untreated $fH^{m/m}$ mice have uncontrolled fluid phase alternative pathway complement activation, and as a result they consume plasma C3 and fB (compare Lane 1 of WT with Lanes 2, 4, 6 of three $fH^{m/m}$ mice before gene therapy). One week after $fH^{m/m}$ mice were treated with AAV8-hfH1-4.678.19-20, plasma C3 and fB levels significantly increased compared with pre-treatment levels, suggesting that AAV8-mediated human fH gene therapy inhibited uncontrolled alternative pathway complement activation and C3 and fB consumption. All three mice (F1, F2 and F20) received $3\times10^{11}$ gene copies each via retro-orbital I.V..
Figure 12A:
FIG. 12A provides a schematic domain structure of human factor H variant containing SCR1-4, 6-8, and 17-20, with the locations of N-glycosylations sites illustrated by arrows.
Figure 15A:
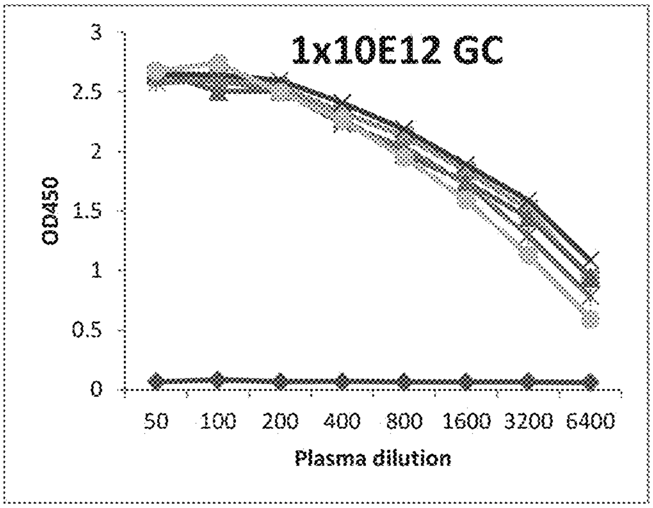
FIG. 15A-FIG. 15C show ELISA detection of hfH1-4.6-8.17-20 protein level in the plasma of 3 fH mutant mice treated with varying doses of AAV8-hfH1-4.678.17-20. The $fH^{m/m}$ mouse is a strain of fH mutant mice that carry premature stop codons at the beginning of SCR19. These mice produce trace amount of truncated fH (lacking SCR19-20) and has uncontrolled fluid phase alternative pathway complement activation and consumption (secondary C3 and fB deficiency). Mice were infected by retro-orbital I.V. with a AAV8 virus containing hfH11-4.678.17-20 at three doses, $1\times10^{12}$ gene copies (GC)/mouse (FIG. 15A), $3\times10^{11}$ GC/mouse (FIG. 15B), and $1\times10^{11}$ GC/mouse (FIG. 15C), respectively. Plasma samples were collected for ELISA assay before AAV treatment (Pre) or at one week (W1), two weeks (W2), one month (M1), two months (M2) or 3 months (M3) after AAV treatment. For ELISA assay, the mAb OX-23 was used as a capture antibody (recognizing an epitope in human fH SCR2-3) and biotinylated mAb L20/3 was used as a detection antibody (recognizing human fH SCR19). As shown in the figure, there is no hfH11-4.678.17-20 in the blood of $fH^{m/m}$ mice before AAV-hfH1-4.678.17-20 treatment (Pre), but high level of hfH1-4.678.17-20 was detected after AAV treatment and hfH1-4.678.17-20 expression remained stable for at least 3 months.
Figure 15B:
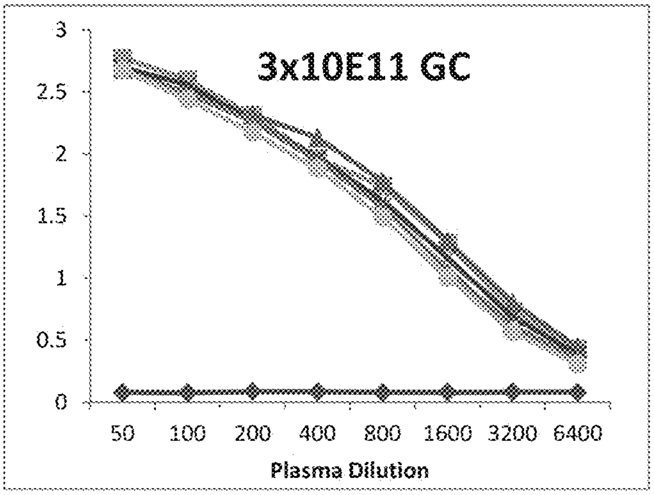
Figure 15C:
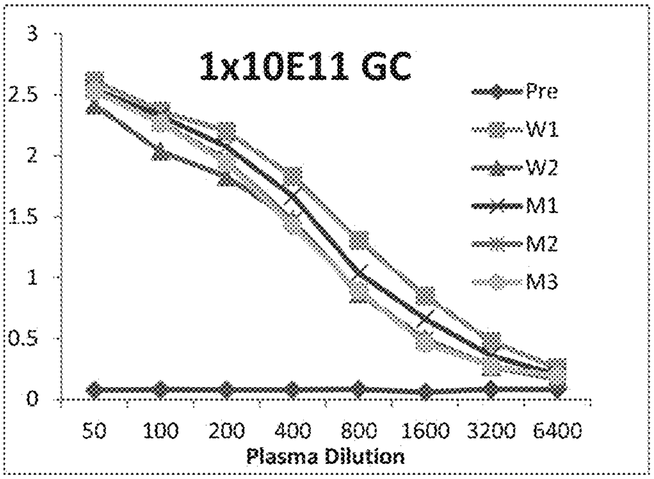
Figure 16A:
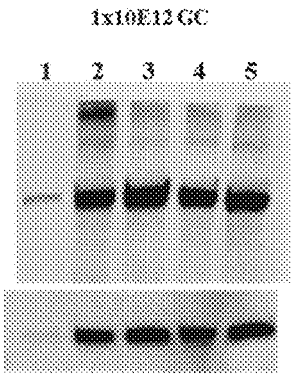
FIG. 16A-FIG. 16C are western blot analysis demonstrating that treatment with AAV8-hfH1-4.678.17-20 gene therapy of $fH^{m/m}$ mice inhibits alternative pathway complement activation. Due to the lack of sufficient endogenous mouse fH expression, untreated $fH^{m/m}$ mice have uncontrolled fluid phase alternative pathway complement activation, and as a result they consume plasma C3 and fB (Lane 1). In three $fH^{m/m}$ mice treated with $1\times10^{12}$ gene copies (GC)/mouse (FIG. 16A), $3\times10^{11}$ gene copies (GC)/mouse (FIG. 16B) and $1\times10^{11}$ gene copies (GC)/mouse (FIG. 16C), respectively, through retro-orbital I.V., alternative pathway complement activation was prevented with corresponding recovery of plasma C3 and fB when the treated mice were examined at one week (W1), one month (M1), 2 months (M2) and 3 months (M3) after AAV8-hfH1-4.678.17-20 gene therapy. In every treatment dosage and time point (Lanes 2, 3, 4, 5), plasma C3 and fB were markedly higher after AAV8-hfH11-4.678.17-20 gene therapy than before treatment (Pre, Lane 1).
Figure 16B:
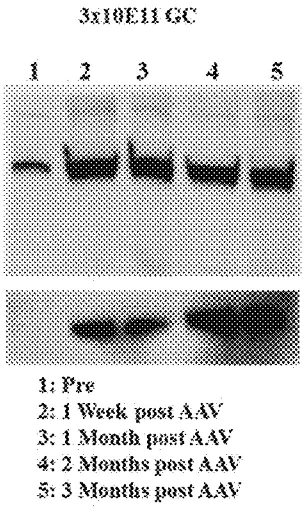
Figure 16C:
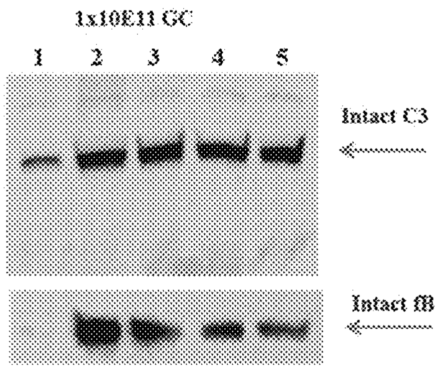

As used herein, the term "functional fH variant" includes fH variants which are characterized by having complement regulating activity (cofactor activity) located in SCR1-4 and optionally, a functional C3b-binding and GAG-binding ability (located within wild-type SCR7 and SCR19-20) characteristic of wild-type fH. In some embodiments, the engineered fH variants have more than 100% of wild-type fH cofactor activity and/or GAG-binding ability. See, e.g., FIG. 8 and the examples below which demonstrate that a fH variant described herein has GAG- and C3b-binding activity statistically higher than full-length human fH, e.g., about 10% to 40% higher. In another embodiment, the engineered fH variant has less than about 95% to about 100% of wild-type functional fH. For example, an engineered fH variant may have at least 50% of the cofactor activity present in functional wild-type fH, and more desirably at least about 60%, at least about 75%, at least about 80%, at least about 85%, at least about 90%, at least about 95%, or at least about 99%. In another embodiment, the engineered fH variant may alternatively or additionally have at least at least 50% of the GAG-binding ability of functional fH, and more desirably at least about 60%, at least about 75%, at least about 80%, at least about 85%, at least about 90%, at least about 95%, or at least about 99%. Methods of determining cofactor activity, binding and/or determining increased circulating half-life as compared to the hfH proteins are known in the art, and at least one these assays is illustrated in the examples below.

Examples of functional fH variants include those having SCR1-4 and 19-20 of the fH protein, with one or more of an SCR7, SCR17 or SCR18 domain. Further variants include those having one or more of SCR6, SCR8, SCR16, SCR17, SCR18, or fragments thereof, and combinations thereof. For example, such variants may include, e.g., fH SCR1-4, 6-8, 19-20; fH SCR1-4, 6-8, 18-20; fH SCR1-4, 6-8, 17-20; fH SCR1-4, 6-7, 19-20; fH SCR1-4,6-7, 18-20; fH SCR1-4, 6-7, 17-20; fH SCR1-4, 7-8, 19-20; fH SCR1-4, 7-8, 18-20; fH SCR1-4, 7-8, 17-20; fH SCR1-4, 7, 19-20; fH SCR1-4, 7, 18-20; fH SCR1-4, 7, 17-20; SCR1-4, 17, 19-20; SCR1-4, 18-20; SCR1-4, 17-20 and/or fH SCR1-4, 7, 16-20, among others. In certain embodiments, the hfH variant further comprises additional hfH SCRs, e.g., SCR 6, SCR8, SCR16, or combinations thereof. In preferred embodiments, hfH SCR5 is absent. However, in certain embodiments, hfH SCR5 may be present in whole or a fraction thereof. In certain embodiments, hfH SCR9, SCR10, SCR11, SCR12, SCR13, SCR14, and/or SCR15 are absent, or are at least functionally deleted. Optionally, one or more of the SCRs in these variants may be a "functional fragment" of the SCRs, rather than a full-length SCR as shown in FIG. 1 or the features of SEQ ID NO: 1. By "functional fragment" is meant an amino acid sequence (or coding sequence therefor) less than the full-length SCR which is characterized by having one or more of complement inhibiting activity, the ability to bind, heparin, and/or C3b-binding activity.

These and other variants may include other fH sequences. For example, when expressed from a viral vector the coding sequence of the fH variant also includes a leader sequence. Such a leader sequence may be an fH leader. Optionally, the leader sequence can be from another source, e.g., an IL-2 leader. In one embodiment, the leader sequence selected is less than about 26 amino acids in length (e.g., from about 1 to about 26 amino acids), more preferably less than 20 amino acids (from about 1 to about 20 amino acids), and most preferably, less than about 18 amino acids in length (from about 1 to about 18 amino acids). By "functional deletion" is meant an amino acid sequence (or coding sequence therefor) which lacks complement inhibiting activity, the C3b-binding activity, and optionally also further lacks heparin binding activity.

With the variants, domains may be located immediately adjacent to one another (e.g., the carboxy terminus of one domain may immediately follow the amino terminus of the preceding domain). Alternatively, one or more of the SCR domains may have a linker composed of one to about 12 to 18 amino acids located between them. For example, a variant may contain SCR1—(L1)—SCR2—(L2)—SCR3—(L3)—SCR4—(L4)—(SCR6—(L4'))—SCR7—(L5)—(SCR8—(L5'))—(SCR16—(L5''))—(SCR17—(L5'''))—(SCR18—(L5''''))—SCR19—(L6)—SCR20, wherein the ( ) indicate optional component, "L" refers to a linker, and each of L1, L2, L3, L4, L4', L5, L5', L5'', L5''', L5'''', and L6 may be absent or independently selected from an amino acid sequence of about 1 to about 12-18 amino acids. In other words, where a variant contains multiple linkers, each of the linkers may have the same sequence or a different sequence. In certain embodiments, a variant contains at least one, at least two, at least three, at least four, at least five linkers, at least six linkers. Examples of suitable linkers include the natural linkers identified in FIG. 1 or FIG. 17, SEQ ID NO: 4, 6, 8, 10, 12, 15, 18, 20, 22, 24, 26, 28, 30, 32, 34 and 36, or synthetic linkers. Each of these wild-type linkers may be located in their native position. Alternatively, one or more of these wild-type linkers may be used in a different linker position, or in multiple different linker positions.

Optionally, one or more of these linkers may be fH sequences and are independently selected. Alternatively, one or more of the linkers may be heterologous to fH, e.g., from a different source, whether artificial, synthetic, or from a different protein which confers suitable flexibility to the fH variant. Examples of other suitable linkers may include, e.g., a poly Gly linker and other linkers providing suitable flexibility. In certain embodiments, the linkers lack any fH function.

The term "amino acid substitution" and its synonyms described above are intended to encompass modification of an amino acid sequence by replacement of an amino acid with another, substituting, amino acid. The substitution may be a conservative substitution. It may also be a non-conservative substitution. The term conservative, in referring to two amino acids, is intended to mean that the amino acids share a common property recognized by one of skill in the art. For example, amino acids having hydrophobic nonacidic side chains, amino acids having hydrophobic acidic side chains, amino acids having hydrophilic nonacidic side chains, amino acids having hydrophilic acidic side chains, and amino acids having hydrophilic basic side chains. Common properties may also be amino acids having hydrophobic side chains, amino acids having aliphatic hydrophobic side chains, amino acids having aromatic hydrophobic side chains, amino acids with polar neutral side chains, amino acids with electrically charged side chains, amino acids with electrically charged acidic side chains, and amino acids with electrically charged basic side chains. Both naturally occurring and non-naturally occurring amino acids are known in the art and may be used as substituting amino acids in embodiments. Methods for replacing an amino acid are well known to the skilled in the art and include, but are not limited to, mutations of the nucleotide sequence encoding the amino acid sequence. Reference to "one or more" herein is intended to encompass the individual embodiments of, for example, 1, 2, 3, 4, 5, 6, or more.

In addition to the fH protein variants provided herein, nucleic acid sequences encoding these fH protein variants are provided. The coding sequences for these variants may be from wild-type sequences of the leader sequence and/or one or more SCRs of isoform 1, isoform 2, or non-disease associated variants. Alternatively or additionally, web-based or commercially available computer programs, as well as service based companies may be used to back translate the amino acids sequences of the leader sequence, and/or one or more of the SCRs to nucleic acid coding sequences, including both RNA and/or cDNA. See, e.g., backtranseq by EMBOSS; Gene Infinity; and ExPasy. In one embodiment, the RNA and/or cDNA coding sequences are designed for optimal expression in human cells.

Codon-optimized coding regions can be designed by various different methods. This optimization may be performed using methods which are available on-line, published methods, or a company which provides codon optimizing services. One codon optimizing method is described, e.g., in WO 2015/012924 A2, which is incorporated by reference herein. Briefly, the nucleic acid sequence encoding the product is modified with synonymous codon sequences. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

The terms "percent (%) identity", "sequence identity", "percent sequence identity", or "percent identical" in the context of nucleic acid sequences refers to the bases in the two sequences which are the same when aligned for correspondence. The length of sequence identity comparison may be over the full-length of the genome, the full-length of a gene coding sequence, or a fragment of at least about 500 to 5000 nucleotides, or as desired. However, identity among smaller fragments, e.g. of at least about nine nucleotides, usually at least about 20 to 24 nucleotides, at least about 28 to 32 nucleotides, at least about 36 or more nucleotides, may also be desired. Multiple sequence alignment programs are also available for nucleic acid sequences. Examples of such programs include, "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 32 amino acids, about 330 amino acids, or a peptide fragment thereof or the corresponding nucleic acid sequence coding sequencers. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

In one embodiment, the nucleic acid sequences encoding the fH variants (e.g., hfH variant gene) described herein are engineered into any suitable genetic element, e.g., naked DNA, phage, transposon, cosmid, RNA molecule (e.g., mRNA), episome, etc., which transfers the hfH sequences carried thereon to a host cell, e.g., for generating nanoparticles carrying DNA or RNA, viral vectors in a packaging host cell and/or for delivery to a host cells in subject. In one embodiment, the genetic element is a plasmid. The selected genetic element may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, NY (2012).

As used herein, an "expression cassette" refers to a nucleic acid molecule which comprises the hfH variant coding sequences, promoter, and may include other regulatory sequences therefor (e.g., 5' and/or 3' UTR sequences), which cassette may be engineered into a genetic element and/or packaged into the capsid of a viral vector (e.g., a viral particle). Typically, such an expression cassette for generating a viral vector contains the hfH sequences described herein flanked by packaging signals of the viral genome and other expression control sequences such as those described herein.

The expression cassette typically contains a promoter sequence as part of the expression control sequences. The illustrative plasmid and vector described herein uses the chicken beta-actin. Alternatively, another constitutive promoter may be selected. In certain embodiments, de-targeting of undesirable target cells may be achieved by use of appropriate vector elements, e.g., microRNAs. Additionally or alternatively, the vector selected may have preferential targeting for the desired tissue, e.g., an AAV8, AAV9, or AAVrh10 for liver, an AAV8, AAV1, or other AAV for eye, or the like.

However, targeting the vector to a desired tissue may be desirable for maximizing expression of the protein. And as such, a liver-specific promoter may be selected. Examples of suitable promoters include, thyroxin binding globulin (TBG), alpha 1 antitrypsin (A1AT); human albumin Miyatake et al., J. Virol., 71:5124 32 (1997), humAlb; and hepatitis B virus core promoter, Sandig et al., Gene Ther., 3:1002 9 (1996)]. TTR minimal enhancer/promoter, alpha-antitrypsin promoter, LSP (845 nt) 25 (requires intron-less scAAV). Alternatively, other liver-specific promoters may be used (see, e.g., The Liver Specific Gene Promoter Database, Cold Spring Harbor). Alternatively, where targeting to another tissue is desired, a different tissue-specific promoter may be selected. The promoter may be derived from any species. For example, for use in the eye, e.g., a retinal pigmented epithelium (RPE) promoter or a photoreceptor promoter may be selected. In another embodiment, the promoter is the human G-protein-coupled receptor protein kinase 1 (GRK1) promoter (Genbank Accession number AY327580). In another embodiment, the promoter is a 292 nt fragment (positions 1793-2087) of the GRK1 promoter (See also, Beltran et al, Gene Therapy 2010 17:1162-74, which is hereby incorporated by reference herein). In another preferred embodiment, the promoter is the human interphotoreceptor retinoid-binding protein proximal (IRBP) promoter. In another embodiment, promoter is the native promoter for the gene to be expressed. In one embodiment, the promoter is the RPGR proximal promoter (Shu et al, IOVS, May 2012, which is incorporated by reference herein). Other promoters useful in the invention include, without limitation, the rod opsin promoter, the red-green opsin promoter, the blue opsin promoter, the cGMP-β-phosphodiesterase promoter, the mouse opsin promoter (Beltran et al 2010 cited above), the rhodopsin promoter (Mussolino et al, Gene Ther, July 2011, 18(7):637-45); the alpha-subunit of cone transducin (Morrissey et al, BMC Dev, Biol, January 2011, 11:3); beta phosphodiesterase (PDE) promoter; the retinitis pigmentosa (RP1) promoter (Nicord et al, J. Gene Med, December 2007, 9(12):1015-23); the NXNL2/NXNL1 promoter (Lambard et al, PLoS One, October 2010, 5(10):e13025), the RPE65 promoter; the retinal degeneration slow/peripherin 2 (Rds perph2) promoter (Cai et al, Exp Eye Res. 2010 August; 91(2):186-94); and the VMD2 promoter (Kachi et al, Human Gene Therapy, 2009 (20:31-9)). Examples of photoreceptor specific promoters include, without limitation, the rod opsin promoter, the red-green opsin promoter, the blue opsin promoter, the inter photoreceptor binding protein (IRBP) promoter and the cGMP-β-phosphodiesterase promoter. Alternatively, other promoters, such as viral promoters, constitutive promoters, regulatable promoters [see, e.g., WO 2011/126808 and WO 2013/04943], or a promoter responsive to physiologic cues may be used may be utilized in the vectors described herein.

In addition to a promoter, an expression cassette and/or a vector may contain other appropriate transcription initiation, termination, enhancer sequences, efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product. Examples of suitable polyA sequences include, e.g., SV40, bovine growth hormone (bGH), rabbit beta globulin, and TK polyA. Examples of suitable enhancers include, e.g., the alpha fetoprotein enhancer, the TTR minimal promoter/enhancer, LSP (TH-binding globulin promoter/alpha1-microglobulin/bikunin enhancer), amongst others.

These control sequences are "operably linked" to the fH gene sequences. As used herein, the term "operably linked" refers to both expression control sequences that are contiguous with the gene of interest and expression control sequences that act in trans or at a distance to control the gene of interest.

The expression cassette may be engineered onto a plasmid which is used for drug delivery or for production of a viral vector. Suitable viral vectors are preferably replication-defective and selected from amongst those which target ocular cells. Viral vectors may include any virus suitable for gene therapy may be used, including but not limited to adenovirus; herpes virus; lentivirus; retrovirus; parvovirus, etc.

Suitably, where one of these vectors is generated, it is produced as a replication-defective viral vector. A "replication-defective virus" or "viral vector" refers to a synthetic or recombinant viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

In one embodiment, the viral vector is an adeno-associated virus (AAV). An adeno-associated virus (AAV) viral vector is an AAV DNase-resistant particle having an AAV protein capsid into which is packaged nucleic acid sequences for delivery to target cells. An AAV capsid is composed of 60 capsid protein subunits, VP1, VP2, and VP3, that are arranged in an icosahedral symmetry in a ratio of approximately 1:1:10 to 1:1:20, depending upon the selected AAV.

The studies described herein utilize AAV8 as an illustrative vector. As used herein, "AAV8 capsid" refers to the AAV8 capsid having the encoded amino acid sequence of GenBank accession:YP_077180, which is incorporated by reference herein. Some variation from this encoded sequence is encompassed by the present invention, which may include sequences having about 99% identity to the referenced amino acid sequence in GenBank accession: YP_077180; U.S. Pat. Nos. 7,282,199, 7,790,449; 8,319,480; 8,962,330; 8,962,332, (i.e., less than about 1% variation from the referenced sequence). In another embodiment, the AAV8 capsid may have the VP1 sequence of the AAV8 variant described in WO2014/124282, which is incorporated by reference herein. Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003), US 2013/0045186A1, and WO 2014/124282. In certain embodiments, an AAV8 variant which shows tropism for the desired target cell, e.g., liver, photoreceptors, RPE or other ocular cells is selected. For example, an AAV8 capsid may have Y447F, Y733F and T494V mutations (also called "AAV8 (C&G+T494V)" and "rep2-cap8 (Y447F+733F+T494V)"), as described by Kay et al, Targeting Photoreceptors via Intravitreal Delivery Using Novel, Capsid-Mutated AAV Vectors, PLoS One. 2013; 8(4): e62097. Published online 2013 Apr. 26, which is incorporated herein by reference. See, e.g., Mowat et al, Tyrosine capsid-mutant AAV vectors for gene delivery to the canine retina from a subretinal or intravitreal approach, Gene Therapy 21, 96-105 (January 2014), which is incorporated herein by reference. In another embodiment, the AAV capsid is an AAV8 bp capsid, which preferentially targets bipolar cells. See, WO 2014/024282, which is incorporated herein by reference.

Other AAV serotypes may be selected as sources for capsids of AAV viral vectors (DNase resistant viral particles) including, e.g., AAV1, AAV2, AAV3, AAV4, AAV5, AAV6, AAV6.2, AAV7, AAV8, AAV9, rh10, AAVrh64R1, AAVrh64R2, rh8 [See, e.g., US Published Patent Application No. 2007-0036760-A1; US Published Patent Application No. 2009-0197338-A1; EP 1310571]. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), and WO 2006/110689], and rh10 [WO 2003/042397], variants thereof, or yet to be discovered, or a recombinant AAV based thereon, may be used as a source for the AAV capsid. These documents also describe other AAV which may be selected for generating AAV and are incorporated by reference. In some embodiments, an AAV cap for use in the viral vector can be generated by mutagenesis (i.e., by insertions, deletions, or substitutions) of one of the aforementioned AAV Caps or its encoding nucleic acid. In some embodiments, the AAV capsid is chimeric, comprising domains from two or three or four or more of the aforementioned AAV capsid proteins. In some embodiments, the AAV capsid is a mosaic of VP1, VP2, and VP3 monomers from two or three different AAVs or recombinant AAVs. In some embodiments, a rAAV composition comprises more than one of the aforementioned Caps.

For packaging an expression cassette into virions, the ITRs are the only AAV components required in cis in the same construct as the gene. In one embodiment, the coding sequences for the replication (rep) and/or capsid (cap) are removed from the AAV genome and supplied in trans or by a packaging cell line in order to generate the AAV vector. For example, as described above, a pseudotyped AAV may contain ITRs from a source which differs from the source of the AAV capsid. Additionally or alternatively, a chimeric AAV capsid may be utilized. Still other AAV components may be selected. Sources of such AAV sequences are described herein and may also be isolated or obtained from academic, commercial, or public sources (e.g., the American Type Culture Collection, Manassas, VA). Alternatively, the AAV sequences may be obtained through synthetic or other suitable means by reference to published sequences such as are available in the literature or in databases such as, e.g., GenBank®, PubMed®, or the like.

The minimal sequences required to package an expression cassette into an AAV viral particle are the AAV 5' and 3' ITRs, which may be of the same AAV origin as the capsid, or which are of a different AAV origin (to produce an AAV pseudotype). In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. Typically, an expression cassette for an AAV vector comprises an AAV 5' ITR, the coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used.

The abbreviation "sc" refers to self-complementary. "Self-complementary AAV" refers a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/110689; and U.S. Pat. No. 7,588,772 B2]. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus ULS, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065. See generally, e.g., Grieger & Samulski, 2005, "Adeno-associated virus as a gene therapy vector: Vector development, production and clinical applications," Adv. Biochem. Engin/Biotechnol. 99: 119-145; Buning et al., 2008, "Recent developments in adeno-associated virus vector technology," J. Gene Med. 10:717-733; and the references cited below, each of which is incorporated herein by reference in its entirety. The methods used to construct any embodiment of this invention are known to those with skill in nucleic acid manipulation and include genetic engineering, recombinant engineering, and synthetic techniques. See, e.g., Green and Sambrook et al, Molecular Cloning: A Laboratory Manual, Cold Spring Harbor Press, Cold Spring Harbor, NY (2012). Similarly, methods of generating rAAV virions are well known and the selection of a suitable method is not a limitation on the present invention. See, e.g., K. Fisher et al, (1993) J. Virol., 70:520-532 and U.S. Pat. No. 5,478,745.

Optionally, the fH genes described herein may be delivered via viral vectors other than rAAV. Such other viral vectors may include any virus suitable for gene therapy may be used, including but not limited to adenovirus; herpes virus; lentivirus; retrovirus; etc. Suitably, where one of these other vectors is generated, it is produced as a replication-defective viral vector.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

The pharmaceutical compositions described herein are designed for delivery to subjects in need thereof by any suitable route or a combination of different routes, e.g., direct delivery to the liver (optionally via intravenous, via the hepatic artery, or by transplant), oral, inhalation, intranasal, intratracheal, intraarterial, intraocular, intravenous, intramuscular, subcutaneous, intradermal, and other parental routes of administration. The viral vectors described herein may be delivered in a single composition or multiple compositions. Optionally, two or more different AAV may be delivered, or multiple viruses [see, e.g., WO 2011/126808 and WO 2013/049493]. In another embodiment, multiple viruses may contain different replication-defective viruses (e.g., AAV and adenovirus).

The replication-defective viruses can be formulated with a physiologically acceptable carrier for use in gene transfer and gene therapy applications. In the case of AAV viral vectors, quantification of the genome copies (GC) may be used as the measure of the dose contained in the formulation. Any method known in the art can be used to determine the genome copy (GC) number of the replication-defective virus compositions of the invention. One method for performing AAV GC number titration is as follows: purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting specific region of the viral genome (usually poly A signal).

Also, the replication-defective virus compositions can be formulated in dosage units to contain an amount of replication-defective virus that is in the range of about $1.0\times10^9$ GC to about $1.0\times10^{15}$ GC (to treat an average subject of 70 kg in body weight), and preferably $1.0\times10^{12}$ GC to $1.0\times10^{14}$ GC for a human patient. In another embodiment, the dose is less than about $1.5\times10^{11}$ GC/kg. For example, the dose of AAV virus may be about $1\times10^9$ GC, about $5\times10^9$ GC, about $1\times10^{10}$ GC, about $5\times10^{10}$ GC, or about $1\times10^{11}$ GC. In another example, the variants may be delivered in an amount of about 0.001 mg to about 10 mg/kg.

The above-described recombinant vectors may be delivered to host cells according to published methods. The rAAV, preferably suspended in a physiologically compatible carrier, may be administered to a human or non-human mammalian subject. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and/or variants and carrier(s), excipients, including other non-active conventional pharmaceutical ingredients, such as preservatives, chemical stabilizers, suspending agents, and/or surfactants. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin. Optionally, for protein-based or antibody-based compositions, excipients suitable for solid compositions may be selected, including, e.g., fillers, beads, bulking agents, disintegrants, glidants, flavorants, colorants, or other components.

The viral vectors and other constructs described herein may be used in preparing a medicament for delivering a fH variant to a subject in need thereof, supplying fH variant having an increased half-life to a subject, and/or for treating complement related disorders.

A course of treatment may optionally involve repeat administration of the same viral vector (e.g., an AAV8 vector) or a different viral vector (e.g., an AAV8 and an AAVrh10). For example, where targeted to the liver, repeat administration may be desirable over 18 months, 2 years, or a longer time period due to dilution of expression caused by natural hepatocyte proliferation. Still other combinations of viral and protein-based treatment may be selected using the viral vectors described herein. Optionally, the composition described herein may be combined in a regimen involving other anti-complement drugs (e.g., monoclonal antibodies, etc), or protein-based therapies (including, e.g., delivery of a composition containing one or more fH variants as described herein).

For example, an engineered hfH variant as described herein may be delivered in protein form. Optionally, when delivered to a subject in protein form, a fH variant may have a leader sequence, or may lack all or a portion of the leader sequence. Optionally, protein-based therapy may be used in conjunction with administration of a viral-mediated hfH variant. In one embodiment, the fH protein can provide an immediate release form of the hfH to the subject, e.g., detectable plasma levels within 2 hours post-administration, which typically will begin to be cleared from the subject within about 24 hours to about 48 hours, or to about 72 hours, should any lag time in the onset of expression from the viral-mediated delivery system be found to exist. In another embodiment, the hfH variant is further modified to extend its half-life by engineering into the variant at least one glycosylation site is engineered into at least one of the SCRs present in the variant, at least two of the SCRs present in the variant, at least three of the SCRs present in the variant, or more. For example, the glycosylation site may be engineered into one or more of SCR1, SCR2, SCR3, SCR4, SCR19, and/or SCR20. In another embodiment, SCR17 and/or SCR18 are additionally or alternatively glycosylated. In still a further embodiment, SCR4, 17 and 18 are glycosylated. In certain embodiments, a glycosylation site may be engineered into a linker. However, in such instance, the linker is preferably at least six amino acids in length up to about 18 amino acids in length, e.g., 8-18, 10-15, or 12 amino acids. Additionally, or alternatively, the engineered hfH protein variant may be pegylated, i.e., modified with a polyethylene glycol moiety using known techniques [see, e.g., Fee, Conan J.; Van Alstine, James M. (2006). "PEG-proteins: Reaction engineering and separation issues". Chemical Engineering Science 61 (3): 924].

As used herein, a glycosylation site refers to the point of attachment of oligosaccharides to a carbon atom (C-linked), nitrogen atom (N-linked), or oxygen atom (O-linked), or glycation (non-enzymatic attachment of reducing sugars to the nitrogen atom of a protein (e.g., the nitrogen atom of an asparagine (Asn) side chain that is part of an Asn-X-Ser/Thr, wherein X is any amino acid except Pro). In certain embodiments, N-glycosylation sites are desired. A variety of techniques are known in the art for engineering N-glycosylation sites. See. e.g. Y Liu et al, Biotech Prog 2009 September-October; 25(5): 1468-1475; Sala R J, Griebenos K. Glycoslylation of therapeutic proteins: an effective strategy to optimize efficacy. BioDrugs. 2010 Feb. 1; 24(1): 9-21.

Further, an engineered hfH variant as provided herein may be formulated with a suitable carrier and/or excipient for delivery to a subject by any suitable route. In addition to conventional suspension carriers, the carrier may be a liposome or a nanocarrier. Suitable doses of the hfH variant include those which achieve sufficient plasma levels to treat a complement related disorder. Examples of dosages of hfH variants include, but are not limited to, an effective amount within the dosage range of any of about 0.01 μg/kg to about 300 mg/kg, or within about 0.1 μg/kg to about 40 mg/kg, or with about 1 μg/kg to about 20 mg/kg, or within about 1 μg/kg to about 10 mg/kg. For example, when administered intraocularly, the composition may be administered at low microgram ranges, including for example about 0.1 μg/kg or less, about 0.05 μg/kg or less, or 0.01 μg/kg or less. In some embodiments, the amount of hfH variant administered to an individual is about 10 μg to about 500 mg per dose, or about 10 μg to about 50 μg, about 50 μg to about 100 μg, about 100 μg to about 200 μg, about 200 μg to about 300 μg, about 300 μg to about 500 μg, about 500 μg to about 1 mg, about 1 mg to about 10 mg, about 10 mg to about 50 mg, about 50 mg to about 100 mg, about 100 mg to about 200 mg, about 200 mg to about 300 mg, about 300 mg to about 400 mg, or about 400 mg to about 500 mg per dose.

The pharmaceutical compositions may be administered alone. Optionally, the compositions described herein may be administered in combination with other molecules known to have a beneficial effect. For example, useful cofactors include symptom-alleviating cofactors, including antiseptics, antibiotics, antiviral and antifungal agents and analgesics, anti-inflammatories, anesthetics. In another embodiment, where intraocular administration is contemplated, molecules helpful for retinal attachment or treatment of damaged retinal tissue may be desired. Examples of useful, cofactors include anti-VEGF agents (such as an antibody against VEGF), basic fibroblast growth factor (bFGF), ciliary neurotrophic factor (CNTF), axokine (a mutein of CNTF), leukemia inhibitory factor (LIF), neutrotrophin 3 (NT-3), neurotrophin-4 (NT-4), nerve growth factor (NGF), insulin-like growth factor II, prostaglandin E2, 30 kD survival factor, taurine, and vitamin A. Another suitable therapeutic may include an anti-complement antibody, e.g., an anti-complement regulator C3 (e.g., such as is commercially available as Eculizumab).

The compositions described herein (both vector-mediated and protein-based) may be administered to a subject via any route, including, but not limited to, intravenous (e.g., by infusion pumps), intraperitoneal, intraocular, intra-arterial, intrapulmonary, oral, inhalation, intravesicular, intramuscular, intra-tracheal, subcutaneous, intraocular (including, intravitreal, and intra-retinal), intrathecal, transdermal, transpleural, intraarterial, topical, inhalational (e.g., as mists of sprays), mucosal, (such as via nasal mucosa), subcutaneous, transdermal, gastrointestinal, intraarticular, intracisternal, intraventricular, rectal (i.e., via suppository), vaginal (i.e., via pessary), intracranial, intraurethral, intrahepatic, and intratumoral. In some embodiments, the compositions are administered systemically (for example by intravenous injection). In some embodiments, the compositions are administered locally (for example by intraarterial or intraocular injection).

Thus, in a further aspect, use of a pharmaceutical composition in treating a complement related disorder including, e.g., a complement factor H associated disorder such as described herein and other complement related disorders, including, without limitation: tissue damage due to ischemia-reperfusion following acute myocardial infarction, aneurysm, stroke, hemorrhagic shock, crush injury, multiple organ failure, hypovolemic shock intestinal ischemia, spinal cord injury, and traumatic brain injury; inflammatory disorders, e.g., burns, endotoxemia and septic shock, adult respiratory distress syndrome, cardiopulmonary bypass, hemodialysis; anaphylactic shock, severe asthma, angioedema, Crohn's disease, sickle cell anemia, poststreptococcal glomerulonephritis, membranous nephritis, and pancreatitis; transplant rejection, e.g., hyperacute xenograft rejection; pregnancy related diseases such as recurrent fetal loss and pre-eclampsia; adverse drug reactions, e.g., drug allergy, IL-2 induced vascular leakage syndrome and radiographic contrast media allergy; and autoimmune disorders including, but not limited to, myasthenia gravis, Alzheimer's disease, multiple sclerosis, emphysema, obesity, rheumatoid arthritis, systemic lupus erythematosus, multiple sclerosis, myasthenia gravis, insulin-dependent diabetes mellitus, acute disseminated encephalomyelitis, Addison's disease, antiphospholipid antibody syndrome, autoimmune hepatitis, Crohn's disease, Goodpasture's syndrome, Graves' disease, Guillain-Barre syndrome, Hashimoto's disease, idiopathic thrombocytopenic purpura, pemphigus, Sjogren's syndrome, and Takayasu's arteritis, post cardiopulmonary bypass complications; myocardial infarction; ischemia/reperfusion injury; stroke; acute respiratory distress syndrome (ARDS); sepsis; burn injury; inflammation associated with cardiopulmonary bypass and hemodialysis; plasmapheresis; plateletpheresis; leukophereses; extracorporeal; membrane oxygenation (ECMO); heparin-induced extracorporeal LDL precipitation (HELP); radiographic contrast media induced allergic response; transplant rejection.

It is to be noted that the term "a" or "an" refers to one or more. As such, the terms "a" (or "an"), "one or more", and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

The term "regulation" or variations thereof as used herein refers to the ability of a composition to inhibit one or more components of a biological pathway.

Unless otherwise specified herein, both homozygous subjects and heterozygous subjects are encompassed within the phrase subject having a complement mediated disorder.

A "subject" is a mammal, e.g., a human, mouse, rat, guinea pig, dog, cat, horse, cow, pig, or non-human primate, such as a monkey, chimpanzee, baboon or gorilla.

As used herein, "disease", "disorder", "dysfunction" and "condition" are used interchangeably, to indicate an abnormal state in a subject, unless otherwise specified.

Unless defined otherwise in this specification, technical and scientific terms used herein have the same meaning as commonly understood by one of ordinary skill in the art and by reference to published texts, which provide one skilled in the art with a general guide to many of the terms used in the present application.

The following examples are illustrative only and are not intended to limit the present invention.

EXAMPLES

Engineering and Cloning of Human Factor H Truncation Variant (hfH1-4.678.19-20):

Truncation variants were generated by inverse PCR method using Phusion high-fidelity DNA polymerase (Cat #M0530S, New England Biolabs) according to manufacturer's protocol. Full-length human complement factor H cDNA pCMV Sport6 used as template for inverse PCR was obtained from Thermo Fisher Scientific (Cat #MHS6278-202800294, clone ID 40148771). PCR primers used for generation of hfH1-4.678.19-20 are listed in Table 1. After PCR fragments were separated on 0.8% agarose gel and extracted by AccuPrep gel extraction kit (Cat #K-3035, Bioneer), 50 ng of gel purified fragment was used for ligation by Rapid DNA ligation Kit (Cat #K-4123, Thermo Fisher Scientific) and transformed into DH5a competent cells (Cat #1825801, Invitrogen). Positive clones were confirmed either by restriction digestion or by PCR screening using specific primers. Then, the hfH11-4.678.19-20 insert from pCMV Sport6 was released by EcoR I and Not I digestion and gel purified fragment was blunted by End-repair module (Cat #E6050S, New England Biolabs) and purified. This fragment was sub-cloned into the pCBABG vector (which has a chicken beta-actin promoter with CMV enhancer and a partial intron sequence of the same gene, and a rabbit beta-globulin gene polyadenylation signal sequence) at EcoR V site. Positive clones were selected by restriction digestion and PCR methods.

TABLE 1

| hfH Truncation variant Primers: | |
|---|---|
| hfHdSCR5R SEQ ID NO: 49 | TGA TTT TTC TTC ACA TGA AGG CAA CGG |
| hfHdSCR5F SEQ ID NO: 50 | ACC TTG AAA CCT TGT GAT TAT CCA GAC A |
| hfHdSCR9-18R SEQ ID NO: 51 | AGA TTT AAT GCA CGT GGG TTG AGC |
| hfHdSCR9-18F SEQ ID NO: 52 | AAA GAT TCT ACA GGA AAA TGT GGG CC |

Engineering and Cloning of Human Factor H Truncation Variant hfH1-4.678.17-20:

Truncation variants were generated by inverse PCR method using Phusion high-fidelity DNA polymerase (Cat #M0530S, New England Biolabs) according to manufacturer's protocol. Full length human complement factor H cDNA pCMV Sport6 (used as template for inverse PCR) was obtained from Thermo Fisher Scientific (Cat #MHS6278-202800294, clone ID 40148771). PCR primers used for generation of hfH1-4.678.17-20 are listed in Table 1. After PCR fragments were separated on 0.8% agarose gel and extracted by AccuPrep gel extraction kit (Cat #K-3035, Bioneer), 50 ng of gel purified fragment was used for ligation by Rapid DNA ligation Kit (Cat #K-4123, Thermo Fisher Scientific) and transformed into DH5a competent cells (Cat #1825801, Invitrogen). Positive clones were confirmed either by restriction digestion or by PCR screening using specific primers. Then, the engineered hfH11-4.678.17-20 variant in pCMV Sport6 was sub-cloned into pCBABG vector at EcoRI site by infusion cloning method (Clontech Cat #638909). Primers for truncation protein preparation and cloning into expression vector were in Table 2.

TABLE 2

| hfH Truncation variant Primers: | |
|---|---|
| hfHdSCR5R SEQ ID NO: 49 | TGA TTT TTC TTC ACA TGA AGG CAA CGG |
| hfHdSCR5F SEQ ID NO: 50 | ACC TTG AAA CCT TGT GAT TAT CCA GAC A |
| hfHdSCR9-16R SEQ ID NO: 53 | AGA TTT AAT GCA CGT GGG TTG AGC |
| hfHdSCR9-16F SEQ ID NO: 54 | ATAAAAACAGATTGTCTCAGTTTACCTAGCT |
| pCBAGhfH-ORF F SEQ ID NO: 55 | TTTTGGCAAAGAATTGGACGTTGTGAACAGAG TT |
| pCBAGhfH-ORF R SEQ ID NO: 56 | CCTGAGGAGTGAATTCTATCTTTTTGCACAAG TTGG |

Expression and Purification of Recombinant hfH1-4.678.19-20 Protein:

Positive clones (hfH1-4.678.19-20 in pCBARBG vector) were transfected into HEK cells to assess the stability and functional activity of hfH1-4.678.19-20 protein. About 80% confluent HEK cells in a 6-well plate (Falcon, Cat #353046) were transfected with hfH1-4.678.19-20 cDNA in pCBARBG using Lipofectamine 2000 (Cat #11668019, Invitrogen) according to manufacturer's instructions. Protein expression was confirmed by western blotting using goat anti-human factor H IgG (Cat #A237, Complement tech). For large scale protein expression, 80% confluent HEK cells in 150 cm dishes (Falcon, Cat #353025) were transfected with endotoxin free hfH1-4.678.19-20 cDNA in pCBARBG plasmid with PEI (Cat #23966, Polysciences) according to manufacturer's instructions. Two days post-transfection, supernatant was collected from the plates and filtered through 0.2 μm filter and loaded onto a PBS-equilibrated, Ox-23 (mouse anti-human fH mAb specific for SCR 2/3, cat #10402-1VL, Sigma) sepharose affinity column. After washing with PBS containing 500 mM NaCl with 25 column volumes, bound hfH11-4.678.19-20 was eluted with 100 mM Glycine HCl pH2.7 and eluted fractions (2 ml per fraction) were neutralized with 200ul of 1.5M Tris-HCl pH 8.5. Eluted protein purity was checked by SDS-PAGE and pure fraction were pooled and dialyzed with PBS with 2 changes overnight.

Engineering and Cloning of Mouse Factor H Truncation Variant (mfH1-4.678.19-20):

Truncation variants were generated by inverse PCR method using Phusion high-fidelity DNA polymerase according to manufacturer protocol. Full-length mouse complement factor H cDNA in pBluescript SK(−) used as template for inverse PCR was kindly provided by Dr M. Nonaka (University of Tokyo, Japan, Nucleotide 110-4361 of NCBI NM 009888.3). All PCR primers used for generation of mfH1-4.678.19-20 variant are listed in Table 3. After PCR fragments were separated on 0.8% agarose gel and extracted by AccuPrep gel extraction kit, 50 ng of gel purified fragment was used for ligation by Rapid DNA ligation Kit and transformed into DH5a competent cells.

Positive clones were confirmed either by restriction digestion or by PCR screening using specific primers. Then, mfH1-4.678.-19-20 insert from pBluescript SK(−) was released by Sma I and EcoR V digestion and gel purified. This fragment was sub-cloned into pCBARBG vector at EcoR V site. Positive clones were selected by restriction digestion and PCR methods.

TABLE 3

| mfH Truncation variant Primers: | |
|---|---|
| dSCR5R SEQ ID NO: 57 | TCTCTTTTCTTCACAGAAAGGCTGAGAACTCC |
| dSCR5F SEQ ID NO: 58 | ACC TTG AAA CCA TGT GAA TTT CCA CAA TTC |
| dSCR9-18F SEQ ID NO: 59 | CGA GAC TCA ACA GGG AAA TGT GG |
| dSCR9-18R SEQ ID NO: 60 | AGA CTT AAT GCA TGA GGG TTG AGG T |

Expression of Recombinant mfH1-4.678.19-20 Protein:

Positive clones (mfH1-4.678.19-20 in pCBARBG vector) were transfected into Hepa1C1C7 cells (mouse hepatoma cell line, ATCC® CRL-2026) to assess stability and functional activity of mfH1-4.678.19-20 protein. About 80% confluent cells in a 6-well plate were transfected with mfH1-4.678.19-20 cDNA using Lipofectamine 2000 according to manufacturer's instructions. Protein expression was confirmed by western blotting using rabbit anti-mouse fH IgG (Ref #1). Blots were visualized using Pierce ECL plus Western Blotting substrate (Cat #80196, Thermo Fisher Scientific).

Generation of AAV Transfer Plasmid and Virus:

mfH1-4.678.19-20 or hfH1-4.678.19-20 expression cassette from pCBARBG vector was released by Hinc II and Pst I digestion and gel purified fragment was blunted with the End Repair Module (cat #E6050S, NEB) and ligated into Nhe I- and Xho I-digested and blunted pAAV TBG-.PI.EGFP.WPRE.BGH vector (Cat #PL-C-PV0146) from the University of Pennsylvania Vector Core. Positive clones were screened by Sma I digestion.

pCBABG with hfH1-4.678.17-20 vector was modified into AAV transfer plasmid by inserting the ITRs (inverted terminal repeats) at 5' end (SEQ ID NO: 61: ctgcgcgctcgctcgctcact-gaggccgcccgggcaaagcccgggcgtcgggcgacctttggtcgcccggcctcagt-gagc gagcgagcgcgcagagagg-gagtggccaactcc-at-cactaggggttccttgtagttaat, at HincII site) and 3' end (SEQ ID NO: 62: attaactacaaggaacccctagtgatggagttggc-cactccctctctgcgcgctcgctcgctcactgaggccgggcgaccaaa ggtcgcccgacgcccgggctttgcccgggcggcctcagt-gagcgagcgagcgcgcag, at Pst I site) of the expression cassette by using Infusion cloning method. Primers were used to amplify the AAV ITRs from the pENN.AAV.TBG.PI.RBG vector used as template listed in Table 4. The pENN.AAV.TBG.PI.RBG vector was obtained from the University of Pennsylvania Vector Core (Cat #PL-C-PV1015).

TABLE 4

| ITR insertion primers | |
|---|---|
| Hinc II 5'ITR F SEQ ID NO: 63 | AAGTGCCACCTGGTCGACGCTGCGCGCTCGCT CGCT |
| Hinc II 5' ITR R SEQ ID NO: 64 | TCAATAATCAATGTCGACATTAACTACAAGGA ACCCCT |
| Pst I 3'ITR F SEQ ID NO: 65 | GAAGATCCCTCGACCTGCAGATTAACTACAAG GAACCCCT |
| Pst I 3'ITR R SEQ ID NO: 66 | ACGCCAAGCTTGGGCTGCAGCTGCGCGCTCGC TCGCTC |

Super-coiled endotoxin-free AAV plasmid was prepared by Endo free plasmid kit (cat #12362, Qiagen), and was used for AAV virus production by the University of Pennsylvania Vector Core or the University of Massachusetts Gene Therapy Center Vector Core. The packaging, purification, and titer determination of AAV encoding mfH1-4.678.19-20, hfH11-4.678.19-20 or hfH1-4.678.17-20 was accomplished by using standard procedures.

Therapeutic Efficacy of hfH1-4.678.19-20 and hfH1-4.678.17-20 AAV in $fH^{m/m}$ mice:

The generation of $fH^{m/m}$ mice which developed C3 glomerulopathy has been described previously in the paper by Lesher et al (2013) "Combination of factor H mutation and properdin deficiency causes severe C3 glomerulonephritis", J Am Soc Nephrol. 2013 January; 24(1):53-65. Epub 2012 Nov. 30. To test the expression levels, duration and therapeutic efficacy of hfH1-4.678.19-20 and hfH11-4.678.17-20 in treating C3 glomerulopathy, 10-12 weeks old $fH^{m/m}$ mice were injected with $3\times10^{12}$ gene copies/mouse (for hfH1-4.678.19-20) or $1\times10^{11}$-$1\times10^{12}$ gene copies/mouse (for hfH1-4.678.17-20) by retro-orbital route. In separate groups of mice, a control AAV vector (pAAV.TBG.NULL.rBG) was used as a control. It is known from previous studies that natural human fH is functionally active in inhibiting alternative pathway (AP) complement activation in mice (Fakhouri, F., et al, Kidney International (2010) 78, 279-286; published online 5 May 2010). Blood was collected via retro-orbital bleed prior to injection and at 1 week after injection (for hfH1-4.678.19-20) or 1, 2 weeks, 1, 2, 3 months after injection (for hfH1-4.678.17-20). The $fH^{m/m}$ mice develop spontaneous C3 glomerulopathy characterized by uncontrolled plasma AP complement activation, leading to C3, factor B (fB) and C5 consumption and prominent glomerular deposition of C3 and C5b-9 (Lesher et al 2013). If hfH1-4.678.19-20 or hfH1-4.678.17-20 is functionally active in $fH^{m/m}$ mice, one would expect a reduction in C3 and fB consumption. Therefore, as a readout for the therapeutic efficacy of hfH1-4.678.19-20 and hfH1-4.678.17-20, we examined the levels of plasma C3 and fB by western blot before and after AAV injection into $fH^{m/m}$ mice. Mouse plasma (1 μl) was diluted with sample buffer and boiled before loading onto 4-20% gradient SDS-PAGE gels under reducing conditions. Samples were then transferred to PVDF membrane and probed with appropriate antibodies. For the detection of C3 and fB, HRP-conjugated goat anti-mouse C3 Ab (1:4000, MP Biomedicals Cat #0855557) or affinity-purified goat anti-human fB Ab (cross-reacts with mouse fB; 1:2500, cat #A235, Complement Technology) were used as primary antibodies, followed by HRP-conjugated rabbit anti-goat IgG (1:4000, Cat #1721034, Bio-Rad). Blots were visualized using Pierce ECL Plus Western Blotting substrate.

Detection of hfH1-4.678.19-20 or hfH1-4.678.17-20 Protein in Mouse Blood:

To detect the presence of hfH11-4.678.19-20 or hfH1-4.678.17-20 in AAV-treated $fH^{m/m}$ mice, an ELISA method was developed and used. Briefly, 96-well plates (MaxiSorp) were pre-coated with 4 μg/ml of anti-human factor-H mAb (OX-23) at RT for 2 hr. Un-occupied binding sites on the plates were blocked using 1% bovine serum albumin (BSA) in PBS at RT for 1 h. Serially diluted mouse plasma samples in blocking buffer containing 10 mM EDTA were added to the wells and incubated at RT for 1 h, followed by 2 μg/ml of biotin-labeled anti-hfH mAb (clone L20/3, specific for SCR19 of human factor-H, Cat #518504, Bio-Legend) and incubated at RT for 1 h. After washing, plates were then incubated with Avidin-HRP (1/1000, Cat 554058, BD Biosciences) at RT for 1 h, and developed using the TMB substrate reagent (Cat 51-2606KC and BD Cat 51-2607KC, BD Biosciences).

Therapeutic Efficacy of mfH1-4.678.19-20 Delivered by AAV in $fH^{m/m}$ or $fH^{m/m}P^{-/-}$ Mice:

To test the therapeutic efficacy of mfH1-4.678.19-20 as a surrogate for hfH1-4.678.19-20, $fH^{m/m}$ mice and $fH^{m/m}P^{-/-}$ mice were infected with AAV vector containing the coding sequences for mfH1-4.678.19-20. As previously described by Lesher et al (Lesher et al, 2013, cited above), while $fH^{m/m}$ mice developed non-lethal C3 glomerulopathy with C3 and fB consumption, the double mutant $fH^{m/m}P^{-/-}$ mice ($fH^{m/m}$ mice that were rendered deficient in properdin) developed an exacerbated and lethal form of C3 glomerulopathy and died by 10-12 week old (Lesher et al 2013). Therefore, the $fH^{m/m}P^{-/-}$ mice would also allow us to use mortality as another readout for the therapeutic efficacy of mfH1-4.678.19-20 AAV. 7-week old $fH^{m/m}$ or $fH^{m/m}P^{-/-}$ mice were injected with either control AAV (pAAV.TBG.NULL.rBG) or mfH1-4.678.19-20 AAV at $3\times10^{12}$ gene copies/mouse by retro-orbital route. Blood was collected via retro-orbital bleeding prior to injection at various time points starting at 1 week after injection. To assess plasma C3 and fB levels, mouse plasma (1 μl) was diluted with sample buffer and boiled before loading onto 4-20% gradient SDS-PAGE gels under reducing conditions. Samples were then transferred to PVDF membrane and probed with appropriate antibodies. For C3 and fB, HRP-conjugated goat anti-mouse C3 Ab or affinity-purified goat anti-human fB Ab (cross reacts with mouse fB) were used as primary antibodies, followed by detection with HRP-conjugated rabbit-anti goat IgG. In some cases, the treated mice were followed for 6 or 10 months to observe the efficacy of mfH11-4.678.19-20 AAV in preventing death and/or AP complement activation using plasma C3 and fB levels as readouts.

Dosage Determination of mfH1-4.678.19-20 AAV in fH $^{m/m}$ Mice:

In experiments aimed at titrating the amount of mfH1-4.678.19-20 AAV copies needed to achieve therapeutic efficacy, 10-12 weeks old $fH^{m/m}$ mice (Lesher, 2013) were injected with $1\times10^{12}$, $3\times10^{11}$ or $1\times10^{11}$ gene copies/mouse of AAV by retro orbital route. Blood was collected via retro-orbital bleeds prior to injection and at indicated time points (1 week and 1 month after injection). Mouse plasma (1 μl) was diluted with sample buffer and boiled before loading onto 4-20% gradient SDS-PAGE gels under reducing conditions. Samples were then transferred to PVDF membrane and probed with appropriate antibodies. For the detection of C3 and fB, HRP-conjugated goat anti-mouse C3 Ab (1:4000, Cat #0855557, MP Biomedicals) or affinity-purified goat anti-human fB Ab (cross-reacts with mouse fB; 1:2500, cat #A235, Complement Technology, Inc.) were used as primary antibodies, followed by detection with HRP-conjugated rabbit anti-goat IgG (1:4000, Cat #1721034, Bio-Rad). Blots were visualized using Pierce ECL Plus Western Blotting substrate.

Detection of mfH1-4.678.19-20 Protein in Mouse Blood by ELISA:

To detect the presence of mfH11-4.678.19-20 protein in the mouse blood, an ELISA assay was developed and used. Briefly, 96-well plates were pre-coated with 2 μg/ml of mouse anti-mouse fH SCR19-20 mAb (clone-12, generated in-house by immunizing $fH^{m/m}$ mice with recombinant mouse fH SCR19-20 (Barata, L., et al, J. Immunol 190(6): 2886-95 (2013)) at 37° C. for 1-2 hr at room temperature. Un-occupied binding sites on the plates were blocked with 1% BSA in PBS at RT for 1 hr. Serially diluted mouse plasma samples in blocking buffer containing 10 mM EDTA were added to wells and incubated at RT for 1 hr, followed by biotin-labeled rabbit anti-mouse fH Ab (Lesher et al, 2013) at RT for 1 hr. Plates were incubated with Avidin-HRP at RT for 1 hr, then developed using the TMB substrate reagent.

Detection of mfH1-4.678.19-20 Protein in Mouse Plasma by Western Blotting:

To detect the presence of mfH1-4.678.19-20 protein in the mouse blood by western blot, 10 μl of mouse plasma was diluted with 90ul of PBS containing 10 mM EDTA and incubated with anti-mouse fH mAb (clone-12)-coupled Sepharose® beads for 30 min at room temperature. After washing 2 times with PBS containing 500 mM NaCl, the Sepharose® beads were boiled with SDS-PAGE sample buffer for 5 min and run on SDS-PAGE. Samples were then transferred to PVDF membrane and mfH11-4.678.19-20 protein was detected by BSA pre-absorbed rabbit anti mouse fH 19-20 Ab (Lesher et al, 2013). Blots were visualized using Pierce ECL Plus Western Blotting substrate.

Immuno-Fluorescence Staining of C3 in Kidney:

Kidneys from control AAV- or mfH1-4.678.19-20 AAV-treated $fH^{m/m}$ or $fH^{m/m}P^{-/-}$ mice were snap-frozen in OCT medium and stored at −80° C. For immunofluorescence studies, 4 μm sections were cut and used for staining. For C3 staining, FITC-conjugated goat anti-mouse C3 Ab was used (1:500, Cat #855500, MP Biomedicals) and the experiment was performed as described (Lesher et al 2013).

Mouse Survival Analysis:

The following Table provides a summary of survival data of $fH^{m/m}P^{-/-}$ mice treated with control AAV8 vector or AAV8-mfH1-4.678.19-20 vector. All 8 $fH^{m/m}P^{-/-}$ mice treated with control AAV8 vector died within 2-3 weeks of treatment, whereas 7 out of 9 $fH^{m/m}P^{-/-}$ mice treated with the AAV8-mfH1-4.678.19-20 vector were rescued from lethal C3 glomerulopathy. All mice were injected with $3\times10^{12}$ gene copies/mouse of the respective AAV virus through retro-orbital I.V. routes. Survival of control AAV- or mfH1-4.678.19-20 AAV-treated $fH^{m/m}P^{-/-}$ mice was recorded after AAV treatment for 10 months. Data were categorized as being censored (euthanized) or natural death and analyzed by GraphPad Prism (La Jolla, CA).

| AAV vector | Number of mice treated | Note |
|---|---|---|
| AAV8-mfH1-4.678.19-20 | 9 mice | 4-healthy at 9 month after gene therapy (continuing)<br>2-healthy at 6 month after gene therapy (sacrificed at 6 month) |

-continued

| AAV vector | Number of mice treated | Note |
|---|---|---|
| | | 1-healthy at 5 month after gene therapy (continuing)<br>1-Moribund at 3 month after gene therapy<br>1-Moribund at 2 weeks after gene therapy |
| Con AAV8 | 8 mice | All died 2-3 W post injection |

Heparin-Binding Assay:

To test the Heparin-binding activity of hfH1-4.678.19-20 and mfH1-4.678.19-20 proteins, 96-well plates were pre-coated with 100 μg of Heparin (Sigma, H3393) in bicarbonate buffer (pH9.6) at 37° C. for 1 hr. The unoccupied binding sites on the plates were blocked with 1% BSA in PBS at RT for 1 hr. Different amounts of hfH1-4.678.19-20 or mfH1-4.678.19-20 protein were added and incubated at RT for 1 hr, followed by 2 μg/ml of mouse anti-human fH mAb (OX-23) at RT for 1 hr. Plates were incubated with HRP-conjugated rabbit anti-mouse IgG (1/4000, Cat #A9044, Sigma) at RT for 1 hr, then developed using the TMB substrate reagent.

C3b-Binding Assay:

To test the C3b-binding activity of hfH1-4.678.19-20 and mfH1-4.678.19-20 proteins, 96-well plates were pre-coated with 2 μg/ml human C3b (Cat #A114, CompTech) at 37° C. for 1 hr. The unoccupied binding sites on the plates were blocked with 1% BSA in PBS at RT for 1 h. Different amounts of hfH11-4.678.19-20 or mfH11-4.678.19-20 protein were added and incubated at RT for 1 h, followed by 2ug/ml of mouse anti-human fH mAb (OX-23) at RT for 1 hr. Plates were incubated with HRP-conjugated rabbit anti-mouse IgG at RT for 1 hr, then developed using the TMB substrate reagent.

Assay of Fluid-Phase Cofactor Activity of fH Protein in Factor I-Mediated C3b Cleavage:

To assess the fluid phase cofactor activity of hfH11-4.678.19-20 and mfH11-4.678.19-20 proteins in factor I-mediated cleavage of C3b, 0.5 or 0.25 μg of purified hfH1-4.678.19-20 or mfH1-4.678.19-20 protein was mixed with 2 μg of human C3b in 15 μl PBS, and 1 μg of human factor I (Cat #A138, CompTech) was subsequently added and incubated at 37° C. for 15 minutes. Reaction was stopped by adding 5× reducing SDS-PAGE sample buffer. Proteolysis of C3b was determined by analyzing the cleavage of the α chain and the generation of the α41 and α39 fragments using 4-20% Gradient SDS-PAGE gels under reducing conditions, followed by western blot detection using HRP-conjugated goat anti-human C3 IgG (1/4000, Cat #855237, MP biomedicals). Blots were visualized using Pierce ECL Plus Western Blotting substrate.

Assessment of Therapeutic Efficacy of mfH1-4.678.19-20 in Preventing AP Complement Activation Caused by Membrane Complement Regulator Defects:

To determine if fH1-4.678.19-20 AAV treatment may also be effective in preventing AP complement activation caused by defects in membrane complement regulators, mfH1-4.678.19-20 was tested in a strain of mouse that is deficient in two membrane complement regulators DAF and Crry (DAF/Crry double mutant mice). The generation of DAF/Crry double mutant mice (DAF$^{-/-}$-Crry$^{flox/flox}$-Tie-2Cre$^{+}$) was previously described with a phenotype of secondary complement deficiency due to excessive AP complement activation (Barata et al, 2013). Like fH$^{m/m}$ mice, there was C3 and fB consumption in the DAF/Crry double mutant mice (Barata et al, 2013). DAF/Crry double mutant mice (10-week old) were injected with mfH1-4.678.19-20 AAV at $3\times10^{12}$ gene copies/mouse by retro orbital route. Blood was collected via retro-orbital bleeds prior to injection and at 1 week after injection. Therapeutic efficacy was assessed by measuring plasma C3 and fB levels before and after mfH11-4.678.19-20 AAV treatment using western blot analysis. For western blot, mouse plasma (1 μl) was diluted with sample buffer and boiled before loading onto 4-20% gradient SDS-PAGE gels under reducing conditions. Samples were then transferred to PVDF membrane and probed with appropriate antibodies. For the detection of mouse C3 and fB, HRP-conjugated goat anti-mouse C3 Ab (1:4000, Cat #0855557, MP Biomedicals) or affinity-purified goat anti-human fB Ab (Cat #A235, CompTech, Texas, across reacts with mouse fB) were used as primary antibodies, followed by detection with HRP-conjugated rabbit anti-goat IgG. Blots were visualized using Pierce ECL Plus Western Blotting substrate.

Generation of aHUS Mouse Model:

To create a murine aHUS model for testing the therapeutic efficacy of AAV-mediated fH gene therapy, a mutant mouse strain carrying a fH point mutation in SCR20 corresponding to human fH W1183R mutation found in aHUS patients was created by homologous recombination-based gene targeting technique (Lesher et al, 2013; Dunkelberger, et al, J Immunol. 2012 Apr. 15; 188(8): 4032-4042; Takashi et al, Blood. 2009 Mar. 19; 113(12): 2684-2694; Kimura Y1, et al., Blood. 2008 Jan. 15; 111(2):732-40. Epub 2007 Oct. 4; Kimura Y1, et al, J Clin Invest. 2010 October; 120(10): 3545-54). For this experiment, fH gene fragments were amplified from C57BL/6 mouse genomic DNA by using the Expand Long Template PCR system (Roche, Indianapolis, IN) in order to construct the gene targeting vector. The long arm of targeting vector was comprised of a 6 kb fragment containing the 21th exon and flanking intronic sequences of the mouse fH gene. It was amplified by PCR using the following primers: SEQ ID NO: 67: 5'-gcggccgccctatccatt-agtgagtgtgg-3' and SEQ ID NO: 68: 5'-ctcgaggacagc-gatgtaagaacaatc-3'. The PCR product was ligated into PCR 2.1 vector (Invitrogen) and the insert was then released from PCR2.1 vector by with Not I and XhoI restriction digestion, purified and sub-cloned into the pND1 vector upstream of the NEO cassette. The use of pND1 vector has been described in previous publications of gene targeting experiments (Lesher et al (2013); Dunkelberger et al, 2012; Miwa et al, 2009; Kimura et al, 2008; Kimura et al 2012) and this vector contains neomycin (NEO) and diphtheria toxin (DT) cassettes for positive and negative selection, respectively (Lesher et al (2013); Dunkelberger et al, 2012; Miwa et al, 2009; Kimura et al, 2008; Kimura et al 2012). The pND1 vector also contains a loxP site and two flippase recognition target (FRT) sites flanking the NEO cassette for potential removal of NEO by FLPe recombinase (Rodriguez C I, et al, Nat Genet. 2000 June; 25(2):139-40.).

The short arm sequence was comprised of a 3.85 kb fragment containing the 22$^{th}$ exon encoding SCR20 and the flanking intronic sequences of the mouse fH gene. This sequence was PCR-amplified using the following primers: SEQ ID NO: 69: 5'-ggtaccaagcttattgaccagctacagacagta-3' and SEQ ID NO: 70: 5'-ggtaccctcactcaggtgtattactc-3'. The PCR product was cloned into PCR 2.1 vector and subsequently a tryptophan (W) to arginine (R) mutation at position 1206 corresponding to W1183R mutation of human fH in SCR20 was made by site-directed mutagenesis using the Stratagene QuickChange Site-Directed Mutagenesis kit (Agilent Technologies, CA) with the following two primers, SEQ ID NO: 71: 5'-GGAATCACACAATATAATTCT-CAAAAGGAGACACACTG-3' and SEQ ID NO: 72:

5'-CAGTGTGTCTCCTTTTGAGAATTATATTGTGTGAT-TCC-3'. After W to R mutation was confirmed, the short arm fragment was released from PCR2.1 by Kpn I digestion and sub-cloned into the pND1 vector downstream of the NEO cassette at the same restriction site. The targeting vector was then linearized by Not I digestion and transfected into C57BL/6 embryonic stem (ES) cells (EmbroMAX Embryonic stem cell line-strain C57BL/6, Cat #CMTI-2, Millipore) by electroporation-method. Transfected ES cells were subjected to G418 selection starting from 48 hours after electroporation. ES cells with homologous recombination were screened by Southern blot analysis of genomic DNA after HindIII digestion with a 480 bp 3' probe amplified using SEQ ID NO: 73: 5'-ATAGCATGTGCCAGGA-GACAC-3' and SEQ ID NO: 83: 5'-AGTGTTGACTCGTG-GAGACCA-3' as primers. Wild-type allele produced a 12.5 kb fragment, whereas the targeted allele produced a 10.2 kb fragment. Correctly targeted ES cells ($fH^{W1201R(Neo\text{-}positive)/+}$) were injected into 3.5-day post-coital C57BL/6J blastocysts to generate chimeras at the University of Pennsylvania School of Medicine Transgenic Core Facility. The resultant chimeras yielded germ line transmission, as assessed by a combination of coat color and PCR screening for the detection of NEO using the following two primers: Neo-4 primer: SEQ ID NO: 74: 5-CTTGGGTGGAGAGGCTATTC-3' and SEQ ID NO: 75: Neo-5 primer: 5'-AGGTGAGATGACAGGAGATC-3'. The neomycin-resistance cassette (NEO) in the targeting vector was flanked by 2 flippase (FLP) recombinase target (FRT) sites to allow its subsequent removal by FLP recombinase. Heterozygous FH-targeted mice ($fH^{W1201R(Neo\text{-}positive)/+}$) were crossed with FLPe transgenic mice (expressing the enhanced version of FLP, on C57BL/6 genetic background) to remove the NEO from the fH allele and generate a heterozygous fH mutant mouse without the NEO gene cassette ($fH^{w1206R/+}$). $fH^{W1206R/+}$ mice were intercrossed to generate $fH^{W1206R/W1206R}$ homozygous mice on C57BL/6 genetic background. For genotyping, the following primers were used for detection of wild-type and mutated fH alleles by PCR: WR1 (FH-specific) SEQ ID NO: 76: 5'-GA-TATGGTCAATTTAGGGAAAGT, SEQ ID NO: 77: Neo7 (NEO-specific) 5'-GGGTGGGATTAGATAAATGCC-3' and SEQ ID NO: 78: WR4 (FH-specific) 5'-TACTGTCTGTAGCTGGTCAAT 3'.

The following table summarizes the treatment outcome of $fH^{W1206R/W1206R}$ mice receiving control AAV or AAV8-mfH1-4.678.19-20 vector at $3\times10^{11}$ GC/mouse.

| AAV vector | Number of mice treated | Outcome |
|---|---|---|
| AAV8-mfH1-4.678.19-20 (3 × 10^11 GC/mouse) | 3 mice | All 3 mice are alive and healthy as of date (2 months after gene therapy)<br>All have normal platelet counts |
| Con AAV8 (3 × 10^11 GC/mouse) | 2 mice | 1 died after 4 weeks of treatment<br>The remaining mouse is alive but has low platelet count |

Homozygous $fH^{W1206R/W1206R}$ mice failed to thrive with significantly lower bodyweights as evidenced at 4-6 weeks of age and a near 50% mortality rate by 30 weeks. All $fH^{W1206R/W1206R}$ mice showed one or more of the characteristic features of aHUS, i.e. renal injury (elevated blood urea nitrogen levels and/or histological signs of thrombotic microangiopathy in glomeruli), thrombocytopenia and anemia. About one third of $fH^{W1206R/W1206R}$ mice also developed severe neurological symptoms indicative of stroke. In addition to thrombotic microangiopathy in the kidney glomeruli, numerous large vessel thrombi in multiple organs (liver, lung, spleen, kidney, brain and eye) were present in $fH^{W1206R/W1206R}$ mice.

As of the timepoints reported above, all 3 $fH^{W1206R/W1206R}$ mice treated with AAV8-mfH1-4.678.19-20 were alive and healthy with normalized platelet counts, whereas 1 of 2 $fH^{W1206R/W1206R}$ mice treated with control AAV vector died (at 4 weeks after treatment) and remaining mouse was displaying symptoms of aHUS including thrombocytopenia.

Therapeutic Efficacy of mfH1-4.678.19-20 Delivered by AAV in $fH^{W1206R/W1206R}$ Mice:

To test the therapeutic efficacy of mfH1-4.678.19-20 as a surrogate for hfH1-4.678.19-20, we injected 4-week old homozygous $fH^{W1206R/W1206R}$ mice with $3\times10^{11}$ gene copies/mouse by retro-orbital route. If mfH1-4.678.19-20 is functionally active in $fH^{W1206R/W1206R}$ mice, one would expect a reduction in thrombocytopenia and renal injury. Therefore, as readouts for the therapeutic efficacy of mfH1-4.678.19-20, we counted the number of platelet and measured the level of serum blood urea nitrogen. Since $fH^{W1206R/W1206R}$ mice failed to thrive with significantly lower bodyweights evident at 4-6 weeks of age and a near 50% mortality rate by 30 weeks. The $fH^{W1206R/W1206R}$ mice would also allow us to use mortality as another readout for the therapeutic efficacy of mfH1-4.678.19-20 AAV.

Platelet Counts in Control AAV- and mfH1-4.678.19-20 AAV-Treated $fH^{W1206R/W1206R}$ Mice To determine the platelet counts in control AAV- and mfH11-4.678.19-20 AAV-treated $fH^{W1206R/W1206R}$ mice, blood was collected with EDTA (final concentration: 0.02M) via retro-orbital bleeds prior to injection and at various time points starting at 1 month after injection and analyzed on the Sysmex XT-2000iV Automated Hematology Analyzer at the CTRC Translational Core Laboratory at the Children's Hospital of Philadelphia.

Blood Urea Nitrogen (BUN) Measurement in Control AAV- and mfH1-4.678.19-20 AAV-Treated $fH^{W1206R/W1206R}$ Mice:

To measure the serum level of blood urea nitrogen, blood samples were collected via retro-orbital bleeds prior to injection and at various time points starting at 1 month after injection. Serum BUN levels were measured using urea nitrogen reagents (Sigma-Aldrich) by following the manufacturer's instructions.

Histological Examination of Kidney and Other Organs of $fH^{W1206R/W1206R}$ Mice:

Paired kidneys and other organs were collected from $fH^{W1206R/W1206R}$ mice. One was fixed in formalin solution overnight and processed for paraffin embedding, and the other was snap-frozen in OCT compound (Sakura Finetek). Kidneys and other organs were evaluated histologically for signs of aHUS thrombotic microangiopathy using light microscopy and immunohistochemistry including immunofluorescence and immunoperoxidase.

All publications cited in this specification are incorporated herein by reference. While the invention has been described with reference to particular embodiments, it will be appreciated that modifications can be made without departing from the spirit of the invention. Such modifications are intended to fall within the scope of the appended claims.

The invention claimed is:

1. A recombinant vector having packaged therein an expression cassette comprising an engineered human complement factor H (hfH) gene operably linked to expression control sequences which direct expression thereof, wherein the hfH gene encodes a soluble hfH protein variant that retains complement regulatory function, wherein the hfH protein variant comprises:

amino acids 1 to 62 of SEQ ID NO: 3 (SCR1)—L1—amino acids 1 to 57 of SEQ ID NO: 5 (SCR2)—L2—amino acids 1 to 60 of SEQ ID NO: 7 (SCR3)—L3—amino acids 1 to 53 of SEQ ID NO: 9 (SCR4)—L4—amino acids 1 to 61 of SEQ ID NO: 13 (SCR6)—L4'—amino acids 1 to 54 of SEQ ID NO: 14 (SCR7)—L5—amino acids 1 to 58 of SEQ ID NO: 16 (SCR8)—L5''—amino acids 1 to 56 of SEQ ID NO: 33 (SCR17)—L5'''—amino acids 1 to 55 of SEQ ID NO: 35 (SCR18)—L5''''—amino acids 1 to 55 of SEQ ID NO: 37 (SCR19)—L6—amino acids 1 to 65 of SEQ ID NO: 38 (SCR20), wherein "L" refers to a linker, and each of L1, L2, L3, L4, L4', L5, L5'', L5''', L5'''', and L6 is independently selected from an amino acid sequence of 1 to 18 amino acids, and wherein SCR5, SCR9, SCR10, SCR11, SCR12, SCR13, SCR14, SCR15, and SCR16 are absent.

2. The recombinant vector according to claim 1, wherein the hfH protein variant comprises an amino acid sequence at least 95% identical to amino acids 1 to 701 of SEQ ID NO: 48.

3. The recombinant vector according to claim 1, wherein the vector is an adeno-associated virus (AAV) vector, an adenovirus vector, an RNA virus vector, a lentivirus vector, or a vaccinia virus vector.

4. A pharmaceutical composition comprising a pharmaceutically acceptable carrier and the recombinant vector according to claim 1.

5. The recombinant vector according to claim 1, wherein each of L1, L2, L3, L4, L4', L5, L5'', L5''', L5'''', and L6 is independently selected from an amino acid sequence of 1 to 12 amino acids.

6. The recombinant vector according to claim 5, wherein the hfH protein variant comprises an amino acid sequence at least 95% identical to amino acids 1 to 701 of SEQ ID NO: 48.

7. A recombinant AAV vector comprising an AAV capsid having packaged therein an expression cassette comprising an engineered human complement regulator factor H (hfH) gene operably linked to expression control sequences which direct expression thereof, wherein the hfH gene encodes a soluble hfH protein variant that retains complement regulatory function, wherein the hfH protein variant comprises:

amino acids 1 to 62 of SEQ ID NO: 3 (SCR1)—L1—amino acids 1 to 57 of SEQ ID NO: 5 (SCR2)—L2—amino acids 1 to 60 of SEQ ID NO: 7 (SCR3)—L3—amino acids 1 to 53 of SEQ ID NO: 9 (SCR4)—L4—amino acids 1 to 61 of SEQ ID NO: 13 (SCR6)—L4'—amino acids 1 to 54 of SEQ ID NO: 14 (SCR7)—L5—amino acids 1 to 58 of SEQ ID NO: 16 (SCR8)—L5''—amino acids 1 to 56 of SEQ ID NO: 33 (SCR17)—L5'''—amino acids 1 to 55 of SEQ ID NO: 35 (SCR18)—L5''''—amino acids 1 to 55 of SEQ ID NO: 37 (SCR19)—L6—amino acids 1 to 65 of SEQ ID NO: 38 (SCR20), wherein "L" refers to a linker, and each of L1, L2, L3, L4, L4', L5, L5'', L5''', L5'''', and L6 is independently selected from an amino acid sequence of 1 to 18 amino acids, and wherein SCR5, SCR9, SCR10, SCR11, SCR12, SCR13, SCR14, SCR15, and SCR16 are absent.

8. The recombinant AAV vector according to claim 7, wherein the hfH protein variant comprises an amino acid sequence at least 95% identical to amino acids 1 to 701 of SEQ ID NO: 48.

9. The recombinant AAV vector according to claim 7, wherein the AAV capsid is an AAV1, an AAV2, an AAV5, an AAV8, an rh64R1, an AAV9, or an rh10 capsid.

10. The recombinant AAV vector according to claim 7, wherein the expression control sequences comprise a liver-specific promoter sequence.

11. A pharmaceutical composition comprising a pharmaceutically acceptable carrier and the recombinant AAV vector according to claim 7.

12. The recombinant AAV vector according to claim 9, wherein the AAV capsid is an AAV2 capsid.

13. The recombinant AAV vector according to claim 7, wherein the expression control sequences comprise a constitutive promoter sequence.

14. The recombinant AAV vector according to claim 7, wherein the expression control sequences comprise a chicken beta-actin promoter sequence.

15. The recombinant AAV vector according to claim 7, wherein the hfH gene is codon optimized.

16. The recombinant AAV vector according to claim 7, wherein each of L1, L2, L3, L4, L4', L5, L5'', L5''', L5'''', and L6 is independently selected from an amino acid sequence of 1 to 12 amino acids.

17. The recombinant AAV according to claim 16, wherein the hfH protein variant comprises an amino acid sequence at least 95% identical to amino acids 1 to 701 of SEQ ID NO: 48.

18. A plasmid comprising a nucleotide sequence that encodes an engineered human complement regulator factor H (hfH) gene operably linked to expression control sequences which direct expression thereof, wherein the hfH gene encodes a soluble hfH protein variant that retains complement regulatory function, wherein the hfH protein variant comprises:

amino acids 1 to 62 of SEQ ID NO: 3 (SCR1)—L1—amino acids 1 to 57 of SEQ ID NO: 5 (SCR2)—L2—amino acids 1 to 60 of SEQ ID NO: 7 (SCR3)—L3—amino acids 1 to 53 of SEQ ID NO: 9 (SCR4)—L4—amino acids 1 to 61 of SEQ ID NO: 13 (SCR6)—L4'—amino acids 1 to 54 of SEQ ID NO: 14 (SCR7)—L5—amino acids 1 to 58 of SEQ ID NO: 16 (SCR8)—L5"—amino acids 1 to 56 of SEQ ID NO: 33 (SCR17)—L5'''—amino acids 1 to 55 of SEQ ID NO: 35 (SCR18)—L5""—amino acids 1 to 55 of SEQ ID NO: 37 (SCR19)—L6—amino acids 1 to 65 of SEQ ID NO: 38 (SCR20), wherein "L" refers to a linker, and each of L1, L2, L3, L4, L4', L5, L5", L5''', L5"", and L6 is independently selected from an amino acid sequence of 1 to 18 amino acids, and wherein SCR5, SCR9, SCR10, SCR11, SCR12, SCR13, SCR14, SCR15, and SCR16 are absent.

19. The plasmid according to claim 18, wherein the hfH protein variant comprises an amino acid sequence at least 95% identical to amino acids 1 to 701 of SEQ ID NO: 48.

20. The plasmid according to claim 18, wherein the expression control sequences comprise a constitutive promoter sequence.

21. The plasmid according to claim 18, wherein the expression control sequences comprise a chicken beta-actin promoter sequence and/or a Kozak sequence.

22. A packaging host cell comprising the plasmid according to claim 18.

23. The plasmid according to claim 18, wherein each of L1, L2, L3, L4, L4', L5, L5", L5''', L5"", and L6 is independently selected from an amino acid sequence of 1 to 12 amino acids.

24. The plasmid according to claim 23, wherein the hfH protein variant comprises an amino acid sequence at least 95% identical to amino acids 1 to 701 of SEQ ID NO: 48.

* * * * *

SEQUENCE LISTING

```
Sequence total quantity: 83
SEQ ID NO: 1            moltype = DNA  length = 3696
FEATURE                 Location/Qualifiers
source                  1..3696
                        mol_type = other DNA
                        organism = Homo sapiens
CDS                     1..54
                        note = signal peptide
CDS                     55..240
                        note = SCR1
CDS                     241..252
                        note = linker 1/2
CDS                     253..423
                        note = SCR2
CDS                     424..435
                        note = linker 2/3
CDS                     436..615
                        note = SCR3
CDS                     616..627
                        note = linker 3/4
CDS                     628..786
                        note = SCR4
CDS                     787..798
                        note = Linker 4/5
CDS                     799..960
                        note = SCR5
CDS                     961..972
                        note = linker 5/6
CDS                     973..1155
                        note = SCR6
CDS                     1156..1164
                        note = linker 6/7
CDS                     1165..1326
                        note = SCR7
CDS                     1327..1341
                        note = linker 7/8
CDS                     1342..1515
                        note = SCR8
CDS                     1516..1524
                        note = linker 8/9
CDS                     1525..1692
                        note = SCR9
CDS                     1693..1704
                        note = linker 9/10
CDS                     1705..1869
                        note = SCR10
CDS                     1870..1887
                        note = linker 10/11
CDS                     1888..2052
                        note = SCR11
CDS                     2053..2070
                        note = linker 11/12
CDS                     2071..2232
                        note = SCR12
CDS                     2233..2256
                        note = linker 12/13
CDS                     2257..2409
                        note = SCR13
CDS                     2410..2430
                        note = linker 13/14
CDS                     2431..2592
                        note = SCR14
CDS                     2593..2607
                        note = linker
CDS                     2608..2778
                        note = SCR15
CDS                     2779..2790
                        note = linker
CDS                     2791..2952
                        note = SCR16
CDS                     2953..2964
                        note = linker
CDS                     2965..3129
                        note = SCR17
CDS                     3130..3141
                        note = linker 17/18
CDS                     3142..3306
                        note = SCR18
```

-continued

```
CDS                     3307..3324
                        note = linker 18/19
CDS                     3325..3489
                        note = SCR19
CDS                     3490..3498
                        note = SCR19
CDS                     3499..3696
                        note = SCR20
SEQUENCE: 1
atgagacttc tagcaaagat tatttgcctt atgttatggg ctatttgtgt agcagaagat  60
tgcaatgaac ttcctccaag aagaaataca gaaattctga caggttcctg gtctgaccaa  120
acatatccag aaggcaccca ggctatctat aaatgccgcc ctggatatag atctcttgga  180
aatataataa tggtatgcag gaagggagaa tgggttgctc ttaatccatt aaggaaatgt  240
cagaaaaggc cctgtggaca tcctggagat actccttttg gtacttttac ccttacagga  300
ggaaatgtgt ttgaatatgg tgtaaaagct gtgtatacat gtaatgaggg gtatcaattg  360
ctaggtgaga ttaattaccg tgaatgtgac acagatggat ggaccaatga tattcctata  420
tgtgaagttg tgaagtgttt accagtgaca gcaccagaga atggaaaaat tgtcagtagt  480
gcaatggaac cagatcggga ataccatttt ggacaagcag tacggtttgt atgtaactca  540
ggctacaaga ttgaaggaga tgaagaaatg cattgttcag acgatggttt ttggagtaaa  600
gagaaaccaa agtgtgtgga aatttcatgc aaatccccag atgttataaa tggatctcct  660
atatctcaga agattattta taaggagaat gaacgatttc aatataaatg taacatgggt  720
tatgaataca gtgaaagagg agatgctgta tgcactgaat ctggatggcg tccgttgcct  780
tcatgtgaag aaaaatcatg tgataatcct tatattccaa atggtgacta ctcaccttta  840
aggattaaac acagaactgg agatgaaatc acgtaccagt gtagaaatgg tttttatcct  900
gcaacccggg gaaatacagc caaatgcaca agtactggct ggatacctgc tccgagatgt  960
accttgaaac cttgtgatta tccagacatt aaacatggag gtctatatca tgagaatatg  1020
cgtagaccat actttccagt agctgtagga aaatattact cctattactg tgatgaacat  1080
tttgagactc cgtcaggaag ttactgggat cacattcatt gcacacaaga tggatggtcg  1140
ccagcagtac catgcctcag aaaatgttat tttccttatt tggaaaatgg atataatcaa  1200
aattatggaa gaaagtttgt acagggtaaa tctatagacg ttgcctgcca tcctggctac  1260
gctcttccaa aagcgcagac cacagttaca tgtatggaga atggctggtc tcctactccc  1320
agatgcatcc gtgtcaaaac atgttccaaa tcaagtatag atattgagaa tgggtttatt  1380
tctgaatctc agtatacata tgccttaaaa gaaaaagcaa aatatcaatg caaactagga  1440
tatgtaacag cagatggtga aacatcagga tcaattacat gtgggaaaga tggatggtca  1500
gctcaaccca cgtgcattaa atcttgtgat atcccagtat ttatgaatgc cagaactaaa  1560
aatgacttca catggtttaa gctgaatgac acattggact atgaatgcca tgatggttat  1620
gaaagcaata ctggaagcac cactggttcc atagtgtgtg gttacaatgg ttggtctgat  1680
ttacccatat gttatgaaag agaatgcgaa cttcctaaaa tagatgtaca cttagttcct  1740
gatcgcaaga aagaccagta taaagttgga gaggtgttga aattctcctg caaaccagga  1800
tttacaatag ttggacctaa ttccgttcag tgctaccact ttggattgtc tcctgacctc  1860
ccaatatgta aagagcaagt acaatcatgt ggtccacctc ctgaactcct caatgggaat  1920
gttaaggaaa aaacgaaaga agaatatgga cacagtgaag tggtggaata ttattgcaat  1980
cctagatttc taatgaaggg acctaataaa attcaatgtg ttgatggaga gtggacaact  2040
ttaccagtgt gtattgtgga ggagagtacc tgtggagata tacctgaact tgaacatggc  2100
tgggcccagc tttcttcccc tccttattac tatggagatt cagtggaatt caattgctca  2160
gaatcattta caatgattgg acacagatca attacgtgta ttcatggagt atggacccaa  2220
cttccccagt gtgtggcaat agataaactt aagaagtgca aatcatcaaa tttaattata  2280
cttgaggaac atttaaaaaa caagaaggaa ttcgatcata attctaacat aaggtacaga  2340
tgtagaggaa aagaaggatg gatacacaca gtctgcataa atggaagatg ggatccagaa  2400
gtgaactgct caatggcaca aatacaatta tgcccacctc cacctcagat tcccaattct  2460
cacaatatga caaccacact gaattatcgg gatggagaaa aagtatctgt tctttgccaa  2520
gaaaattatc taattcagga aggagaagaa attacatgca aagatggaag atggcagtca  2580
ataccactct gtgttgaaaa aattccatgt tcacaaccac ctcagataga acacggaacc  2640
attaattcat ccaggtcttc acaagaaagt tatgcacatg ggactaaatt gagttatact  2700
tgtgagggtg gtttcaggat atctgaagaa aatgaaacaa catgctacat gggaaaatgg  2760
agttctccac ctcagtgtga aggccttcct tgtaaatctc cacctgagat ttctcatggt  2820
gttgtagctc acatgtcaga cagttatcag tatggagaag aagttacgta caaatgtttt  2880
gaaggttttg gaattgatgg gcctgcaatt gcaaaatgct taggagaaaa atggtctcac  2940
cctccatcat gcataaaaac agattgtctc agtttaccta gctttgaaaa tgccataccc  3000
atgggagaga agaaggatgt gtataaggcg ggtgagcaag tgacttacac ttgtgcaaca  3060
tattacaaaa tggatggagc cagtaatgta acatgcatta atagcagatg gacaggaagg  3120
ccaacatgca gagacacctc ctgtgtgaat ccgcccacag tacaaaatgc ttatatagtg  3180
tcgagacaga tgagtaaata tccatctggt gagagagtac gttatcaatg taggagccct  3240
tatgaaatgt ttggggatga agaagtgatg tgtttaaatg gaaactggac ggaaccacct  3300
caatgcaaag attctacagg aaaatgtggg ccccctccac ctattgacaa tggggacatt  3360
acttcattcc cgttgtcagt atatgctcca gcttcatcag ttgagtacca atgccagaac  3420
ttgtatcaac ttgagggtaa caagcgaata acatgtagaa atggacaatg gtcagaacca  3480
ccaaaatgct tacatccgtg tgtaatatcc cgagaaatta tggaaaatta taacatagca  3540
ttaaggtgga cagccaaaca gaagctttat tcgagaacag gtgaatcagt tgaatttgtg  3600
tgtaaacggg gatatcgtct ttcatcacgt tctcacacat tgcgaacaac atgttgggat  3660
gggaaactgg agtatccaac ttgtgcaaaa agatag                           3696

SEQ ID NO: 2            moltype = AA  length = 18
FEATURE                 Location/Qualifiers
source                  1..18
                        mol_type = protein
                        organism = Homo sapiens
SEQUENCE: 2
MRLLAKIICL MLWAICVA                                               18
```

-continued

```
SEQ ID NO: 3            moltype = AA  length = 62
FEATURE                 Location/Qualifiers
source                  1..62
                        mol_type = protein
                        organism = Homo sapiens
SEQUENCE: 3
EDCNELPPRR NTEILTGSWS DQTYPEGTQA IYKCRPGYRS LGNIIMVCRK GEWVALNPLR  60
KC                                                                 62

SEQ ID NO: 4            moltype = AA  length = 4
FEATURE                 Location/Qualifiers
source                  1..4
                        mol_type = protein
                        organism = Homo sapiens
SEQUENCE: 4
QKRP                                                               4

SEQ ID NO: 5            moltype = AA  length = 57
FEATURE                 Location/Qualifiers
source                  1..57
                        mol_type = protein
                        organism = Homo sapiens
SEQUENCE: 5
CGHPGDTPFG TFTLTGGNVF EYGVKAVYTC NEGYQLLGEI NYRECDTDGW TNDIPIC     57

SEQ ID NO: 6            moltype = AA  length = 4
FEATURE                 Location/Qualifiers
source                  1..4
                        mol_type = protein
                        organism = Homo sapiens
SEQUENCE: 6
EVVK                                                               4

SEQ ID NO: 7            moltype = AA  length = 60
FEATURE                 Location/Qualifiers
source                  1..60
                        mol_type = protein
                        organism = Homo sapiens
SEQUENCE: 7
CLPVTAPENG KIVSSAMEPD REYHFGQAVR FVCNSGYKIE GDEEMHCSDD GFWSKEKPKC  60

SEQ ID NO: 8            moltype = AA  length = 4
FEATURE                 Location/Qualifiers
source                  1..4
                        mol_type = protein
                        organism = Homo sapiens
SEQUENCE: 8
VEIS                                                               4

SEQ ID NO: 9            moltype = AA  length = 53
FEATURE                 Location/Qualifiers
source                  1..53
                        mol_type = protein
                        organism = Homo sapiens
SEQUENCE: 9
CKSPDVINGS PISQKIIYKE NERFQYKCNM GYEYSERGDA VCTESGWRPL PSC         53

SEQ ID NO: 10           moltype = AA  length = 4
FEATURE                 Location/Qualifiers
source                  1..4
                        mol_type = protein
                        organism = Homo sapiens
SEQUENCE: 10
EEKS                                                               4

SEQ ID NO: 11           moltype = AA  length = 54
FEATURE                 Location/Qualifiers
source                  1..54
                        mol_type = protein
                        organism = Homo sapiens
SEQUENCE: 11
CDNPYIPNGD YSPLRIKHRT GDEITYQCRN GFYPATRGNT AKCTSTGWIP APRC        54

SEQ ID NO: 12           moltype = AA  length = 4
FEATURE                 Location/Qualifiers
source                  1..4
                        mol_type = protein
                        organism = Homo sapiens
```

-continued

```
SEQUENCE: 12
TLKP                                                                    4

SEQ ID NO: 13          moltype = AA  length = 61
FEATURE                Location/Qualifiers
source                 1..61
                       mol_type = protein
                       organism = Homo sapiens
SEQUENCE: 13
CDYPDIKHGG LYHENMRRPY FPVAVGKYYS YYCDEHFETP SGSYWDHIHC TQDGWSPAVP  60
C                                                                  61

SEQ ID NO: 14          moltype = AA  length = 54
FEATURE                Location/Qualifiers
source                 1..54
                       mol_type = protein
                       organism = Homo sapiens
SEQUENCE: 14
CYFPYLENGY NQNYGRKFVQ GKSIDVACHP GYALPKAQTT VTCMENGWSP TPRC        54

SEQ ID NO: 15          moltype = AA  length = 5
FEATURE                Location/Qualifiers
source                 1..5
                       mol_type = protein
                       organism = Homo sapiens
SEQUENCE: 15
IRVKT                                                              5

SEQ ID NO: 16          moltype = AA  length = 58
FEATURE                Location/Qualifiers
source                 1..58
                       mol_type = protein
                       organism = Homo sapiens
SEQUENCE: 16
CSKSSIDIEN GFISESQYTY ALKEKAKYQC KLGYVTADGE TSGSITCGKD GWSAQPTC    58

SEQ ID NO: 17          moltype = AA  length = 56
FEATURE                Location/Qualifiers
source                 1..56
                       mol_type = protein
                       organism = Homo sapiens
SEQUENCE: 17
CDIPVFMNAR TKNDFTWFKL NDTLDYECHD GYESNTGSTT GSIVCGYNGW SDLPIC      56

SEQ ID NO: 18          moltype = AA  length = 4
FEATURE                Location/Qualifiers
source                 1..4
                       mol_type = protein
                       organism = Homo sapiens
SEQUENCE: 18
YERE                                                               4

SEQ ID NO: 19          moltype = AA  length = 55
FEATURE                Location/Qualifiers
source                 1..55
                       mol_type = protein
                       organism = Homo sapiens
SEQUENCE: 19
CELPKIDVHL VPDRKKDQYK VGEVLKFSCK PGFTIVGPNS VQCYHFGLSP DLPIC       55

SEQ ID NO: 20          moltype = AA  length = 6
FEATURE                Location/Qualifiers
source                 1..6
                       mol_type = protein
                       organism = Homo sapiens
SEQUENCE: 20
KEQVQS                                                             6

SEQ ID NO: 21          moltype = AA  length = 55
FEATURE                Location/Qualifiers
source                 1..55
                       mol_type = protein
                       organism = Homo sapiens
SEQUENCE: 21
CGPPPELLNG NVKEKTKEEY GHSEVVEYYC NPRFLMKGPN KIQCVDGEWT TLPVC       55

SEQ ID NO: 22          moltype = AA  length = 6
FEATURE                Location/Qualifiers
source                 1..6
```

-continued

```
                        mol_type = protein
                        organism = Homo sapiens
SEQUENCE: 22
IVEEST                                                                  6

SEQ ID NO: 23           moltype = AA  length = 54
FEATURE                 Location/Qualifiers
source                  1..54
                        mol_type = protein
                        organism = Homo sapiens
SEQUENCE: 23
CGDIPELEHG WAQLSSPPYY YGDSVEFNCS ESFTMIGHRS ITCIHGVWTQ LPQC        54

SEQ ID NO: 24           moltype = AA  length = 8
FEATURE                 Location/Qualifiers
source                  1..8
                        mol_type = protein
                        organism = Homo sapiens
SEQUENCE: 24
VAIDKLKK                                                                8

SEQ ID NO: 25           moltype = AA  length = 51
FEATURE                 Location/Qualifiers
source                  1..51
                        mol_type = protein
                        organism = Homo sapiens
SEQUENCE: 25
CKSSNLIILE EHLKNKKEFD HNSNIRYRCR GKEGWIHTVC INGRWDPEVN C           51

SEQ ID NO: 26           moltype = AA  length = 7
FEATURE                 Location/Qualifiers
source                  1..7
                        mol_type = protein
                        organism = Homo sapiens
SEQUENCE: 26
SMAQIQL                                                                 7

SEQ ID NO: 27           moltype = AA  length = 54
FEATURE                 Location/Qualifiers
source                  1..54
                        mol_type = protein
                        organism = Homo sapiens
SEQUENCE: 27
CPPPPQIPNS HNMTTTLNYR DGEKVSVLCQ ENYLIQEGEE ITCKDGRWQS IPLC        54

SEQ ID NO: 28           moltype = AA  length = 5
FEATURE                 Location/Qualifiers
source                  1..5
                        mol_type = protein
                        organism = Homo sapiens
SEQUENCE: 28
VEKIP                                                                   5

SEQ ID NO: 29           moltype = AA  length = 57
FEATURE                 Location/Qualifiers
source                  1..57
                        mol_type = protein
                        organism = Homo sapiens
SEQUENCE: 29
CSQPPQIEHG TINSSRSSQE SYAHGTKLSY TCEGGFRISE ENETTCYMGK WSSPPQC     57

SEQ ID NO: 30           moltype = AA  length = 4
FEATURE                 Location/Qualifiers
source                  1..4
                        mol_type = protein
                        organism = Homo sapiens
SEQUENCE: 30
EGLP                                                                    4

SEQ ID NO: 31           moltype = AA  length = 54
FEATURE                 Location/Qualifiers
source                  1..54
                        mol_type = protein
                        organism = Homo sapiens
SEQUENCE: 31
CKSPPEISHG VVAHMSDSYQ YGEEVTYKCF EGFGIDGPAI AKCLGEKWSH PPSC        54

SEQ ID NO: 32           moltype = AA  length = 4
FEATURE                 Location/Qualifiers
```

```
source                  1..4
                        mol_type = protein
                        organism = Homo sapiens
SEQUENCE: 32
IKTD                                                                        4

SEQ ID NO: 33           moltype = AA  length = 55
FEATURE                 Location/Qualifiers
source                  1..55
                        mol_type = protein
                        organism = Homo sapiens
SEQUENCE: 33
CLSLPSFENA IPMGEKKDVY KAGEQVTYTC ATYYKMDGAS NVTCINSRWT GRPTC               55

SEQ ID NO: 34           moltype = AA  length = 4
FEATURE                 Location/Qualifiers
source                  1..4
                        mol_type = protein
                        organism = Homo sapiens
SEQUENCE: 34
RDTS                                                                        4

SEQ ID NO: 35           moltype = AA  length = 55
FEATURE                 Location/Qualifiers
source                  1..55
                        mol_type = protein
                        organism = Homo sapiens
SEQUENCE: 35
CVNPPTVQNA YIVSRQMSKY PSGERVRYQC RSPYEMFGDE EVMCLNGNWT EPPQC               55

SEQ ID NO: 36           moltype = AA  length = 6
FEATURE                 Location/Qualifiers
source                  1..6
                        mol_type = protein
                        organism = Homo sapiens
SEQUENCE: 36
KDSTGK                                                                      6

SEQ ID NO: 37           moltype = AA  length = 55
FEATURE                 Location/Qualifiers
source                  1..55
                        mol_type = protein
                        organism = Homo sapiens
SEQUENCE: 37
CGPPPPIDNG DITSFPLSVY APASSVEYQC QNLYQLEGNK RITCRNGQWS EPPKC               55

SEQ ID NO: 38           moltype = AA  length = 65
FEATURE                 Location/Qualifiers
source                  1..65
                        mol_type = protein
                        organism = Homo sapiens
SEQUENCE: 38
CVISREIMEN YNIALRWTAK QKLYSRTGES VEFVCKRGYR LSSRSHTLRT TCWDGKLEYP          60
TCAKR                                                                      65

SEQ ID NO: 39           moltype = AA  length = 1231
FEATURE                 Location/Qualifiers
SIGNAL                  1..18
DOMAIN                  19..82
                        note = Sushi 1
DOMAIN                  83..143
                        note = Sushi 1
DOMAIN                  144..207
                        note = Sushi 3
DOMAIN                  208..264
                        note = Sushi 4
DOMAIN                  265..322
                        note = Sushi 5
DOMAIN                  324..386
                        note = Sushi 6
DOMAIN                  387..444
                        note = Sushi 7
DOMAIN                  446..507
                        note = Sushi 8
DOMAIN                  515..566
                        note = Sushi 9
DOMAIN                  576..625
                        note = Sushi 10
DOMAIN                  628..686
```

-continued

```
                        note = Sushi 11
DOMAIN                  689..746
                        note = Sushi 12
DOMAIN                  751..805
                        note = Sushi 13
DOMAIN                  809..866
                        note = Sushi 14
DOMAIN                  868..928
                        note = Sushi 15
DOMAIN                  929..986
                        note = Sushi 16
DOMAIN                  987..1045
                        note = Sushi 17
DOMAIN                  1046..1104
                        note = Sushi 18
DOMAIN                  1107..1165
                        note = Sushi 19
DOMAIN                  1170..1230
                        note = Sushi 20
source                  1..1231
                        mol_type = protein
                        organism = Homo sapiens
SEQUENCE: 39
MRLLAKIICL MLWAICVAED CNELPPRRNT EILTGSWSDQ TYPEGTQAIY KCRPGYRSLG  60
NVIMVCRKGE WVALNPLRKC QKRPCGHPGD TPFGTFTLTG GNVFEYGVKA VYTCNEGYQL  120
LGEINYRECD TDGWTNDIPI CEVVKCLPVT APENGKIVSS AMEPDREYHF GQAVRFVCNS  180
GYKIEGDEEM HCSDDGFWSK EKPKCVEISC KSPDVINGSP ISQKIIYKEN ERFQYKCNMG  240
YEYSERGDAV CTESGWRPLP SCEEKSCDNP YIPNGDYSPL RIKHRTGDEI TYQCRNGFYP  300
ATRGNTAKCT STGWIPAPRC TLKPCDYPDI KHGGLYHENM RRPYFPVAVG KYYSYYCDEH  360
FETPSGSYWD HIHCTQDGWS PAVPCLRKCY FPYLENGYNQ NYGRKFVQGK SIDVACHPGY  420
ALPKAQTTVT CMENGWSPTP RCIRVKTCSK SSIDIENGFI SESQYTYALK EKAKYQCKLG  480
YVTADGETSG SITCGKDGWS AQPTCIKSCD IPVFMNARTK NDFTWFKLND TLDYECHDGY  540
ESNTGSTTGS IVCGYNGWSD LPICYERECE LPKIDVHLVP DRKKDQYKVG EVLKFSCKPG  600
FTIVGPNSVQ CYHFGLSPDL PICKEQVQSC GPPPELLNGN VKEKTKEEYG HSEVVEYYCN  660
PRFLMKGPNK IQCVDGEWTT LPVCIVEEST CGDIPELEHG WAQLSSPPYY YGDSVEFNCS  720
ESFTMIGHRS ITCIHGVWTQ LPQCVAIDKL KKCKSSNLII LEEHLKNKKE FDHNSNIRYR  780
CRGKEGWIHT VCINGRWDPE VNCSMAQIQL CPPPPQIPNS HNMTTTLNYR DGEKVSVLCQ  840
ENYLIQEGEE ITCKDGRWQS IPLCVEKIPC SQPPQIEHGT INSSRSSQES YAHGTKLSYT  900
CEGGFRISEE NETTCYMGKW SSPPQCEGLP CKSPPEISHG VVAHMSDSYQ YGEEVTYKCF  960
EGFGIDGPAI AKCLGEKWSH PPSCIKTDCL SLPSFENAIP MGEKKDVYKA GEQVTYTCAT  1020
YYKMDGASNV TCINSRWTGR PTCRDTSCVN PPTVQNAYIV SRQMSKYPSG ERVRYQCRSP  1080
YEMFGDEEVM CLNGNWTEPP QCKDSTGKCG PPPPIDNGDI TSFPLSVYAP ASSVEYQCQN  1140
LYQLEGNKRI TCRNGQWSEP PKCLHPCVIS REIMENYNIA LRWTAKQKLY SRTGESVEFV  1200
CKRGYRLSSR SHTLRTTCWD GKLEYPTCAK R                                1231

SEQ ID NO: 40           moltype = AA  length = 449
FEATURE                 Location/Qualifiers
source                  1..449
                        mol_type = protein
                        organism = Homo sapiens
SEQUENCE: 40
MRLLAKIICL MLWAICVAED CNELPPRRNT EILTGSWSDQ TYPEGTQAIY KCRPGYRSLG  60
NVIMVCRKGE WVALNPLRKC QKRPCGHPGD TPFGTFTLTG GNVFEYGVKA VYTCNEGYQL  120
LGEINYRECD TDGWTNDIPI CEVVKCLPVT APENGKIVSS AMEPDREYHF GQAVRFVCNS  180
GYKIEGDEEM HCSDDGFWSK EKPKCVEISC KSPDVINGSP ISQKIIYKEN ERFQYKCNMG  240
YEYSERGDAV CTESGWRPLP SCEEKSCDNP YIPNGDYSPL RIKHRTGDEI TYQCRNGFYP  300
ATRGNTAKCT STGWIPAPRC TLKPCDYPDI KHGGLYHENM RRPYFPVAVG KYYSYYCDEH  360
FETPSGSYWD HIHCTQDGWS PAVPCLRKCY FPYLENGYNQ NYGRKFVQGK SIDVACHPGY  420
ALPKAQTTVT CMENGWSPTP RCIRVSFTL                                   449

SEQ ID NO: 41           moltype = DNA  length = 2068
FEATURE                 Location/Qualifiers
misc_feature            1..2068
                        note = engineered hfH1-4.678.19-20 variant cDNA
source                  1..2068
                        mol_type = other DNA
                        organism = synthetic construct
SEQUENCE: 41
ggacgttgtg aacagagtta gctggtaaat gtcctcttaa aagatccaaa aaatgagact  60
tctagcaaag attatttgcc ttatgttatg ggctatttgt gtagcagaag attgcaatga  120
acttcctcca agaagaaata cagaaattct gacaggttcc tggtctgacc aaacatatcc  180
agaaggcacc caggctatct ataaatgccg ccctggatat agatctcttg gaaatataat  240
aatggtatgc aggaagggag aatgggttgc tcttaatcca ttaaggaaat gtcagaaaag  300
gccctgtgga catcctggag atactccttt tggtactttt acccttacag gaggaaatgt  360
gtttgaatat ggtgtaaaag ctgtgtatac atgtaatgag gggtatcaat tgctaggtga  420
gattaattac cgtgaatgtg acacagatgg atggaccaat gatattccta tatgtgaagt  480
tgtgaagtgt ttaccagtga cagcaccaga gaatggaaaa attgtcagta gtgcaatgga  540
accagatcgg gaataccatt ttggacaagc agtacggttt gtatgtaact caggctacaa  600
gattgaagga gatgaagaaa tgcattgttc agacgatggt ttttggagta aagagaaacc  660
```

-continued

```
aaagtgtgtg gaaatttcat gcaaatcccc agatgttata aatggatctc ctatatctca  720
gaagattatt tataaggaga atgaacgatt tcaatataaa tgtaacatgg gttatgaata  780
cagtgaaaga ggagatgctg tatgcactga atctggatgg cgtccgttgc cttcatgtga  840
agaaaaatca accttgaaac cttgtgatta tccagacatt aaacatggag gtctatatca  900
tgagaatatg cgtagaccat actttccagt agctgtagga aaatattact cctattactg  960
tgatgaacat tttgagactc cgtcaggaag ttactgggat cacattcatt gcacacaaga  1020
tggatggtcg ccagcagtac catgcctcag aaaatgttat tttccttatt tggaaaatgg  1080
atataatcaa aatcatggaa gaaagtttgt acagggtaaa tctatagacg ttgcctgcca  1140
tcctggctac gctcttccaa aagcgcagac cacagttaca tgtatggaga atggctggtc  1200
tcctactccc agatgcatcc gtgtcaaaac atgttccaaa tcaagtatag atattgagaa  1260
tgggtttatt tctgaatctc agtatacata tgccttaaaa gaaaaagcga aatatcaatg  1320
caaactagga tatgtaacag cagatggtga aacatcagga tcaattagat gtgggaaaga  1380
tggatggtca gctcaaccca cgtgcattaa atctaaagat tctacaggaa aatgtgggcc  1440
ccctccacct attgacaatg gggacattac ttcattcccg ttgtcagtat atgctccagc  1500
ttcatcagtt gagtaccaat gccagaactt gtatcaactt gagggtaaca agcgaataac  1560
atgtagaaat ggacaatggt cagaaccacc aaaatgctta catccgtgtg taatatcccg  1620
agaaattatg gaaaattata acatagcatt aaggtggaca gccaaacaga agctttattc  1680
gagaacaggt gaatcagttg aatttgtgtg taaacgggga tatcgtcttt catcacgttc  1740
tcacacattg cgaacaacat gttgggatgg gaaactggag tatccaactt gtgcaaaaag  1800
atagaatcaa tcataaagtg cacaccttta ttcagaactt tagtattaaa tcagttctca  1860
atttcatttt ttatgtattg ttttactcct ttttattcat acgtaaaatt ttggattaat  1920
ttgtgaaaat gtaattataa gctgagaccg gtggctctct tcttaaaagc accatattaa  1980
atcctggaaa actaaaaaaa aaaaaaaaaa aaaaaaaaaa aaaaaaaaaa aaaaaaaaaa  2040
aaaaaaaaaa aaaaaaaaaa aaaaaaaa                                     2068

SEQ ID NO: 42          moltype = AA  length = 583
FEATURE                Location/Qualifiers
REGION                 1..583
                       note = hfH1-4.678.19-20 protein
source                 1..583
                       mol_type = protein
                       organism = synthetic construct
SEQUENCE: 42
MRLLAKIICL MLWAICVAED CNELPPRRNT EILTGSWSDQ TYPEGTQAIY KCRPGYRSLG  60
NVIMVCRKGE WVALNPLRKC QKRPCGHPGD TPFGTFTLTG GNVFEYGVKA VYTCNEGYQL  120
LGEINYRECD TDGWTNDIPI CEVVKCLPVT APENGKIVSS AMEPDREYHF GQAVRFVCNS  180
GYKIEGDEEM HCSDDGFWSK EKPKCVEISC KSPDVINGSP ISQKIIYKEN ERFQYKCNMG  240
YEYSERGDAV CTESGWRPLP SCEEKSTLKP CDYPDIKHGG LYHENMRRPY FPVAVGKYYS  300
YYCDEHFETP SGSYWDHIHC TQDGWSPAVP CLRKCYFPYL ENGYNQNHGR KFVQGKSIDV  360
ACHPGYALPK AQTTVTCMEN GWSPTPRCIR VKTCSKSSID IENGFISESQ YTYALKEKAK  420
YQCKLGYVTA DGETSGSIRC GKDGWSAQPT CIKSKDSTGK CGPPPPIDNG DITSFPLSVY  480
APASSVEYQC QNLYQLEGNK RITCRNGQWS EPPKCLHPCV ISREIMENYN IALRWTAKQK  540
LYSRTGESVE FVCKRGYRLS SRSHTLRTTC WDGKLEYPTC AKR                    583

SEQ ID NO: 43          moltype = DNA  length = 2406
FEATURE                Location/Qualifiers
misc_feature           1..2406
                       note = murine fH1-4.678.19-20
source                 1..2406
                       mol_type = other DNA
                       organism = synthetic construct
SEQUENCE: 43
ggtctactat tttagtttac tttgcagaag ttgctcatgg gcggagcaat cctgatttcc  60
taaactgact ttcaacttcc ctttgaagca agtctttccc tgctgtgacc acagttcata  120
gcagagagga actggatggt acagcacaga tttctcttgg agtcagttgg tcccagaaag  180
atccaaatta tgagactgtc agcaagaatt atttggctta tattatggac tgtttgtgca  240
gcagaagatt gtaaaggtcc tcctccaaga gaaaattcag aaattctctc aggctcgtgg  300
tcagaacaac tatatccaga aggcacccag gctacctaca aatgccgccc tggataccga  360
acacttggca ctattgtaaa agtatgcaag aatggaaaat gggtggcgtc taacccatcc  420
aggatatgtc ggaaaaagcc ttgtgggcat cccggagaca caccctttgg gtcctttagg  480
ctggcagttg gatctcaatt tgagtttggt gcaaaggttg tttatacctg tgatgatggg  540
tatcaactat taggtgaaat tgattaccgt gaatgtggtg cagatgggtg gatcaatgat  600
attccactat gtgaagttgt gaagtgtcta cctgtgacag aactcgagaa tggaagaatt  660
gtgagtggtg cagcagaaac agaccaggaa tactattttg gacaggtggt gcggtttgaa  720
tgcaattcag gcttcaagat tgaaggacat aaggaaattc attgctcaga aaatggcctt  780
tggagcaatg aaaagccacg atgtgtggaa attctctgca caccaccgcg agtggaaaat  840
ggagatggta taaatgtgaa accagtttac aaggagaatg aaagatacca ctataagtgt  900
aagcatggtt atgtgcccaa agaaagaggg gatgccgtct gcacaggctc tggatggagt  960
tctcagcctt tctgtgaaga aaagagaacc ttgaaaccat gtgaatttcc acaattcaaa  1020
tatggacgtc tgtattatga agagagcctg agacccaact tcccagtatc tataggaaat  1080
aagtacagct ataagtgtga caacgggttt tcaccacctt ctgggtattc ctgggactac  1140
cttcgttgca cagcacaagg gtgggagcct gaagtcccat gcgtcaggaa atgtgttttc  1200
cattatgtgg agaatggaga ctctgcatac tgggaaaaag tatatgtgca gggtcagtct  1260
ttaaaagtcc agtgttacaa tggctatagt cttcaaaatg gtcaagacac aatgacatgt  1320
acagagaatg gctggtcccc tcctcccaaa tgcatccgta tcaagacatg ttcagcatca  1380
gatatacaca ttgacaatgg atttctttct gaatcttctt ctatatatgc tctaaataga  1440
gaaacatcct atagatgtaa gcagggatat gtgacaaata ctggagaaat atcaggatca  1500
ataacttgcc ttcaaaatgg atggtcacct caaccctcat gcattaagtc tcgagactca  1560
acagggaaat gtgggcctcc tccacctatt gacaatggag acatcacctc cttgtcatta  1620
```

-continued

```
ccagtatatg aaccattatc atcagttgaa tatcaatgcc agaagtatta tctccttaag  1680
ggaaagaaga caataacatg tagaaatgga aagtggtctg agccaccaac atgcttacat  1740
gcatgtgtaa taccagaaaa cattatggaa tcacacaata taattctcaa atggagacac  1800
actgaaaaga tttattccca ttcaggggag gatattgaat ttggatgtaa atatggatat  1860
tataaagcaa gagattcacc gccatttcgt acaaagtgca ttaatggcac catcaattat  1920
cccacttgtg tataaaatca taatacattt attagttgat tttattgttt agaaaggcac  1980
atgcatgtga ctaatatact ttcaatttgc attgaagtat tgtttaactc atgtcttctc  2040
ataaatataa acatttttgt tatatggtga ttaatttgta actttaaaaa ctattgccaa  2100
aatgcaaaag cagtaattca aaactcctaa tctaaaatat gatatgtcca aggacaaact  2160
atttcaatca agaaagtaga tgtaagttct tcaacatctg tttctattca gaactttctc  2220
agattttcct ggatacettt tgatgtaagg tcctgattta cagtggataa aggatatatt  2280
gactgattct tcaaattaat atgatttccc aaagcatgta acaaccaaac tatcatatat  2340
tatatgacta atgcatacaa ttaattacta tataatactt tcaaataaaa gaatctaaga  2400
aacttc                                                              2406

SEQ ID NO: 44          moltype = AA  length = 599
FEATURE                Location/Qualifiers
REGION                 1..599
                       note = mouse factor H truncation construct mFH1-4.678.19-20
source                 1..599
                       mol_type = protein
                       organism = synthetic construct
SEQUENCE: 44
MVQHRFLLES VGPRKIQIMR LSARIIWLIL WTVCAAEDCK GPPPRENSEI LSGSWSEQLY  60
PEGTQATYKC RPGYRTLGTI VKVCKNGKWV ASNPSRICRK KPCGHPGDTP FGSFRLAVGS  120
QFEFGAKVVY TCDDGYQLLG EIDYRECGAD GWINDIPLCE VVKCLPVTEL ENGRIVSGAA  180
ETDQEYYFGQ VVRFECNSGF KIEGHKEIHC SENGLWSNEK PRCVEILCTP PRVENGDGIN  240
VKPVYKENER YHYKCKHGYV PKERGDAVCT GSGWSSQPFC EEKRTLKPCE FPQFKYGRLY  300
YEESLRPNFP VSIGNKYSYK CDNGFSPPSG YSWDYLRCTA QGWEPEVPCV RKCVFHYVEN  360
GDSAYWEKVY VQGQSLKVQC YNGYSLQNGQ DTMTCTENGW SPPPKCIRIK TCSASDIHID  420
NGFLSESSSI YALNRETSYR CKQGYVTNTG EISGSITCLQ NGWSPQPSCI KSRDSTGKCG  480
PPPPIDNGDI TSLSLPVYEP LSSVEYQCQK YYLLKGKKTI TCRNGKWSEP PTCLHACVIP  540
ENIMESHNII LKWRHTEKIY SHSGEDIEFG CKYGYYKARD SPPFRTKCIN GTINYPTCV   599

SEQ ID NO: 45          moltype = DNA  length = 2106
FEATURE                Location/Qualifiers
misc_feature           1..2106
                       note = engineered fH SCR1-4, 6-8, 17-20
source                 1..2106
                       mol_type = other DNA
                       organism = synthetic construct
CDS                    1..2106
SEQUENCE: 45
atgagacttc tagcaaagat tatttgcctt atgttatggg ctatttgtgt agcagaagat  60
tgcaatgaac ttcctccaag aagaaataca gaaattctga caggttcctg gtctgaccaa  120
acatatccag aaggcaccca ggctatctat aaatgccgcc ctggatatag atctcttgga  180
aatataataa tggtatgcag gaagggagaa tgggttgctc ttaatccatt aaggaaatgt  240
cagaaaaggc cctgtggaca tcctggagat actcctttg  gtacttttac ccttacagga  300
ggaaatgtgt ttgaatatgg tgtaaaagct gtgtatacat gtaatgaggg gtatcaattg  360
ctaggtgaga ttaattaccg tgaatgtgac acagatggat ggaccaatga tattcctata  420
tgtgaagttg tgaagtgttt accagtgaca gcaccagaga atggaaaaat tgtcagtagt  480
gcaatggaac cagatcggga ataccatttt ggacaagcag tacggtttgt atgtaactca  540
ggctacaaga ttgaaggaga tgaagaaatg cattgttcag acgatggttt ttggagtaaa  600
gagaaaccaa agtgtgtgga aatttcatgc aaatccccag atgttataaa tggatctcct  660
atatctcaga agattattta taaggagaat gaacgatttc aatataaatg taacatgggt  720
tatgaataca gtgaaagagg agatgctgta tgcactgaat ctggatggcg tccgttgcct  780
tcatgtgaag aaaaatcaac cttgaaacct tgtgattatc cagacattaa acatggaggt  840
ctatatcatg agaatatgcg tagaccatac tttccagtag ctgtaggaaa atattactcc  900
tattactgtg atgaacattt tgagactccg tcaggaagtt actgggatca cattcattgc  960
acacaagatg gatggtcgcc agcagtacca tgcctcagaa aatgttattt tccttatttg  1020
gaaaatggat ataatcaaaa ttatggaaga aagtttgtac agggtaaatc tatagacgtt  1080
gcctgccatc ctggctacgc tcttccaaaa gcgcagacca cagttacatg tatggagaat  1140
ggctggtctc ctactcccag atgcatccgt gtcaaaacat gttccaaatc aagtatagat  1200
attgagaatg ggtttatttc tgaatctcag tatacatatg ccttaaaaga aaaagcaaaa  1260
tatcaatgca aactaggata tgtaacagca gatggtgaaa catcaggatc aattacatgt  1320
gggaaagatg gatggtcagc tcaacccacg tgcattaaat ctataaaaac agattgtctc  1380
agtttaccta gctttgaaaa tgccataccc atgggagaga agaaggatgt gtataaggcg  1440
ggtgagcaag tgacttacac ttgtgcaaca tattacaaaa tggatggagc cagtaatgta  1500
acatgcatta atagcagatg gacaggaagg ccaacatgca gagacacctc ctgtgtgaat  1560
ccgcccacag tacaaaatgc ttatatagtg tcgagacaga tgagtaaata tccatctggt  1620
gagagagtac gttatcaatg taggagccct tatgaaatgt ttggggatga agaagtgatg  1680
tgtttaaatg gaaactggac ggaaccacct caatgcaaag attctacagg aaaatgtggg  1740
ccccctccac ctattgacaa tggggacatt acttcattcc cgttgtcagt atatgctcca  1800
gcttcatcag ttgagtacca atgccagaac ttgtatcaac ttgagggtaa caagcgaata  1860
acatgtagaa atggacaatg gtcagaacca ccaaaatgct tacatccgtg tgtaatatcc  1920
cgagaaatta tggaaaatta taacatagca ttaaggtgga cagccaaaca gaagctttat  1980
tcgagaacag gtgaatcagt tgaatttgtg tgtaaacggg gatatcgtct ttcatcacgt  2040
tctcacacat tgcgaacaac atgttgggat gggaaactgg agtatccaac ttgtgcaaaa  2100
agatag                                                              2106
```

```
SEQ ID NO: 46          moltype = AA  length = 701
FEATURE                Location/Qualifiers
REGION                 1..701
                       note = Synthetic Construct
source                 1..701
                       mol_type = protein
                       organism = synthetic construct
SEQUENCE: 46
MRLLAKIICL MLWAICVAED CNELPPRRNT EILTGSWSDQ TYPEGTQAIY KCRPGYRSLG  60
NIIMVCRKGE WVALNPLRKC QKRPCGHPGD TPFGTFTLTG GNVFEYGVKA VYTCNEGYQL  120
LGEINYRECD TDGWTNDIPI CEVVKCLPVT APENGKIVSS AMEPDREYHF GQAVRFVCNS  180
GYKIEGDEEM HCSDDGFWSK EKPKCVEISC KSPDVINGSP ISQKIIYKEN ERFQYKCNMG  240
YEYSERGDAV CTESGWRPLP SCEEKSTLKP CDYPDIKHGG LYHENMRRPY FPVAVGKYYS  300
YYCDEHFETP SGSYWDHIHC TQDGWSPAVP CLRKCYFPYL ENGYNQNYGR KFVQGKSIDV  360
ACHPGYALPK AQTTVTCMEN GWSPTPRCIR VKTCSKSSID IENGFISESQ YTYALKEKAK  420
YQCKLGYVTA DGETSGSITC GKDGWSAQPT CIKSIKTDCL SLPSFENAIP MGEKKDVYKA  480
GEQVTYTCAT YYKMDGASNV TCINSRWTGR PTCRDTSCVN PPTVQNAYIV SRQMSKYPSG  540
ERVRYQCRSP YEMFGDEEVM CLNGNWTEPP QCKDSTGKCG PPPPIDNGDI TSFPLSVYAP  600
ASSVEYQCQN LYQLEGNKRI TCRNGQWSEP PKCLHPCVIS REIMENYNIA LRWTAKQKLY  660
SRTGESVEFV CKRGYRLSSR SHTLRTTCWD GKLEYPTCAK R                      701

SEQ ID NO: 47          moltype = DNA  length = 2158
FEATURE                Location/Qualifiers
misc_feature           1..2158
                       note = hfH1-4.678.17-20 containing leader and 5' UTR
source                 1..2158
                       mol_type = other DNA
                       organism = synthetic construct
SEQUENCE: 47
ggacgttgtg aacagagtta gctggtaaat gtcctcttaa aagatccaaa aaatgagact  60
tctagcaaag attatttgcc ttatgttatg ggctatttgt gtagcagaag attgcaatga  120
acttcctcca agaagaaata cagaaattct gacaggttcc tggtctgacc aaacatatcc  180
agaaggcacc caggctatct ataaatgccg ccctggatat agatctcttg gaaatataat  240
aatggtatgc aggaagggag aatgggttgc tcttaatcca ttaaggaaat gtcagaaaag  300
gccctgtgga catcctggag atactccttt tggtactttt acccttacag gaggaaatgt  360
gtttgaatat ggtgtaaaag ctgtgtatac atgtaatgag gggtatcaat tgctaggtga  420
gattaattac cgtgaatgtg acacagatgg atggaccaat gatattccta tatgtgaagt  480
tgtgaagtgt ttaccagtga cagcaccaga gaatggaaaa attgtcagta gtgcaatgga  540
accagatcgg gaataccatt ttggacaagc agtacggttt gtatgtaact caggctacaa  600
gattgaagga gatgaagaaa tgcattgttc agacgatggt ttttggagta aagagaaacc  660
aaagtgtgtg gaaatttcat gcaaatcccc agatgttata aatggatctc ctatatctca  720
gaagattatt tataaggaga atgaacgatt tcaatataaa tgtaacatgg gttatgaata  780
cagtgaaaga ggagatgctg tatgcactga atctggatgg cgtccgttgc cttcatgtga  840
agaaaaatca accttgaaac cttgtgatta tccagacatt aaacatggag gtctatatca  900
tgagaatatg cgtagaccat actttccagt agctgtagga aaatattact cctattactg  960
tgatgaacat tttgagactc cgtcaggaag ttactgggat cacattcatt gcacacaaga  1020
tggatggtcg ccagcagtac catgcctcag aaaatgttat tttccttatt tggaaaatgg  1080
atataatcaa aattatggaa gaaagtttgt acagggtaaa tctatagacg ttgcctgcca  1140
tcctggctac gctcttccaa aagcgcagac cacagttaca tgtatggaga atggctggtc  1200
tcctactccc agatgcatcc gtgtcaaaac atgttccaaa tcaagtatag atattgagaa  1260
tgggtttatt tctgaatctc agtatacata tgccttaaaa gaaaaagcaa aatatcaatg  1320
caaactagga tatgtaacag cagatggtga aacatcagga tcaattacat gtgggaaaga  1380
tggatggtca gctcaaccca cgtgcattaa atctataaaa acagattgtc tcagtttacc  1440
tagctttgaa aatgccatac ccatgggaga gaagaaggat gtgtataagg cgggtgagca  1500
agtgacttac acttgtgcaa catattacaa aatggatgga gccagtaatg taacatgcat  1560
taatagcaga tggacaggaa ggccaacatg cagagacacc tcctgtgtga atccgcccac  1620
agtacaaaat gcttatatag tgtcgagaca gatgagtaaa tatccatctg gtgagagagt  1680
acgttatcaa tgtaggagcc cttatgaaat gtttggggat gaagaagtga tgtgtttaaa  1740
tggaaactgg acggaaccac ctcaatgcaa agattctaca ggaaaatgtg ggcccccctcc  1800
acctattgac aatggggaca ttacttcatt cccgttgtca gtatatgctc cagcttcatc  1860
agttgagtac caatgccaga acttgtatca acttgagggt aacaagcgaa taacatgtag  1920
aaatggacaa tggtcagaac caccaaaatg cttacatccg tgtgtaatat cccgagaaat  1980
tatggaaaat tataacatag cattaaggtg gacagccaaa cagaagcttt attcgagaac  2040
aggtgaatca gttgaatttg tgtgtaaacg gggatatcgt ctttcatcac gttctcacac  2100
attgcgaaca acatgttggg atgggaaact ggagtatcca acttgtgcaa aaagatag    2158

SEQ ID NO: 48          moltype = AA  length = 701
FEATURE                Location/Qualifiers
REGION                 1..701
                       note = hFH 1-4.678.17-20
source                 1..701
                       mol_type = protein
                       organism = synthetic construct
SEQUENCE: 48
MRLLAKIICL MLWAICVAED CNELPPRRNT EILTGSWSDQ TYPEGTQAIY KCRPGYRSLG  60
NIIMVCRKGE WVALNPLRKC QKRPCGHPGD TPFGTFTLTG GNVFEYGVKA VYTCNEGYQL  120
LGEINYRECD TDGWTNDIPI CEVVKCLPVT APENGKIVSS AMEPDREYHF GQAVRFVCNS  180
GYKIEGDEEM HCSDDGFWSK EKPKCVEISC KSPDVINGSP ISQKIIYKEN ERFQYKCNMG  240
```

-continued

```
YEYSERGDAV CTESGWRPLP SCEEKSTLKP CDYPDIKHGG LYHENMRRPY FPVAVGKYYS  300
YYCDEHFETP SGSYWDHIHC TQDGWSPAVP CLRKCYFPYL ENGYNQNYGR KFVQGKSIDV  360
ACHPGYALPK AQTTVTCMEN GWSPTPRCIR VKTCSKSSID IENGFISESQ YTYALKEKAK  420
YQCKLGYVTA DGETSGSITC GKDGWSAQPT CIKSIKTDCL SLPSFENAIP MGEKKDVYKA  480
GEQVTYTCAT YYKMDGASNV TCINSRWTGR PTCRDTSCVN PPTVQNAYIV SRQMSKYPSG  540
ERVRYQCRSP YEMFGDEEVM CLNGNWTEPP QCKDSTGKCG PPPPIDNGDI TSFPLSVYAP  600
ASSVEYQCQN LYQLEGNKRI TCRNGQWSEP PKCLHPCVIS REIMENYNIA LRWTAKQKLY  660
SRTGESVEFV CKRGYRLSSR SHTLRTTCWD GKLEYPTCAK R                      701

SEQ ID NO: 49          moltype = DNA  length = 27
FEATURE                Location/Qualifiers
misc_feature           1..27
                       note = hfHdSCR5R truncation variant primer
source                 1..27
                       mol_type = other DNA
                       organism = synthetic construct
SEQUENCE: 49
tgatttttct tcacatgaag gcaacgg                                      27

SEQ ID NO: 50          moltype = DNA  length = 28
FEATURE                Location/Qualifiers
misc_feature           1..28
                       note = hfHdSCR5F truncation primer
source                 1..28
                       mol_type = other DNA
                       organism = synthetic construct
SEQUENCE: 50
accttgaaac cttgtgatta tccagaca                                     28

SEQ ID NO: 51          moltype = DNA  length = 24
FEATURE                Location/Qualifiers
misc_feature           1..24
                       note = hfHdSCR9-18R truncation variant primer
source                 1..24
                       mol_type = other DNA
                       organism = synthetic construct
SEQUENCE: 51
agatttaatg cacgtgggtt gagc                                         24

SEQ ID NO: 52          moltype = DNA  length = 26
FEATURE                Location/Qualifiers
misc_feature           1..26
                       note = hfHdSCR9-18F truncation variant primer
source                 1..26
                       mol_type = other DNA
                       organism = synthetic construct
SEQUENCE: 52
aaagattcta caggaaaatg tgggcc                                       26

SEQ ID NO: 53          moltype = DNA  length = 24
FEATURE                Location/Qualifiers
misc_feature           1..24
                       note = hfHdSCR9-16R truncation variant primer
source                 1..24
                       mol_type = other DNA
                       organism = synthetic construct
SEQUENCE: 53
agatttaatg cacgtgggtt gagc                                         24

SEQ ID NO: 54          moltype = DNA  length = 31
FEATURE                Location/Qualifiers
misc_feature           1..31
                       note = hfHdSCR9-16F truncation variant primer
source                 1..31
                       mol_type = other DNA
                       organism = synthetic construct
SEQUENCE: 54
ataaaaacag attgtctcag tttacctagc t                                 31

SEQ ID NO: 55          moltype = DNA  length = 34
FEATURE                Location/Qualifiers
misc_feature           1..34
                       note = pCBAGhfH-ORF F truncation variant primer
source                 1..34
                       mol_type = other DNA
                       organism = synthetic construct
SEQUENCE: 55
ttttggcaaa gaattggacg ttgtgaacag agtt                              34
```

-continued

```
SEQ ID NO: 56          moltype = DNA  length = 36
FEATURE                Location/Qualifiers
misc_feature           1..36
                       note = CCTGAGGAGTGAATTCTATCTTTTTGCACAAGTTGG
source                 1..36
                       mol_type = other DNA
                       organism = synthetic construct
SEQUENCE: 56
cctgaggagt gaattctatc tttttgcaca agttgg                           36

SEQ ID NO: 57          moltype = DNA  length = 32
FEATURE                Location/Qualifiers
misc_feature           1..32
                       note = dSCR5R
source                 1..32
                       mol_type = other DNA
                       organism = synthetic construct
SEQUENCE: 57
tctcttttct tcacagaaag gctgagaact cc                               32

SEQ ID NO: 58          moltype = DNA  length = 30
FEATURE                Location/Qualifiers
misc_feature           1..30
                       note = dSCR5F truncation varient primer
source                 1..30
                       mol_type = other DNA
                       organism = synthetic construct
SEQUENCE: 58
accttgaaac catgtgaatt tccacaattc                                  30

SEQ ID NO: 59          moltype = DNA  length = 23
FEATURE                Location/Qualifiers
misc_feature           1..23
                       note = dSCR9-18F truncation varient primer
source                 1..23
                       mol_type = other DNA
                       organism = synthetic construct
SEQUENCE: 59
cgagactcaa cagggaaatg tgg                                         23

SEQ ID NO: 60          moltype = DNA  length = 25
FEATURE                Location/Qualifiers
misc_feature           1..25
                       note = dSCR9-18R truncation primer
source                 1..25
                       mol_type = other DNA
                       organism = synthetic construct
SEQUENCE: 60
agacttaatg catgagggtt gaggt                                       25

SEQ ID NO: 61          moltype = DNA  length = 140
FEATURE                Location/Qualifiers
misc_feature           1..140
                       note = AAV 5' ITR
source                 1..140
                       mol_type = other DNA
                       organism = synthetic construct
SEQUENCE: 61
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct tgtagttaat                                             140

SEQ ID NO: 62          moltype = DNA  length = 140
FEATURE                Location/Qualifiers
misc_feature           1..140
                       note = AAV 3' ITR
source                 1..140
                       mol_type = other DNA
                       organism = synthetic construct
SEQUENCE: 62
attaactaca aggaacccct agtgatggag ttggccactc cctctctgcg cgctcgctcg  60
ctcactgagg ccgggcgacc aaaggtcgcc cgacgcccgg gctttgcccg ggcggcctca  120
gtgagcgagc gagcgcgcag                                             140

SEQ ID NO: 63          moltype = DNA  length = 36
FEATURE                Location/Qualifiers
misc_feature           1..36
                       note = Hinc II 5'ITR F insertion primer
source                 1..36
```

-continued

```
                        mol_type = other DNA
                        organism = synthetic construct
SEQUENCE: 63
aagtgccacc tggtcgacgc tgcgcgctcg ctcgct                              36

SEQ ID NO: 64           moltype = DNA  length = 38
FEATURE                 Location/Qualifiers
misc_feature            1..38
                        note = Hinc II 5'ITR R insertion primer
source                  1..38
                        mol_type = other DNA
                        organism = synthetic construct
SEQUENCE: 64
tcaataatca atgtcgacat taactacaag gaacccct                            38

SEQ ID NO: 65           moltype = DNA  length = 40
FEATURE                 Location/Qualifiers
misc_feature            1..40
                        note = Pst I 3'ITR F insertion primer
source                  1..40
                        mol_type = other DNA
                        organism = synthetic construct
SEQUENCE: 65
gaagatccct cgacctgcag attaactaca aggaacccct                          40

SEQ ID NO: 66           moltype = DNA  length = 38
FEATURE                 Location/Qualifiers
misc_feature            1..38
                        note = Pst I 3'ITR R insertion primer
source                  1..38
                        mol_type = other DNA
                        organism = synthetic construct
SEQUENCE: 66
acgccaagct tgggctgcag ctgcgcgctc gctcgctc                            38

SEQ ID NO: 67           moltype = DNA  length = 29
FEATURE                 Location/Qualifiers
misc_feature            1..29
                        note = mFH primer 21st exon + intron
source                  1..29
                        mol_type = other DNA
                        organism = synthetic construct
SEQUENCE: 67
gcggccgccc tatccattag tgagtgtgg                                      29

SEQ ID NO: 68           moltype = DNA  length = 27
FEATURE                 Location/Qualifiers
misc_feature            1..27
                        note = R primer mFH 21st exon + intron
source                  1..27
                        mol_type = other DNA
                        organism = synthetic construct
SEQUENCE: 68
ctcgaggaca gcgatgtaag aacaatc                                        27

SEQ ID NO: 69           moltype = DNA  length = 33
FEATURE                 Location/Qualifiers
misc_feature            1..33
                        note = F primer mFH SCR20 (exon 22)
source                  1..33
                        mol_type = other DNA
                        organism = synthetic construct
SEQUENCE: 69
ggtaccaagc ttattgacca gctacagaca gta                                 33

SEQ ID NO: 70           moltype = DNA  length = 26
FEATURE                 Location/Qualifiers
misc_feature            1..26
                        note = R primer mFH SCR20 (exon 22)
source                  1..26
                        mol_type = other DNA
                        organism = synthetic construct
SEQUENCE: 70
ggtaccctca ctcaggtgta ttactc                                         26

SEQ ID NO: 71           moltype = DNA  length = 38
FEATURE                 Location/Qualifiers
misc_feature            1..38
                        note = F primer W1183R mutation hFH
```

-continued

```
source                 1..38
                       mol_type = other DNA
                       organism = synthetic construct
SEQUENCE: 71
ggaatcacac aatataattc tcaaaaggag acacactg                    38

SEQ ID NO: 72          moltype = DNA  length = 38
FEATURE                Location/Qualifiers
misc_feature           1..38
                       note = R primer W1183R mutation
source                 1..38
                       mol_type = other DNA
                       organism = synthetic construct
SEQUENCE: 72
cagtgtgtct ccttttgaga attatattgt gtgattcc                    38

SEQ ID NO: 73          moltype = DNA  length = 21
FEATURE                Location/Qualifiers
misc_feature           1..21
                       note = F Primer for 480 bp 3' probe
source                 1..21
                       mol_type = other DNA
                       organism = synthetic construct
SEQUENCE: 73
agtgttgact cgtggagacc a                                      21

SEQ ID NO: 74          moltype = DNA  length = 20
FEATURE                Location/Qualifiers
misc_feature           1..20
                       note = Neo-4 primer
source                 1..20
                       mol_type = other DNA
                       organism = synthetic construct
SEQUENCE: 74
cttgggtgga gaggctattc                                        20

SEQ ID NO: 75          moltype = DNA  length = 20
FEATURE                Location/Qualifiers
misc_feature           1..20
                       note = Neo-5 primer
source                 1..20
                       mol_type = other DNA
                       organism = synthetic construct
SEQUENCE: 75
aggtgagatg acaggagatc                                        20

SEQ ID NO: 76          moltype =   length =
SEQUENCE: 76
000

SEQ ID NO: 77          moltype = DNA  length = 21
FEATURE                Location/Qualifiers
misc_feature           1..21
                       note = NEO-specific
source                 1..21
                       mol_type = other DNA
                       organism = synthetic construct
SEQUENCE: 77
gggtgggatt agataaatgc c                                      21

SEQ ID NO: 78          moltype = DNA  length = 21
FEATURE                Location/Qualifiers
misc_feature           1..21
                       note = WR4 (FH-specific)
source                 1..21
                       mol_type = other DNA
                       organism = synthetic construct
SEQUENCE: 78
tactgtctgt agctggtcaa t                                      21

SEQ ID NO: 79          moltype = DNA  length = 3759
FEATURE                Location/Qualifiers
source                 1..3759
                       mol_type = other DNA
                       organism = Mus musculus
CDS                    1..3759
SEQUENCE: 79
atggtacagc acagatttct cttggagtca gttggtccca gaaagatcca aattatgaga  60
ctgtcagcaa gaattatttg gcttatatta tggactgttt gtgcagcaga agattgtaaa  120
```

-continued

```
ggtcctcctc caagagaaaa ttcagaaatt ctctcaggct cgtggtcaga acaactatat  180
ccagaaggca cccaggctac ctacaaatgc cgccctggat accgaacact tggcactatt  240
gtaaaagtat gcaagaatgg aaaatgggtg gcgtctaacc catccaggat atgtcggaaa  300
aagccttgtg ggcatcccgg agacacaccc tttgggtcct ttaggctggc agttggatct  360
caatttgagt ttggtgcaaa ggttgtttat acctgtgatg atgggtatca actattaggt  420
gaaattgatt accgtgaatg tggtgcagat gggtggatca atgatattcc actatgtgaa  480
gttgtgaagt gtctacctgt gacagaactc gagaatggaa gaattgtgag tggtgcagca  540
gaaacagacc aggaatacta ttttggacag gtggtgcggt ttgaatgcaa ttcaggcttc  600
aagattgaag gacataagga aattcattgc tcagaaaatg gcctttggag caatgaaaag  660
ccacgatgtg tggaaattct ctgcacacca ccgcgagtgg aaaatggaga tggtataaat  720
gtgaaaccag tttacaagga gaatgaaaga taccactata agtgtaagca tggttatgtg  780
cccaaagaaa gaggggatgc cgtctgcaca ggctctggat ggagttctca gcctttctgt  840
gaagaaaaga gatgctcacc tccttatatt ctaaatggta tctacacacc tcacaggatt  900
atacacagaa gtgatgatga aatcagatat gaatgtaatt atggcttcta tcctgtaact  960
ggatcaactg tttcaaagtg tacacccact ggctggatcc ctgttccaag atgtaccttg  1020
aaaccatgtg aatttccaca attcaaatat ggacgtctgt attatgaaga gagcctgaga  1080
cccaacttcc cagtatctat aggaaataag tacagctata agtgtgacaa cgggttttca  1140
ccaccttctg ggtattcctg ggactacctt cgttgcacag cacaagggtg ggagcctgaa  1200
gtcccatgcg tcaggaaatg tgttttccat tatgtggaga atggagactc tgcatactgg  1260
gaaaaagtat atgtgcaggg tcagtcttta aaagtccagt gttacaatgg ctatagtctt  1320
caaaatggtc aagacacaat gacatgtaca gagaatggct ggtcccctcc tcccaaatgc  1380
atccgtatca agacatgttc agcatcagat atacacattg acaatggatt tctttctgaa  1440
tcttcttcta tatatgctct aaatagagaa acatcctata gatgtaagca gggatatgtg  1500
acaaatactg gagaaatatc aggatcaata acttgccttc aaaatggatg gtcacctcaa  1560
ccctcatgca ttaagtcttg tgatatgcct gtatttgaga attctataac taagaatact  1620
aggacatggt ttaagctcaa tgacaaatta gactatgaat gtctcgttgg atttgaaaat  1680
gaatataaac ataccaaagg ctctataaca tgtacttatt atggatggtc tgatacaccc  1740
tcatgttatg aaagagaatg cagtgttccc actctagacc gaaaactagt cgtttccccc  1800
agaaaagaaa aatacagagt tggagatttg ttggaattct cctgccattc aggacacaga  1860
gttgggccag attcagtgca atgctaccac tttggatggt ctcctggttt ccctacatgt  1920
aaaggtcaag tagcatcatg tgcaccacct cttgaaattc ttaatgggga aattaatgga  1980
gcaaaaaaag ttgaatacag ccatggtgaa gtggtgaaat atgattgcaa acctagattc  2040
ctactgaagg gacccaataa aatccagtgt gttgatggga attggacaac cttgcctgta  2100
tgtattgagg aggagagaac atgtggagac attcctgaac ttgaacatgg ctctgccaag  2160
tgttctgttc ctccctacca ccatggagat tcagtggagt tcatttgtga agaaaacttc  2220
acaatgattg gacatgggtc agtttcttgc attagtggaa aatggaccca gcttcctaaa  2280
tgtgttgcaa cagaccaact ggagaagtgt agagtgctga agtcaactgg catagaagca  2340
ataaaaccaa aattgactga atttacgcat aactccacca tggattacaa atgtagagac  2400
aagcaggagt acgaacgctc aatctgtatc aatggaaaat gggatcctga accaaactgt  2460
acaagcaaaa catcctgccc tcctccaccg cagattccaa atacccaagt gattgaaacc  2520
accgtgaaat acttggatgg agaaaaatta tctgttcttt gccaagacaa ttacctaact  2580
caggactcag aagaaatggt gtgcaaagat ggaaggtggc agtcattacc tcgctgcatt  2640
gaaaaaattc catgttccca gccccctaca atagaacatg gatctattaa tttacccaga  2700
tcttcagaag aaaggagaga ttccattgag tccagcagtc atgaacatgg aactacattc  2760
agctatgtct gtgatgatgg tttcaggata cctgaagaaa ataggataac ctgctacatg  2820
ggaaaatgga gcactccacc tcgctgtgtt ggacttcctt gtggacctcc accttcaatt  2880
cctcttggta ctgtttctct tgagctagag agttaccaac atggggaaga ggttacatac  2940
cattgttcta caggctttgg aattgatgga ccagcattta ttatatgcga aggaggaaag  3000
tggtctgacc caccaaaatg cataaaaacg gattgtgacg ttttacccac agttaaaaat  3060
gccataataa gaggaaagag caaaaaatca tataggacag gagaacaagt gacattcaga  3120
tgtcaatctc cttatcaaat gaatggctca gacactgtga catgtgttaa tagtcggtgg  3180
attggacagc cagtatgcaa agataattcc tgtgtggatc caccacatgt gccaaatgct  3240
actatagtaa caaggaccaa gaataaatat ctacatggtg acagagtacg ttatgaatgt  3300
aataaacctt tggaactatt tgggcaagtg gaagtgatgt gtgaaaatgg gatatggaca  3360
gaaaaaccaa agtgccgaga ctcaacaggg aaatgtgggc ctcctccacc tattgacaat  3420
ggagacatca cctccttgtc attaccagta tatgaaccat tatcatcagt tgaatatcaa  3480
tgccagaagt attatctcct taagggaaag aagacaataa catgtagaaa tggaaagtgg  3540
tctgagccac caacatgctt acatgcatgt gtaataccag aaaacattat ggaatcacac  3600
aatataattc tcaaatggag acacactgaa aagatttatt cccattcagg ggaggatatt  3660
gaatttggat gtaaatatgg atattataaa gcaagagatt caccgccatt tcgtacaaag  3720
tgcattaatg gcaccatcaa ttatcccact tgtgtataa                        3759
```

```
SEQ ID NO: 80          moltype = AA  length = 1252
FEATURE                Location/Qualifiers
source                 1..1252
                       mol_type = protein
                       organism = Mus musculus
SEQUENCE: 80
MVQHRFLLES VGPRKIQIMR LSARIIWLIL WTVCAAEDCK GPPPRENSEI LSGSWSEQLY  60
PEGTQATYKC RPGYRTLGTI VKVCKNGKWV ASNPSRICRK KPCGHPGDTP FGSFRLAVGS  120
QFEFGAKVVY TCDDGYQLLG EIDYRECGAD GWINDIPLCE VVKCLPVTEL ENGRIVSGAA  180
ETDQEYYFGQ VVRFECNSGF KIEGHKEIHC SENGLWSNEK PRCVEILCTP PRVENGDGIN  240
VKPVYKENER YHYKCKHGYV PKERGDAVCT GSGWSSQPFC EEKRCSPPYI LNGIYTPHRI  300
IHRSDDEIRY ECNYGFYPVT GSTVSKCTPT GWIPVPRCTL KPCEFPQFKY GRLYYEESLR  360
PNFPVSIGNK YSYKCDNGFS PPSGYSWDYL RCTAQGWEPE VPCVRKCVFH YVENGDSAYW  420
EKVYVQGQSL KVQCYNGYSL QNGQDTMTCT ENGWSPPPKC IRIKTCSASD IHIDNGFLSE  480
SSSIYALNRE TSYRCKQGYV TNTGEISGSI TCLQNGWSPQ PSCIKSCDMP VFENSITKNT  540
RTWFKLNDKL DYECLVGFEN EYKHTKGSIT CTYYGWSDTP SCYERECSVP TLDRKLVVSP  600
RKEKYRVGDL LEFSCHSGHR VGPDSVQCYH FGWSPGFPTC KGQVASCAPP LEIILNGEING  660
```

-continued

```
AKKVEYSHGE VVKYDCKPRF LLKGPNKIQC VDGNWTTLPV CIEEERTCGD IPELEHGSAK  720
CSVPPYHHGD SVEFICEENF TMIGHGSVSC ISGKWTQLPK CVATDQLEKC RVLKSTGIEA  780
IKPKLTEFTH NSTMDYKCRD KQEYERSICI NGKWDPEPNC TSKTSCPPPP QIPNTQVIET  840
TVKYLDGEKL SVLCQDNYLT QDSEEMVCKD GRWQSLPRCI EKIPCSQPPT IEHGSINLPR  900
SSEERRDSIE SSSHEHGTTF SYVCDDGFRI PEENRITCYM GKWSTPPRCV GLPCGPPPSI  960
PLGTVSLELE SYQHGEEVTY HCSTGFGIDG PAFIICEGGK WSDPPKCIKT DCDVLPTVKN  1020
AIIRGKSKKS YRTGEQVTFR CQSPYQMNGS DTVTCVNSRW IGQPVCKDNS CVDPPHVPNA  1080
TIVTRTKNKY LHGDRVRYEC NKPLELFGQV EVMCENGIWT EKPKCRDSTG KCGPPPPIDN  1140
GDITSLSLPV YEPLSSVEYQ CQKYYLLKGK KTITCRNGKW SEPPTCLHAC VIPENIMESH  1200
NIILKWRHTE KIYSHSGEDI EFGCKYGYYK ARDSPPFRTK CINGTINYPT CV          1252

SEQ ID NO: 81          moltype = DNA  length = 1800
FEATURE                Location/Qualifiers
misc_feature           1..1800
                       note = mfH1-4.678.19-20
source                 1..1800
                       mol_type = other DNA
                       organism = synthetic construct
CDS                    1..1800
SEQUENCE: 81
atggtacagc acagatttct cttggagtca gttggtccca gaaagatcca aattatgaga  60
ctgtcagcaa gaattatttg gcttatatta tggactgttt gtgcagcaga agattgtaaa  120
ggtcctcctc caagagaaaa ttcagaaatt ctctcaggct cgtggtcaga acaactatat  180
ccagaaggca cccaggctac ctacaaatgc cgccctggat accgaacact tggcactatt  240
gtaaaagtat gcaagaatgg aaaatgggtg gcgtctaacc catccaggat atgtcggaaa  300
aagccttgtg ggcatcccgg agacacaccc tttgggtcct ttaggctggc agttggatct  360
caatttgagt ttggtgcaaa ggttgtttat acctgtgatg atgggtatca actattaggt  420
gaaattgatt accgtgaatg tggtgcagat gggtggatca atgatattcc actatgtgaa  480
gttgtgaagt gtctacctgt gacagaactc gagaatggaa gaattgtgag tggtgcagca  540
gaaacagacc aggaatacta ttttggacag gtggtgcggt ttgaatgcaa ttcaggcttc  600
aagattgaag gacataagga aattcattgc tcagaaaatg gcctttggag caatgaaaag  660
ccacgatgtg tggaaattct ctgcacacca ccgcgagtgg aaaatggaga tggtataaat  720
gtgaaaccag tttacaagga gaatgaaaga taccactata agtgtaagca tggttatgtg  780
cccaaagaaa gaggggatgc cgtctgcaca ggctctggat ggagttctca gcctttctgt  840
gaagaaaaga gaaccttgaa accatgtgaa tttccacaat tcaaatatgg acgtctgtat  900
tatgaagaga gcctgagacc caacttccca gtatctatag gaaataagta cagctataag  960
tgtgacaacg ggttttcacc accttctggg tattcctggg actaccttcg ttgcacagca  1020
caagggtggg agcctgaagt cccatgcgtc aggaaatgtg ttttccatta tgtggagaat  1080
ggagactctg catactggga aaaagtatat gtgcagggtc agtctttaaa agtccagtgt  1140
tacaatggct atagtcttca aaatggtcaa gacacaatga catgtacaga gaatggctgg  1200
tccccctcctc ccaaatgcat ccgtatcaag acatgttcag catcagatat acacattgac  1260
aatggatttc tttctgaatc ttcttctata tatgctctaa atagagaaac atcctataga  1320
tgtaagcagg gatatgtgac aaatactgga gaaatatcag gatcaataac ttgccttcaa  1380
aatggatggt cacctcaacc ctcatgcatt aagtctcgag actcaacagg gaaatgtggg  1440
cctcctccac ctattgacaa tggagacatc acctccttgt cattaccagt atatgaacca  1500
ttatcatcag ttgaatatca atgccagaag tattatctcc ttaagggaaa gaagacaata  1560
acatgtagaa atggaaagtg gtctgagcca ccaacatgct tacatgcatg tgtaatacca  1620
gaaaacatta tggaatcaca caatataatt ctcaaatgga gacacactga aaagatttat  1680
tcccattcag ggaggatat tgaatttgga tgtaaatatg gatattataa agcaagagat  1740
tcaccgccat ttcgtacaaa gtgcattaat ggcaccatca attatcccac ttgtgtataa  1800

SEQ ID NO: 82          moltype = AA  length = 599
FEATURE                Location/Qualifiers
REGION                 1..599
                       note = Synthetic Construct
source                 1..599
                       mol_type = protein
                       organism = synthetic construct
SEQUENCE: 82
MVQHRFLLES VGPRKIQIMR LSARIIWLIL WTVCAAEDCK GPPPRENSEI LSGSWSEQLY  60
PEGTQATYKC RPGYRTLGTI VKVCKNGKWV ASNPSRICRK KPCGHPGDTP FGSFRLAVGS  120
QFEFGAKVVY TCDDGYQLLG EIDYRECGAD GWINDIPLCE VVKCLPVTEL ENGRIVSGAA  180
ETDQEYYFGQ VVRFECNSGF KIEGHKEIHC SENGLWSNEK PRCVEILCTP PRVENGDGIN  240
VKPVYKENER YHYKCKHGYV PKERGDAVCT GSGWSSQPFC EEKRTLKPCE FPQFKYGRLY  300
YEESLRPNFP VSIGNKYSYK CDNGFSPPSG YSWDYLRCTA QGWEPEVPCV RKCVFHYVEN  360
GDSAYWEKVY VQGQSLKVQC YNGYSLQNGQ DTMTCTENGW SPPPKCIRIK TCSASDIHID  420
```

-continued

```
NGFLSESSSI YALNRETSYR CKQGYVTNTG EISGSITCLQ NGWSPQPSCI KSRDSTGKCG  480
PPPPIDNGDI TSLSLPVYEP LSSVEYQCQK YYLLKGKKTI TCRNGKWSEP PTCLHACVIP  540
ENIMESHNII LKWRHTEKIY SHSGEDIEFG CKYGYYKARD SPPFRTKCIN GTINYPTCV   599

SEQ ID NO: 83          moltype = DNA  length = 21
FEATURE                Location/Qualifiers
misc_feature           1..21
                       note = 480bp 3' probel R primer
source                 1..21
                       mol_type = other DNA
                       organism = synthetic construct
SEQUENCE: 83
agtgttgact cgtggagacc a                                          21
```